United States Patent
Leonard

(10) Patent No.: US 11,497,333 B2
(45) Date of Patent: Nov. 15, 2022

(54) STOCKING AND STOCKING DONNING AND DOFFING APPARATUS AND METHODS

(71) Applicant: Ralph L. Leonard, North Charleston, SC (US)

(72) Inventor: Ralph L. Leonard, North Charleston, SC (US)

( * ) Notice: Subject to any disclaimer, the term of this patent is extended or adjusted under 35 U.S.C. 154(b) by 154 days.

(21) Appl. No.: 16/992,875

(22) Filed: Aug. 13, 2020

(65) Prior Publication Data
US 2022/0047104 A1   Feb. 17, 2022

(51) Int. Cl.
A47G 25/90   (2006.01)
A61F 13/08   (2006.01)

(52) U.S. Cl.
CPC .......... *A47G 25/905* (2013.01); *A61F 13/08* (2013.01)

(58) Field of Classification Search
CPC ..... A47G 25/90; A47G 25/905; A47G 25/908
USPC ........................................................ 223/112
See application file for complete search history.

(56) References Cited

U.S. PATENT DOCUMENTS

| | | | |
|---|---|---|---|
| 28,927 A | 6/1860 | Wheeler | |
| 255,180 A | 3/1882 | Master | |
| 1,119,930 A | 12/1914 | Decker | |
| 1,806,492 A | 5/1931 | Nestler | |
| 3,070,271 A | 12/1962 | Kennedy, Sr. | |
| 3,806,008 A * | 4/1974 | De Lettre | A47G 25/905 223/111 |
| 4,027,667 A | 6/1977 | Swallow et al. | |
| 4,130,226 A * | 12/1978 | Farrell | A47G 25/905 223/111 |
| 4,756,453 A | 7/1988 | Petit et al. | |
| 5,050,784 A | 9/1991 | Turner | |
| 5,069,374 A | 12/1991 | Williamson et al. | |
| D372,113 S | 7/1996 | Palmer | |
| 5,593,071 A * | 1/1997 | Lusk | A47G 25/905 223/111 |
| 5,630,534 A | 5/1997 | Maier et al. | |

(Continued)

FOREIGN PATENT DOCUMENTS

WO    2018156236    8/2018

OTHER PUBLICATIONS

International Search Report and Written Opinion of the International Searching Authority in International App. Pub. No. WO2018156236.

*Primary Examiner* — Nathan E Durham
(74) *Attorney, Agent, or Firm* — Nelson Mullins Riley & Scarborough LLP

(57) ABSTRACT

A method includes providing an apparatus including a frame including a first sub-frame and a second sub-frame that is slidable relative to the first sub-frame along a first direction. A first peg is coupled with the first sub-frame, and a second peg is coupled with the second sub-frame. A compression stocking is provided and includes a stocking body having a proximal end and a distal end, the body defining an opening. The compression stocking also includes a plurality of sleeves disposed on an exterior of the body, and each of the plurality of sleeves are oriented in a longitudinal direction relative to the body. The first peg and the second peg are coupled with respective sleeves of the plurality of sleeves, and the second sub-frame is slid relative to the first sub-frame in the first direction to expand the opening defined in the body.

22 Claims, 46 Drawing Sheets

(56) References Cited

U.S. PATENT DOCUMENTS

| | | | |
|---|---|---|---|
| 6,234,369 B1 * | 5/2001 | Bort | A47G 25/905 |
| | | | 223/111 |
| 6,775,849 B1 | 8/2004 | Messman | |
| 6,808,094 B1 | 10/2004 | Hogg | |
| 7,076,973 B1 | 7/2006 | Chesebro, Jr. et al. | |
| 7,699,195 B2 | 4/2010 | Scott | |
| D634,925 S | 3/2011 | Gesser et al. | |
| 7,975,886 B2 | 7/2011 | McAllister et al. | |
| D648,921 S | 11/2011 | Holtman | |
| 8,083,110 B2 | 12/2011 | Wilkens | |
| 8,528,796 B1 * | 9/2013 | Bosko | A47G 25/905 |
| | | | 223/111 |
| D747,601 S | 1/2016 | Middleton | |
| 2004/0069820 A1 | 4/2004 | Van Loef | |
| 2006/0151550 A1 | 7/2006 | Chevalier | |
| 2010/0006609 A1 | 1/2010 | McAllister et al. | |
| 2012/0061427 A1 | 3/2012 | Ruf | |
| 2012/0124717 A1 | 5/2012 | Austin | |
| 2018/0242766 A1 | 8/2018 | Leonard | |

* cited by examiner

STOCKING AND STOCKING DONNING AND DOFFING APPARATUS AND METHODS

TECHNICAL FIELD

Embodiments of the present invention generally relate to systems, assemblies, and associated methods for aiding a user in donning and doffing a stocking, such as a compression stocking. Various embodiments also relate to improved compression stockings and auxiliary devices for use with an apparatus for aiding a user in donning and doffing a stocking.

BACKGROUND

Compression stockings, sometimes referred to as graduated compression stockings or elastic stockings, are known. Such stockings are used to help prevent and/or treat swollen legs and/or feet. More particularly, chronic leg swelling, also known as edema, is caused by many conditions, including pregnancy; large varicose veins or a prior blood clot (sometimes referred to as deep venous thrombosis (DVT)) in a leg vein; and some disorders of the heart, lung, liver, and kidney. Irrespective of the cause, chronic edema can be harmful in that it can increase the risk of venous stasis ulcers on the leg (tissue death resulting in open sores); severe and recurrent skin infections on the leg (cellulitis); and falls (e.g., if the individual must wear slippers (which are often cut to accommodate the edematous foot) or other non-ideal shoes or if the individual's sensation in his or her foot is impaired due to the edema). Compression stockings can assist in treating and reducing such chronic leg swelling. Additionally, compression stockings can reduce the risk of blood clots forming in the legs, especially after surgery. Such blood clots can cause pain in the leg(s) and if they are dislodged may travel to the lungs (pulmonary thromboembolism) where they can cause shortness of breath or death.

The foregoing discussion is intended only to illustrate various aspects of the related art in the field of the invention at the time, and should not be taken as a disavowal of claim scope.

SUMMARY

Although compression stockings are known for treatment of chronic edema, users very often find such stockings extremely difficult to don (e.g., put on, or apply) and/or doff (e.g., take off, or remove). This is particularly the case for those with limited coordination, actual or imposed limits on flexibility (e.g., recent hip surgery requires minimal flexion for several weeks), and/or limited strength (e.g., those having had recent abdominal surgery are not supposed to strain), all of which are common among those who may benefit from wearing such stockings. Even with the assistance of another individual, such as a healthcare worker, it can be uncomfortable or even dangerous to the wearer or the assistant to put these stockings on. For instance, injury can occur if the assistant pushes too hard and accidentally flexes the leg in someone with recent hip surgery; if the assistant's grip slips from the stocking and he or she traumatizes the wearer's skin; or if the assistant's posture is poor and he or she hurts his or her own back when straining.

In contrast, various embodiments of the present invention provide a modified compression stocking that may be easier for a user to don and/or doff. Additionally, various embodiments of the present invention provide an automated device to help a user don and/or doff a stocking, including a compression stocking, even if that user is alone, unable to stand, has weak hand or arm strength, has impaired hip flexibility or imposed limits on the same, has impaired coordination or imposed limits on the same, or even if the user has only one hand or arm that is present and/or functional (e.g., as a result of a congenital condition, amputation, or prior stroke). Various embodiments of the invention also provides methods of using and/or manufacturing the compression stocking and methods of using and/or manufacturing the automated device. Among other things, various embodiments provide an automated device to don and/or doff a compression stocking that has a plurality of sleeves disposed on an exterior of the stocking body. Various embodiments also provide an automated device to assist a user in donning and/or doffing a stocking.

In accordance with one embodiment, the present invention provides a method. The method comprises providing an apparatus comprising a frame, the frame comprising a first sub-frame and a second sub-frame that is slidable relative to the first sub-frame along a first direction. At least one first peg is coupled with the first sub-frame, and at least one second peg is coupled with the second sub-frame. The method also comprises providing a compression stocking, the compression stocking comprising a stocking body having a proximal end and a distal end, the body defining an opening at least at the stocking body proximal end. The compression stocking also comprises a plurality of sleeves disposed on an exterior of the stocking body, and each of the plurality of sleeves are oriented in a longitudinal direction relative to the stocking body. The method also comprises coupling the at least one first peg and the at least one second peg with respective sleeves of the plurality of sleeves, and sliding the second sub-frame relative to the first sub-frame in the first direction to expand the opening defined in the stocking body.

According to another embodiment, a method is provided. The method comprises providing an apparatus comprising a base portion; a first rail coupled with the base portion, the first rail having a first longitudinal axis; and a second rail coupled with the base portion, the second rail having a second longitudinal axis. The apparatus also comprises a first post slidably coupled with the first rail, the first post slidable in a direction parallel with the first longitudinal axis between a first position and a second position; and a second post slidably coupled with the second rail, the second post slidable in a direction parallel with the second longitudinal axis between a third position and a fourth position. The method further comprises providing a stocking, the stocking comprising a stocking body defining at least one opening, the stocking having a plurality of sleeves coupled to the exterior of the stocking body. Also, the method comprises releasably coupling a respective sleeve of the plurality of sleeves of the stocking to each of the base portion, first post, and second post. Finally, the method comprises sliding the first and second posts from their respective first and third positions to their respective second and fourth positions, thereby expanding the stocking opening.

According to yet another embodiment, a method is provided. The method comprises providing an apparatus comprising a frame comprising a first sub-frame and a second sub-frame that is slidable relative to the first sub-frame along a first direction. The apparatus also comprises at least one first clasp member coupled with the first sub-frame and at least one second clasp member coupled with the second sub-frame. The method further comprises providing a compression stocking comprising a stocking body, the stocking body having an anterior portion and a posterior portion, coupling the at least one first clasp member with the posterior portion of the compression stocking, and coupling the at least one second clasp member with the anterior portion of the compression stocking. Additionally, the method comprises sliding the second sub-frame relative to the first sub-frame in the first direction to expand the anterior portion of the compression stocking relative to the posterior portion of the compression stocking.

BRIEF DESCRIPTION OF THE DRAWINGS

Figure 1A:
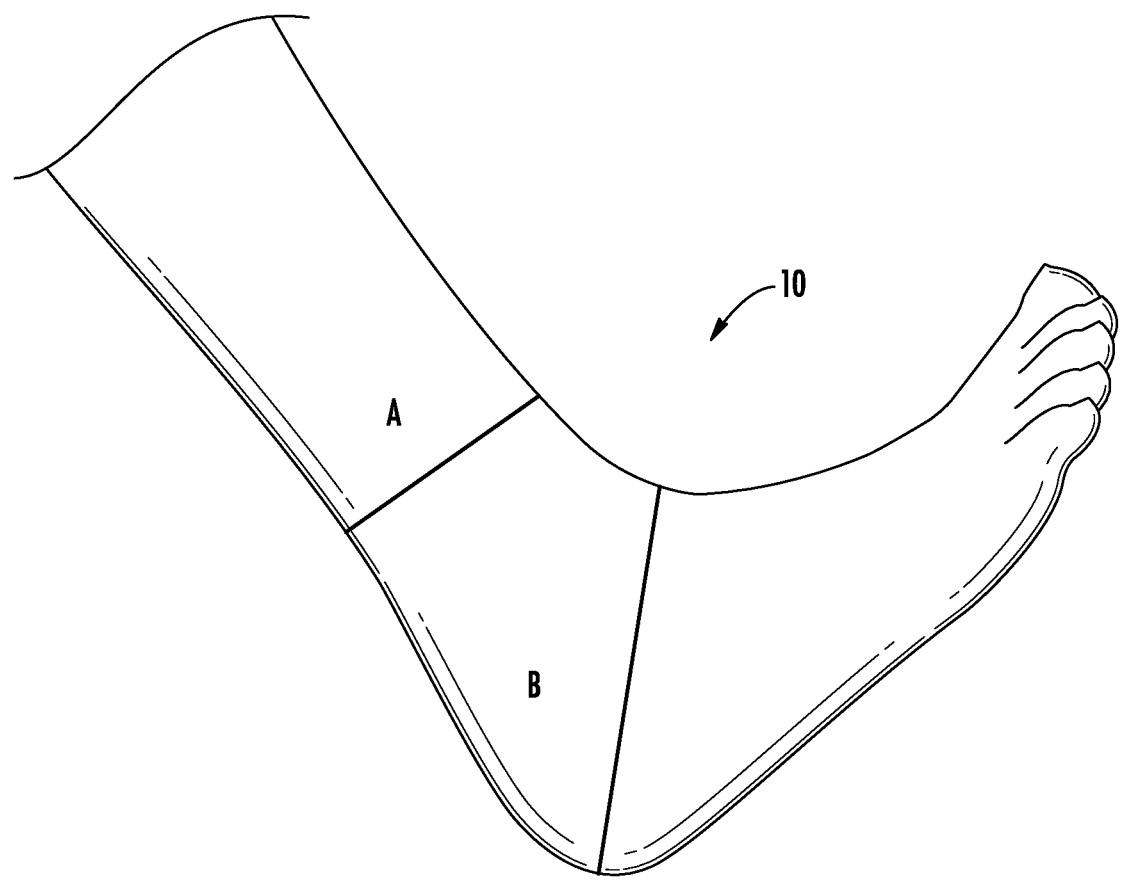
Figure 1B:
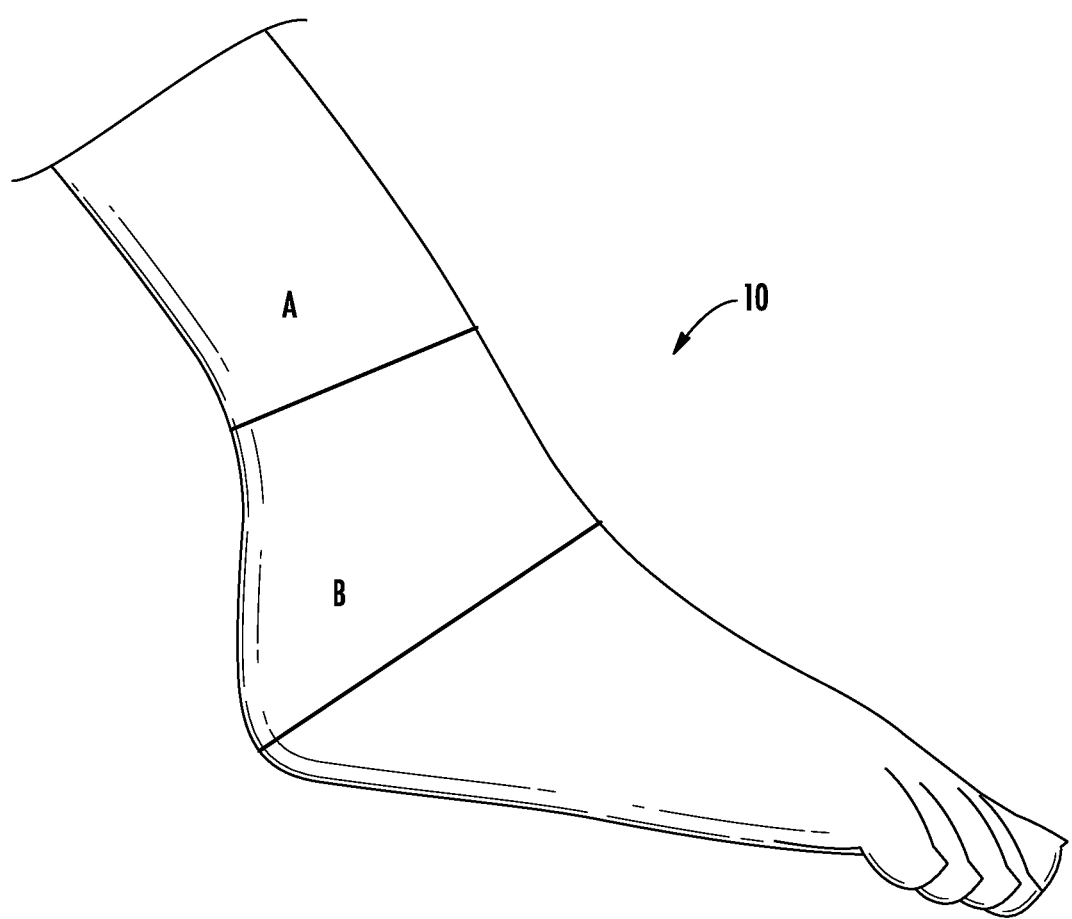
Figure 1C:
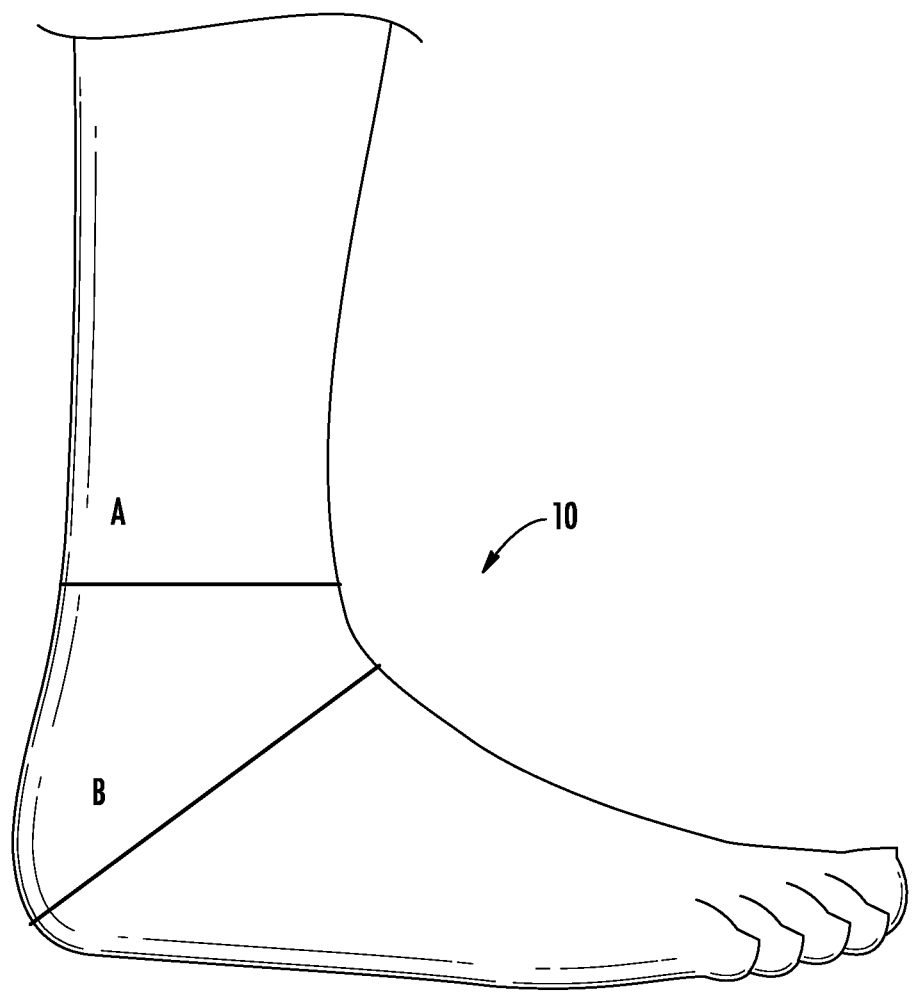
Figure 2:
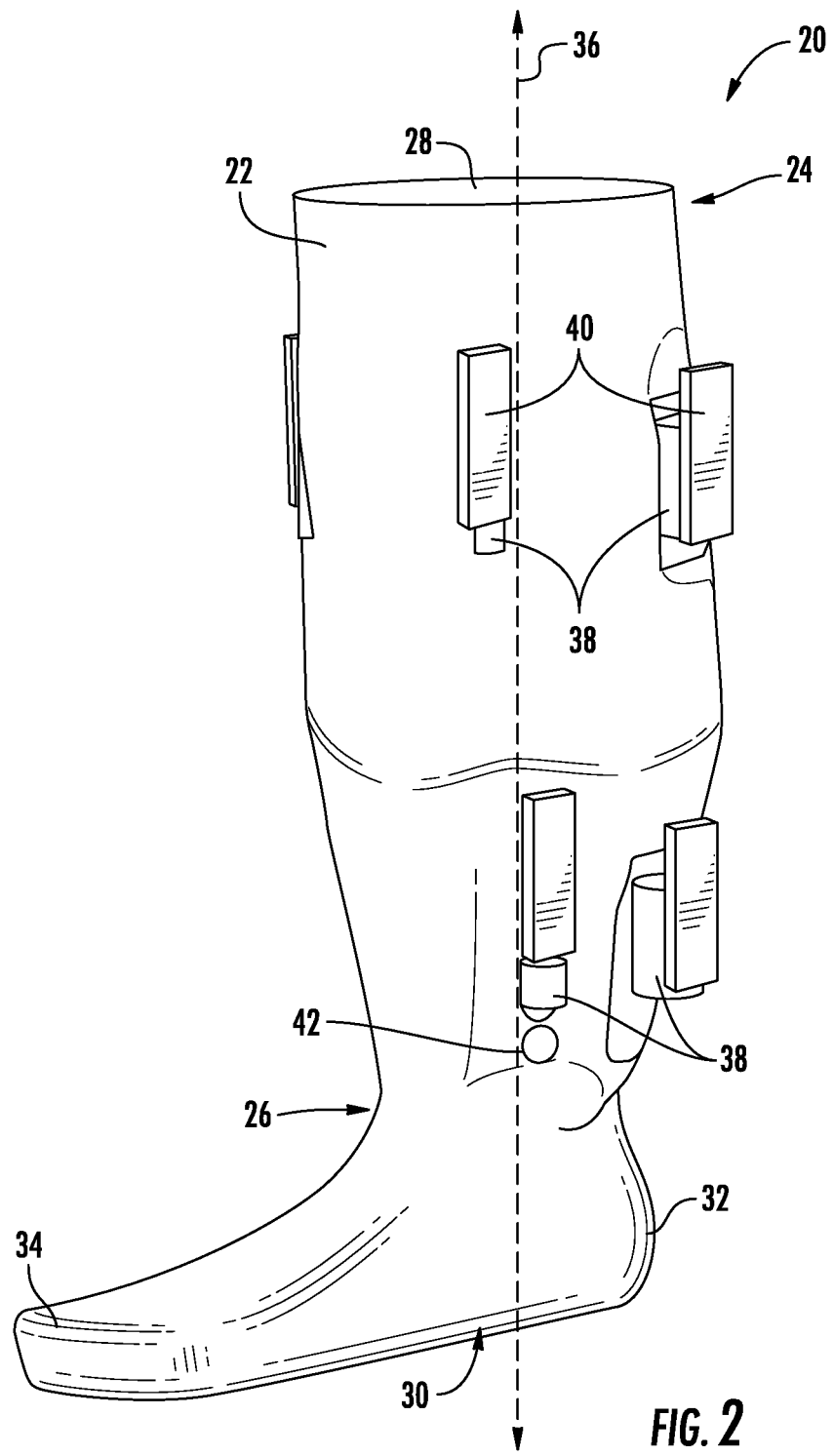
Figure 3:
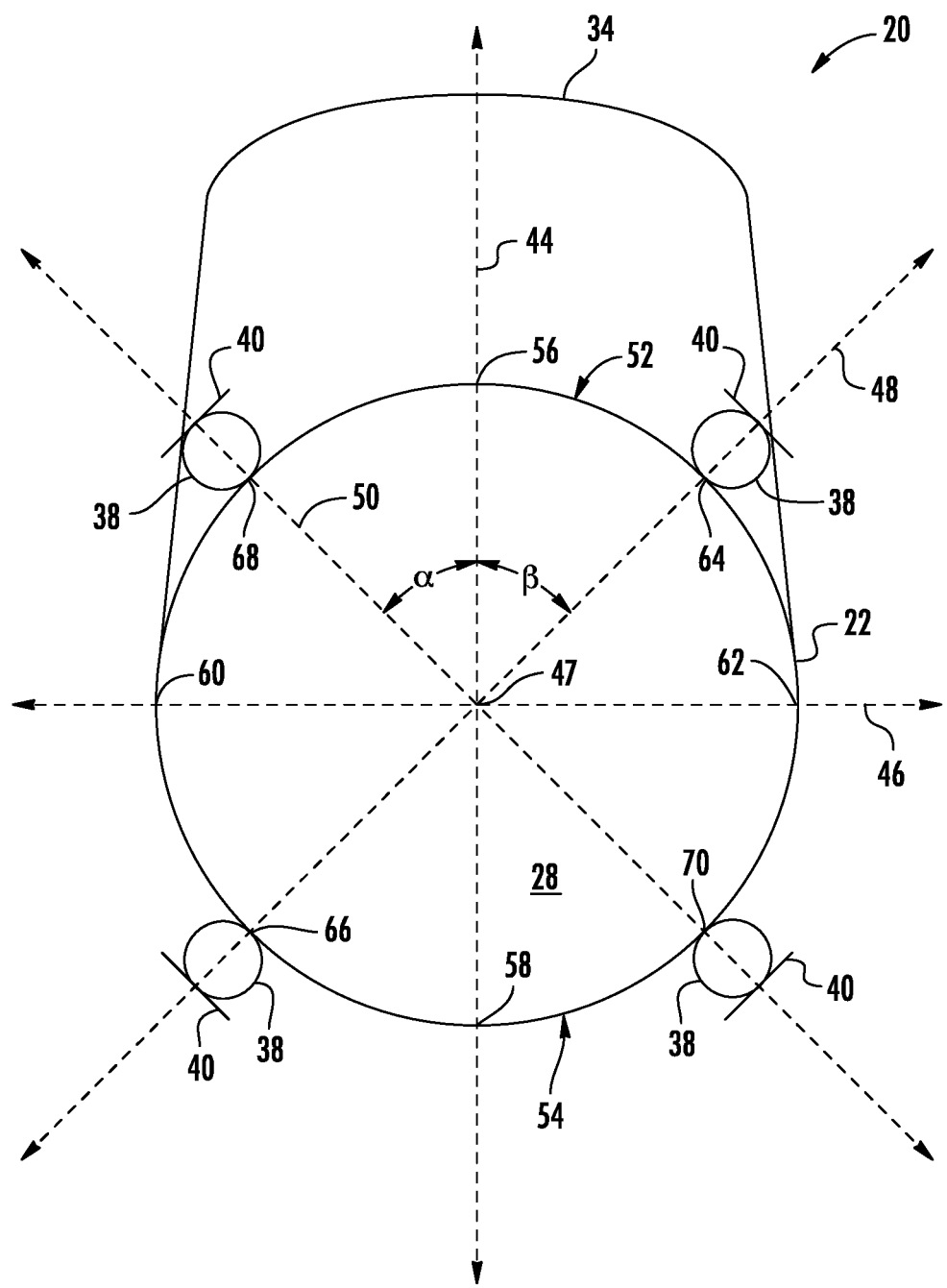
Figure 4:
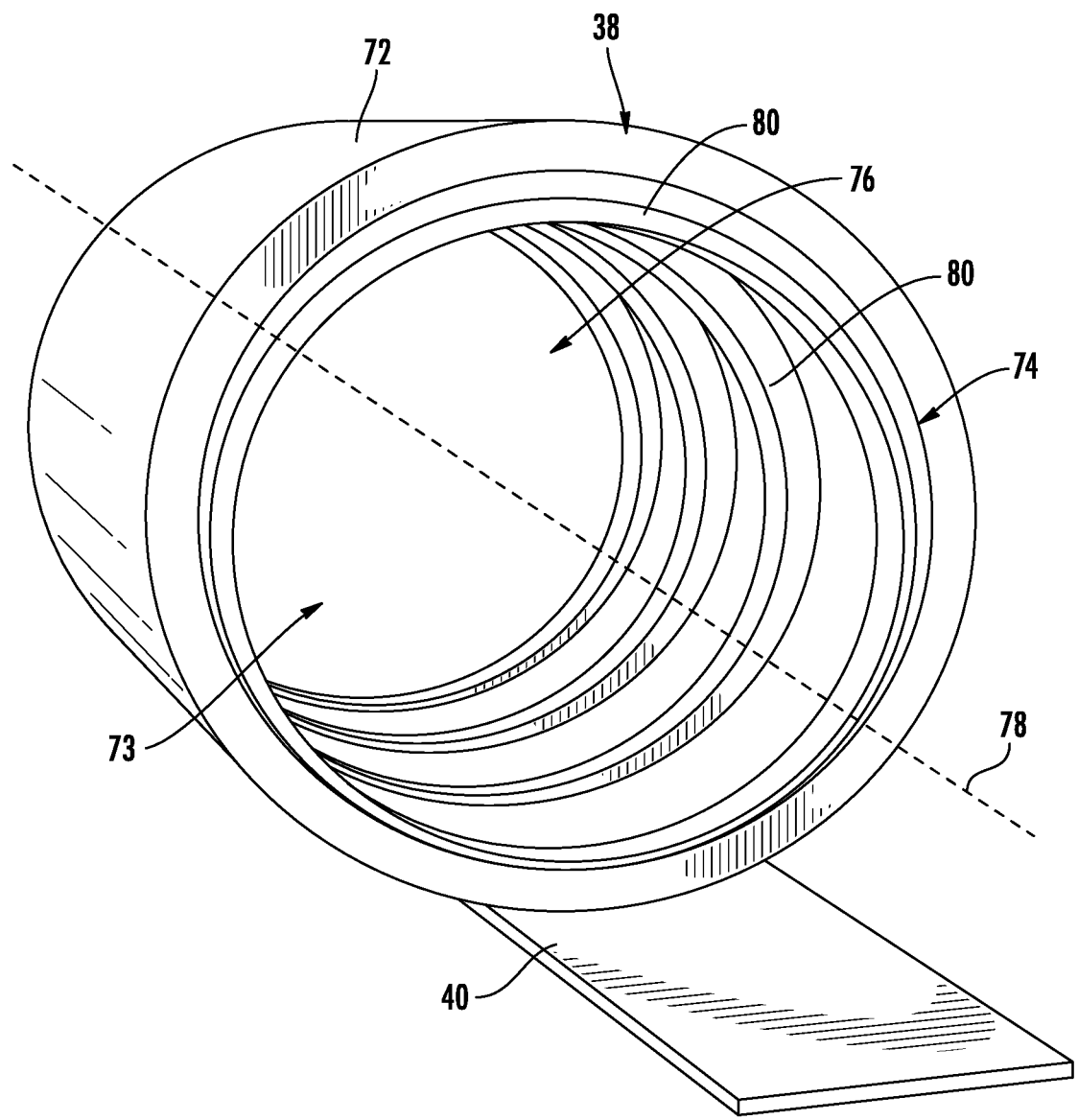
Figure 5:
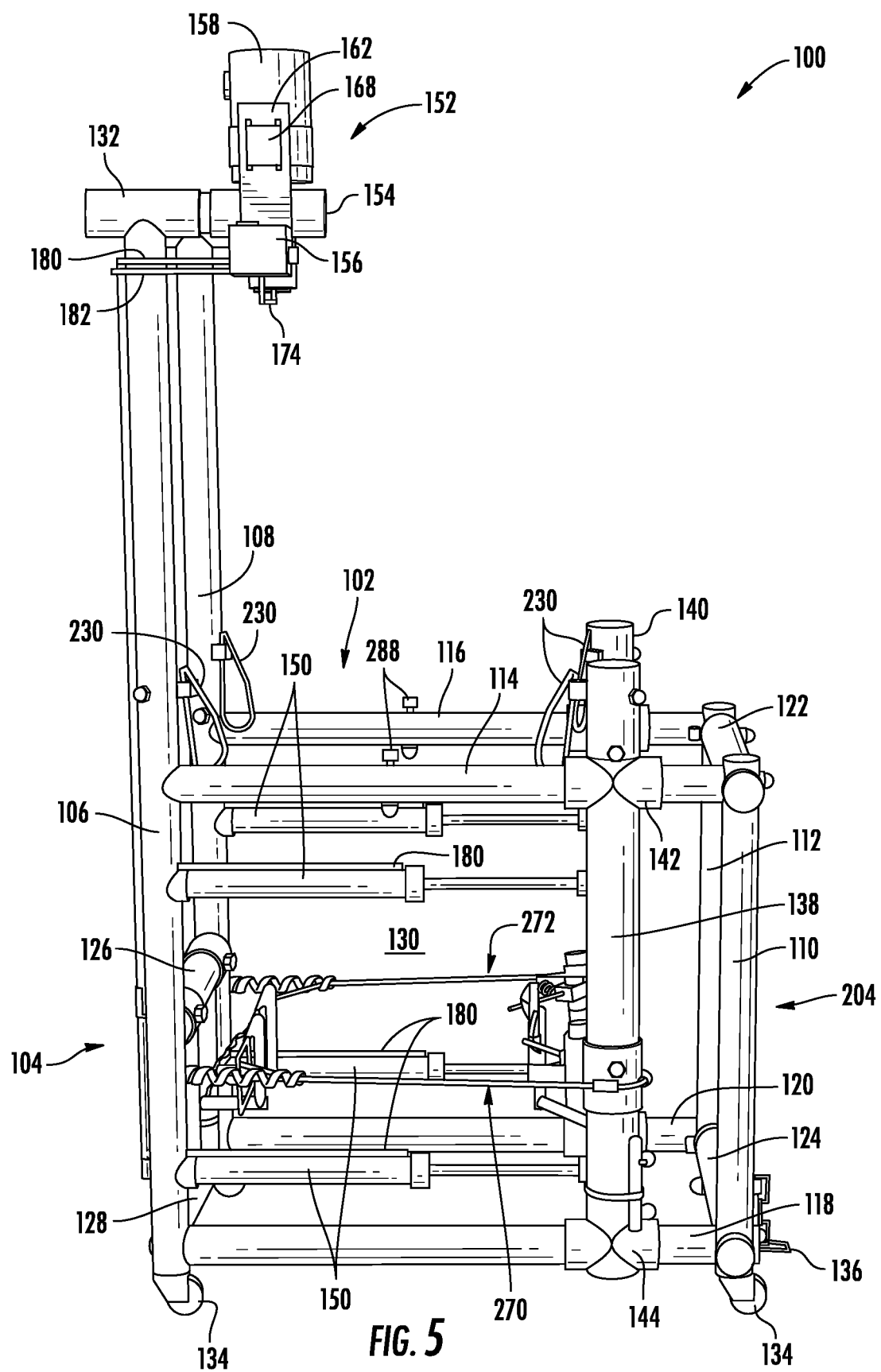
Figure 6:
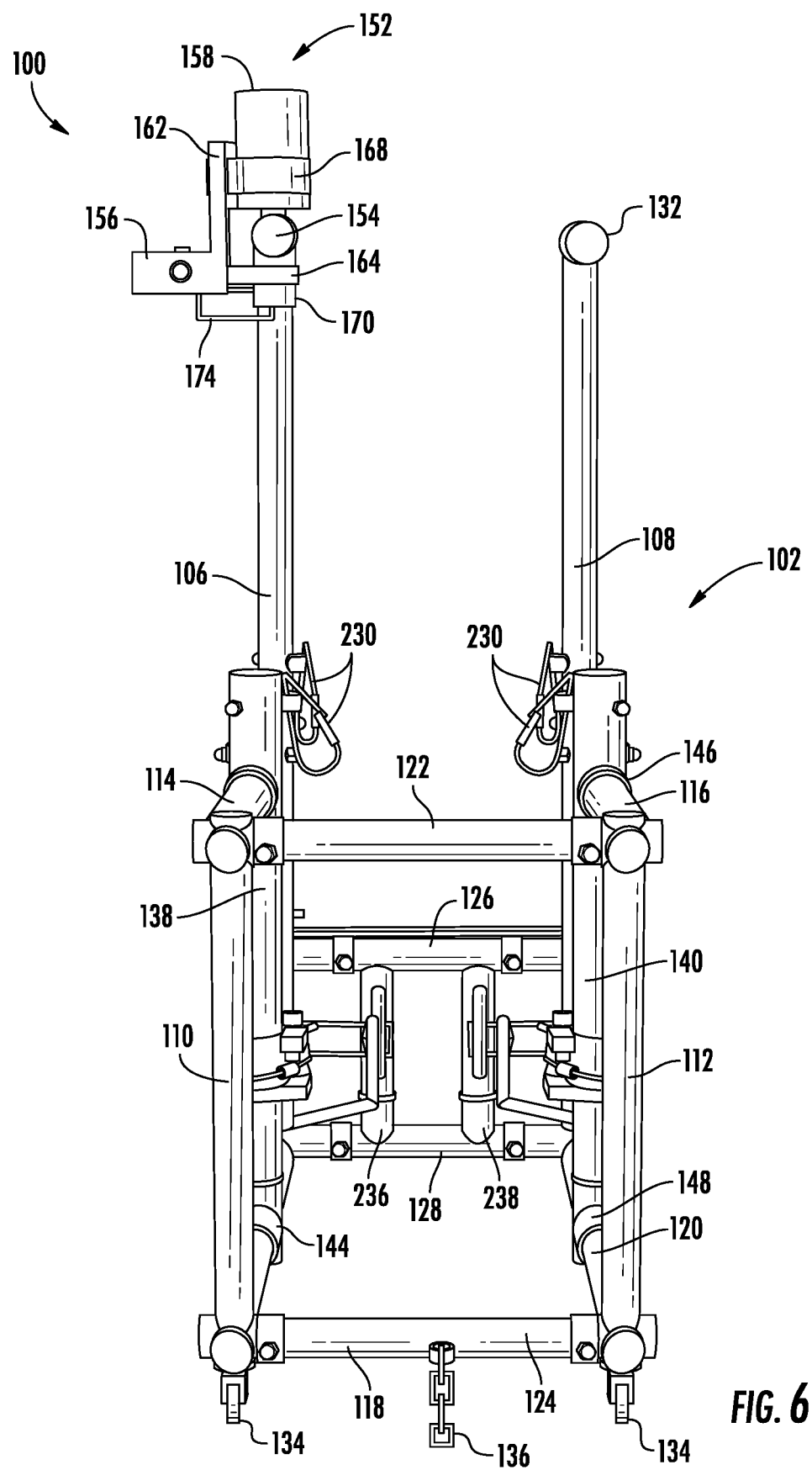
Figure 7:
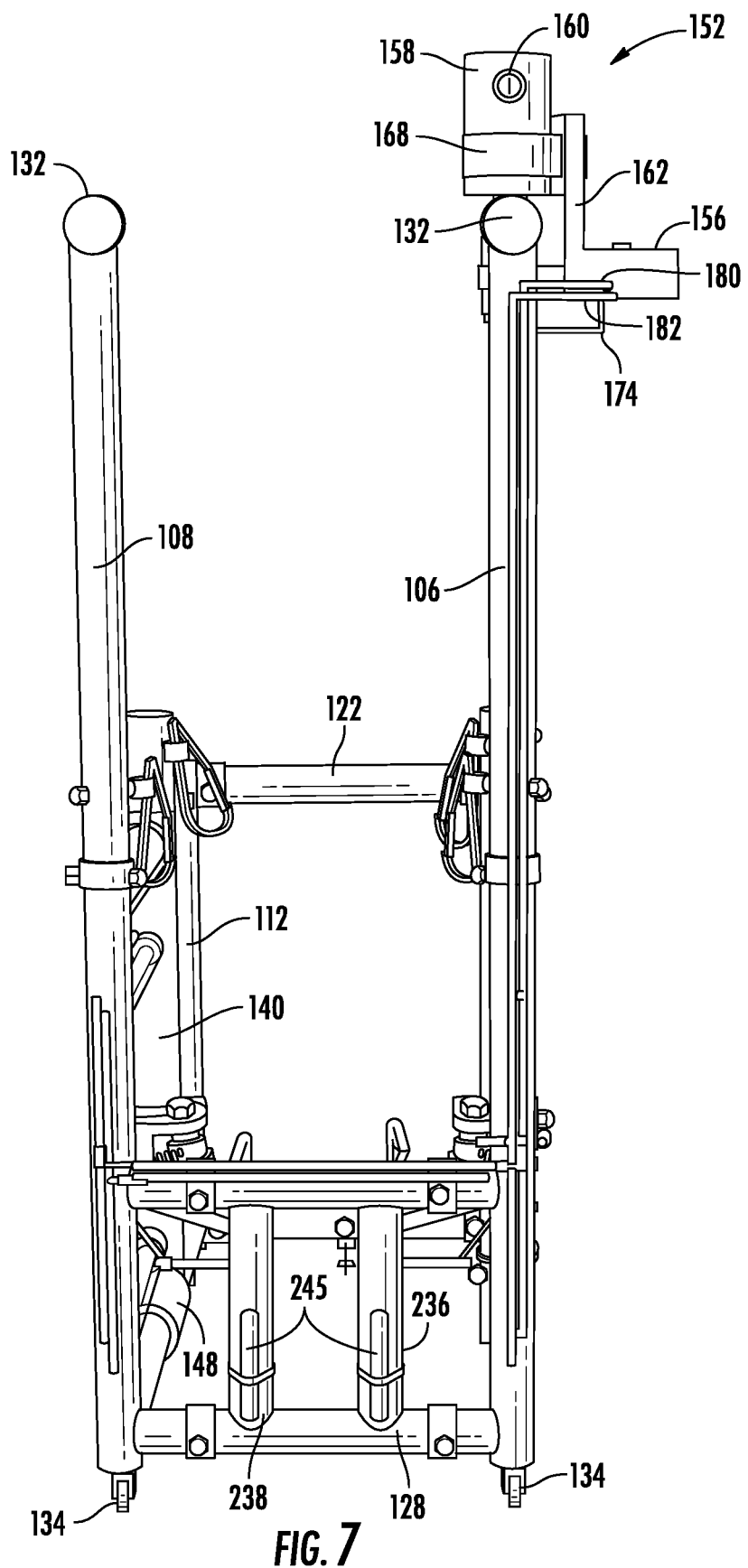
Figure 8:
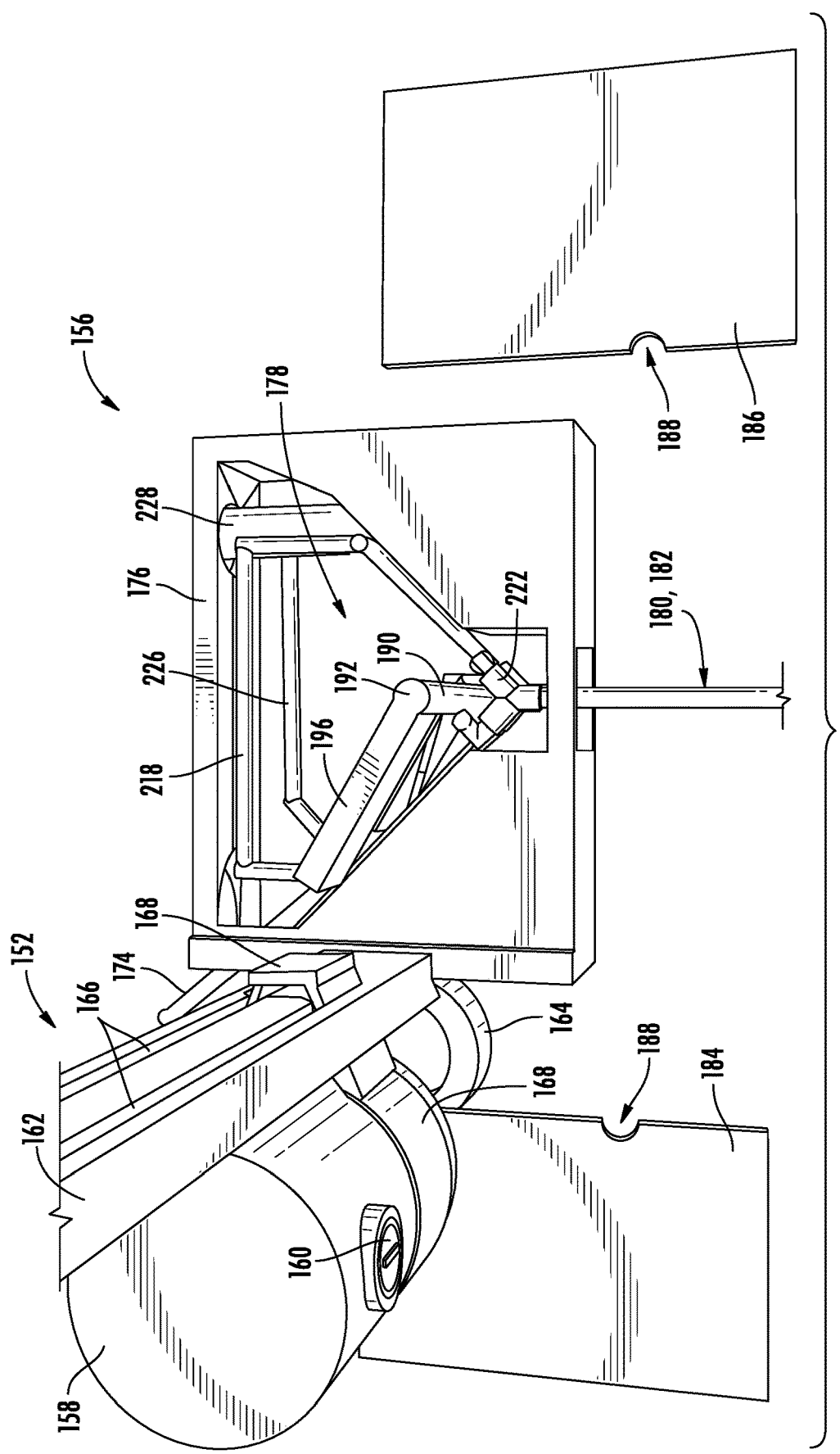
Figure 9:
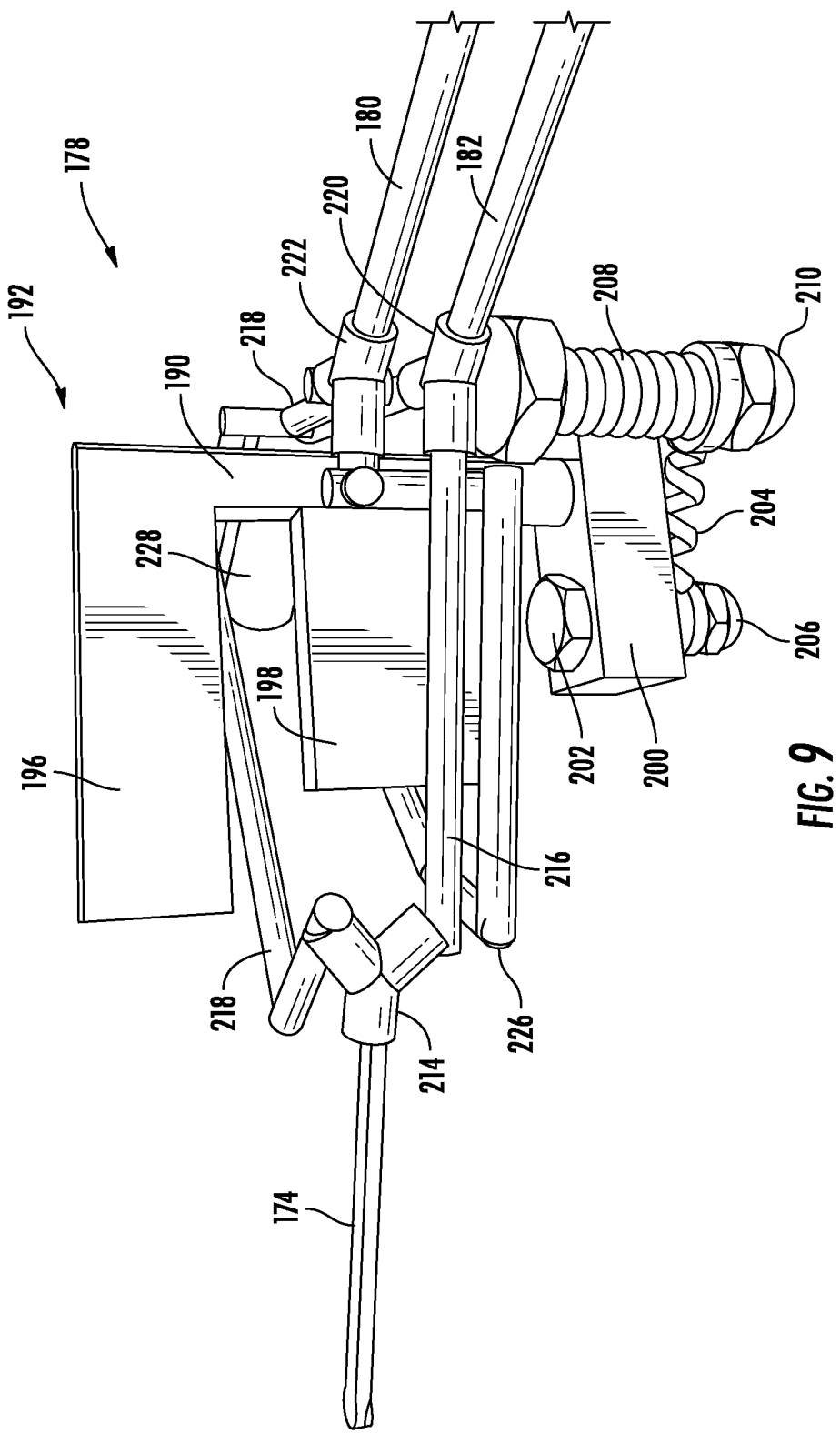
Figure 10:
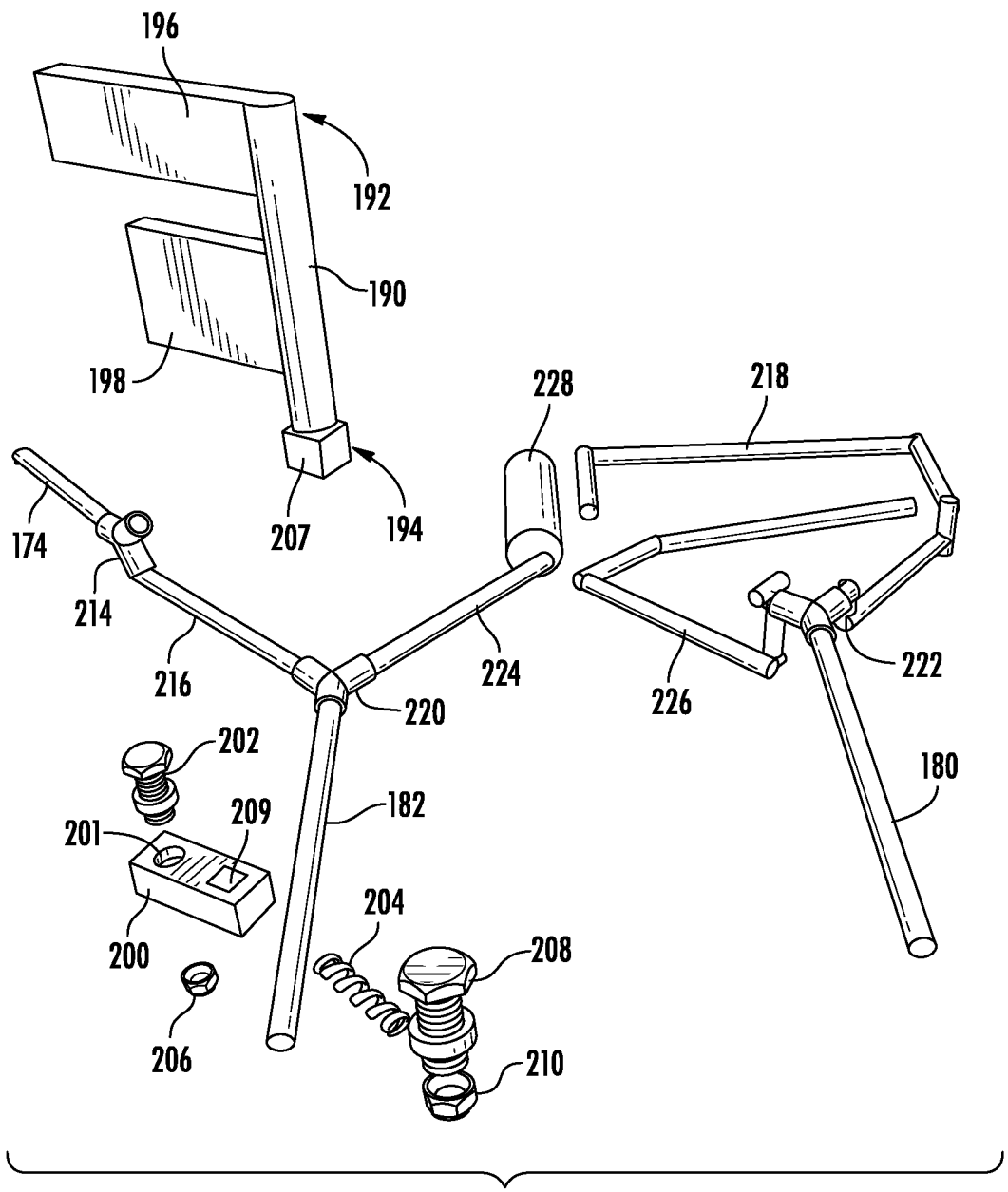
Figure 11:
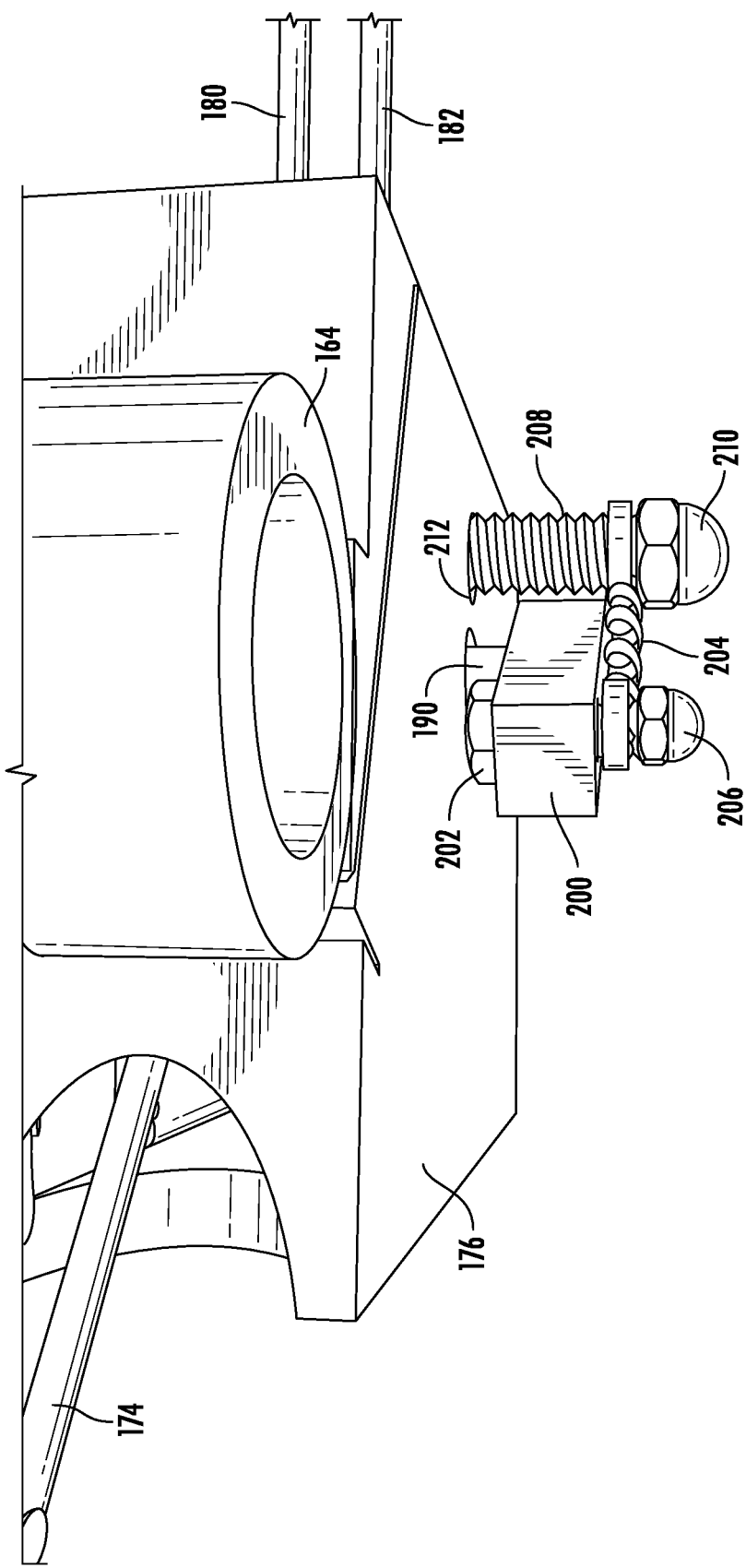
Figure 12:
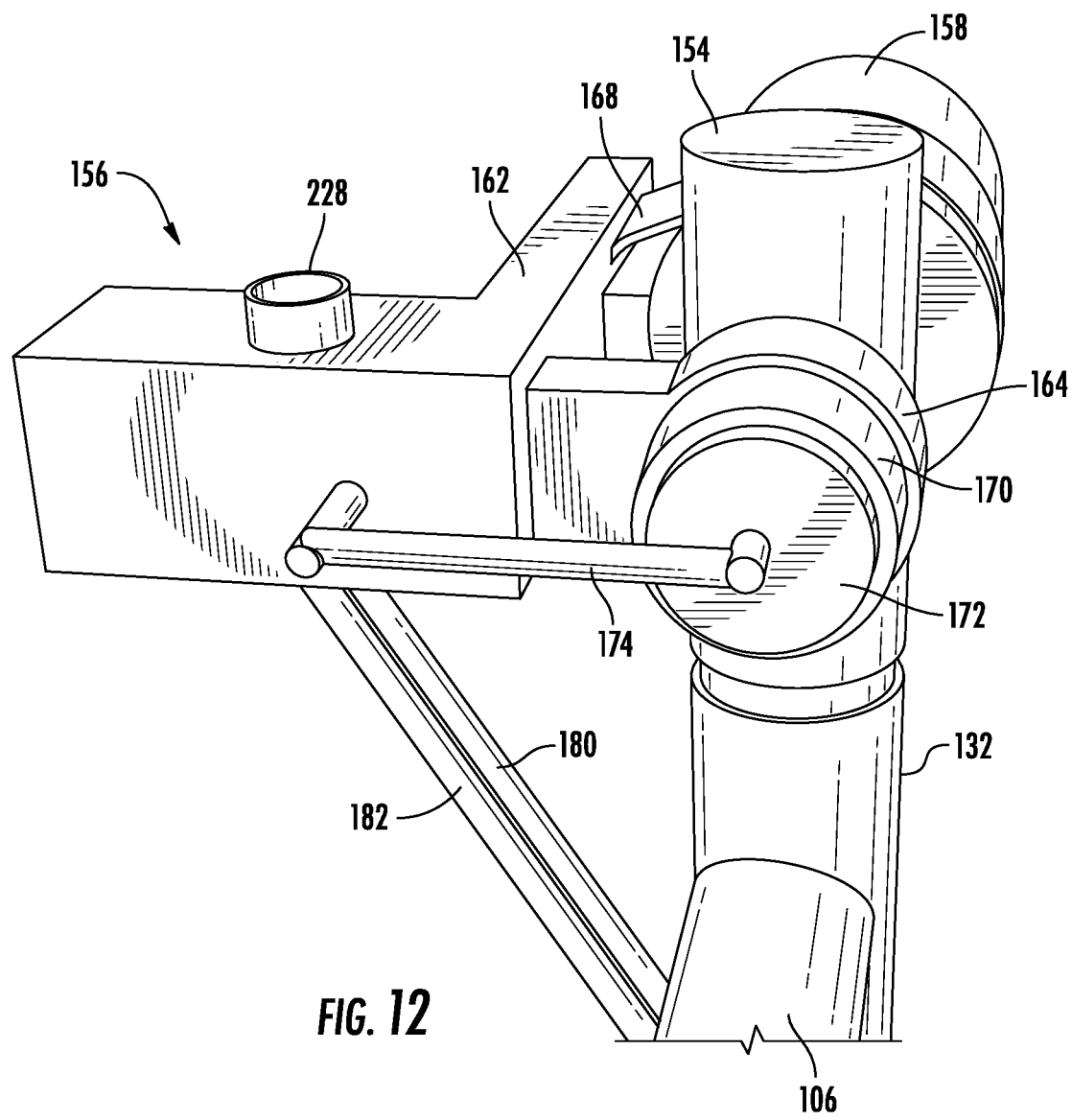
Figure 13:
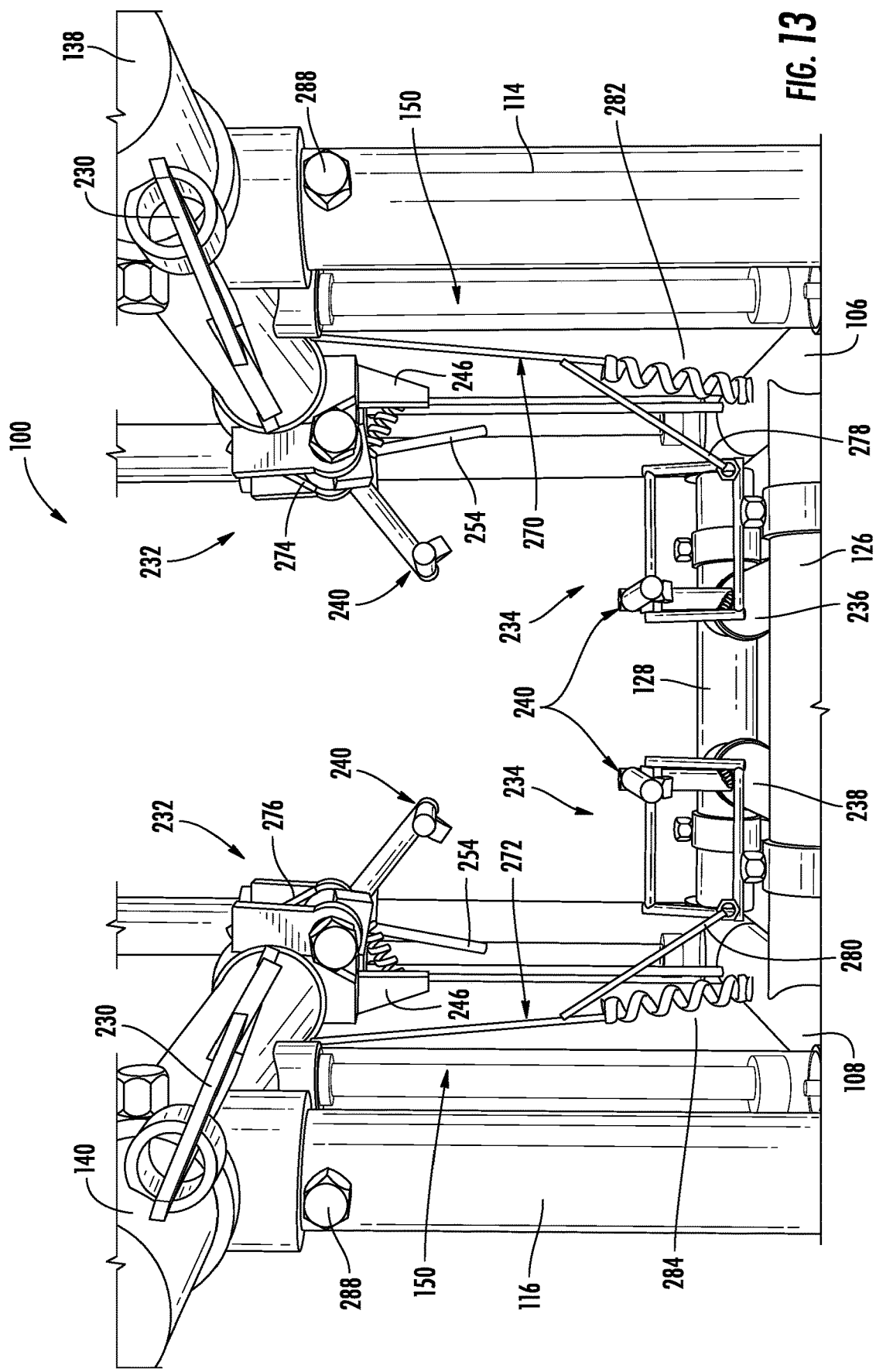
Figure 14:
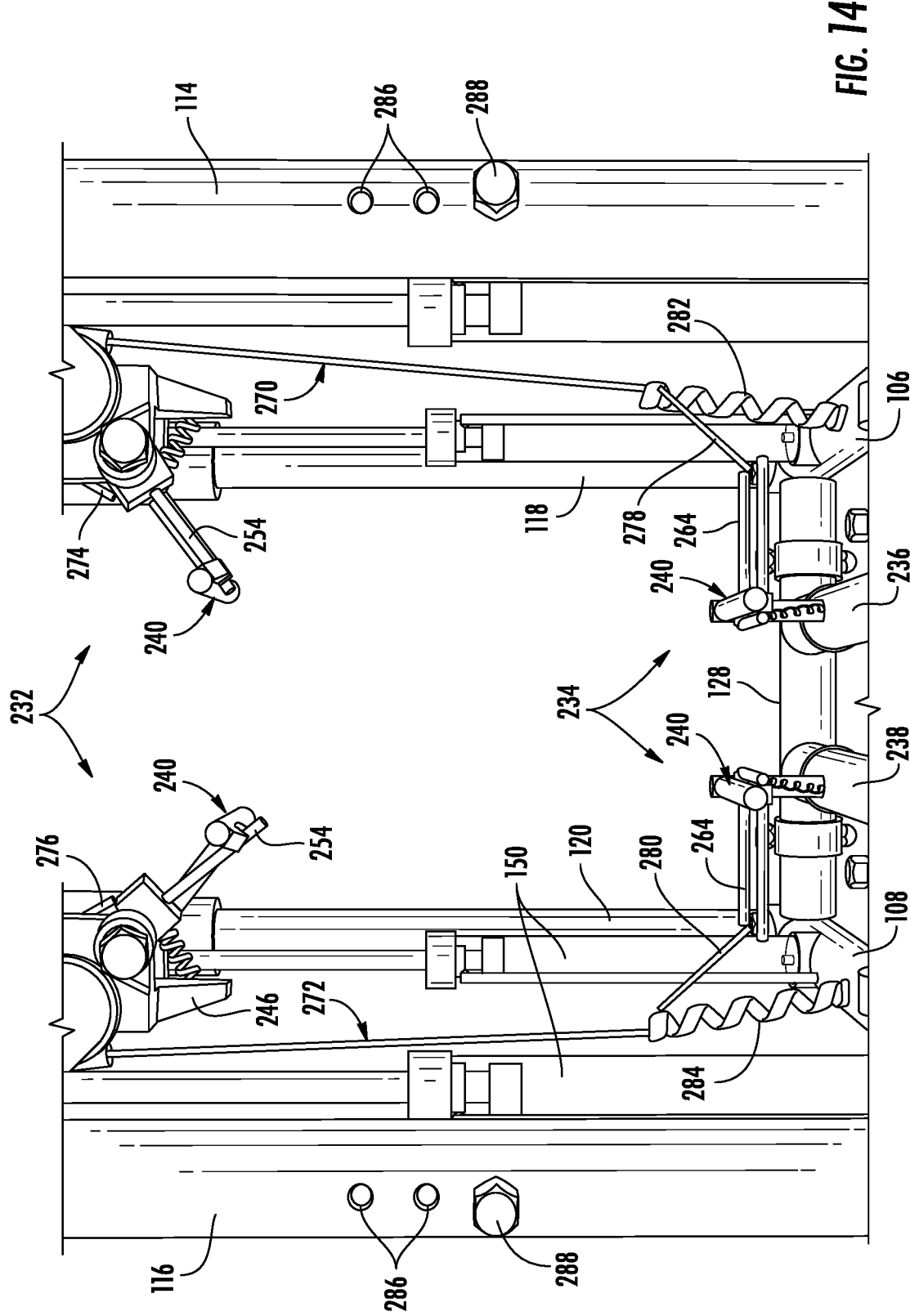
Figure 15:
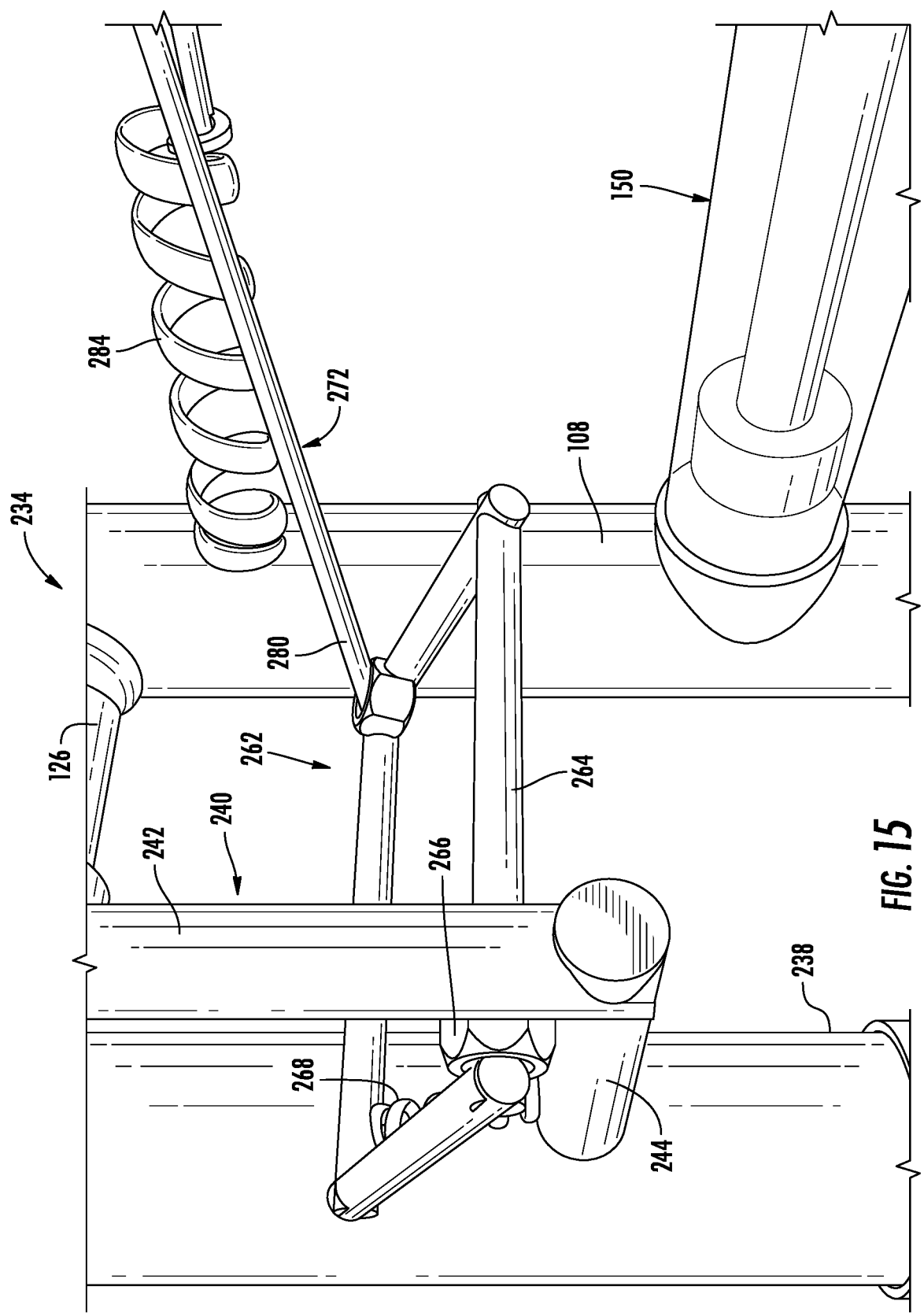
Figure 16:
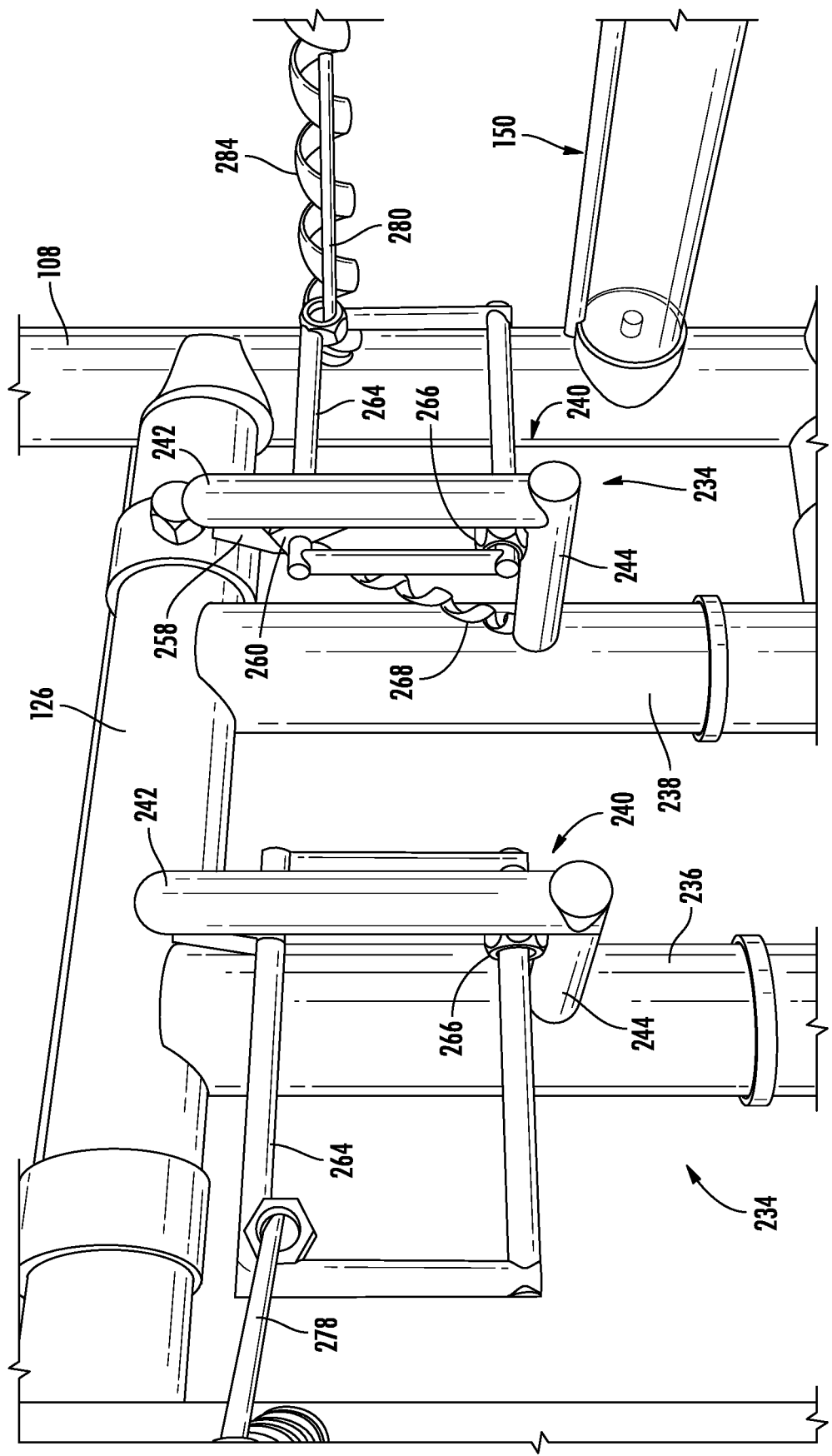
Figure 17:
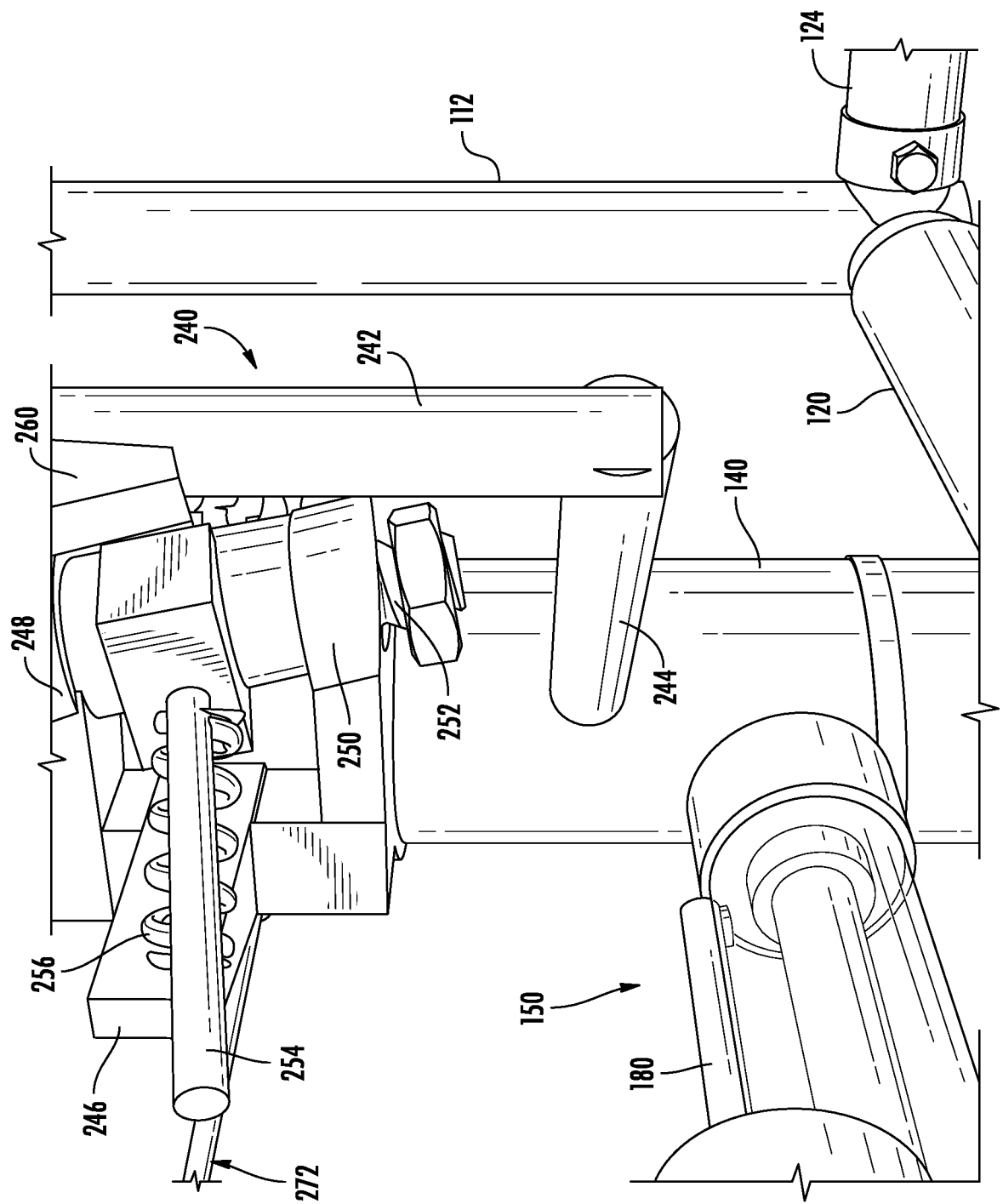
Figure 18:
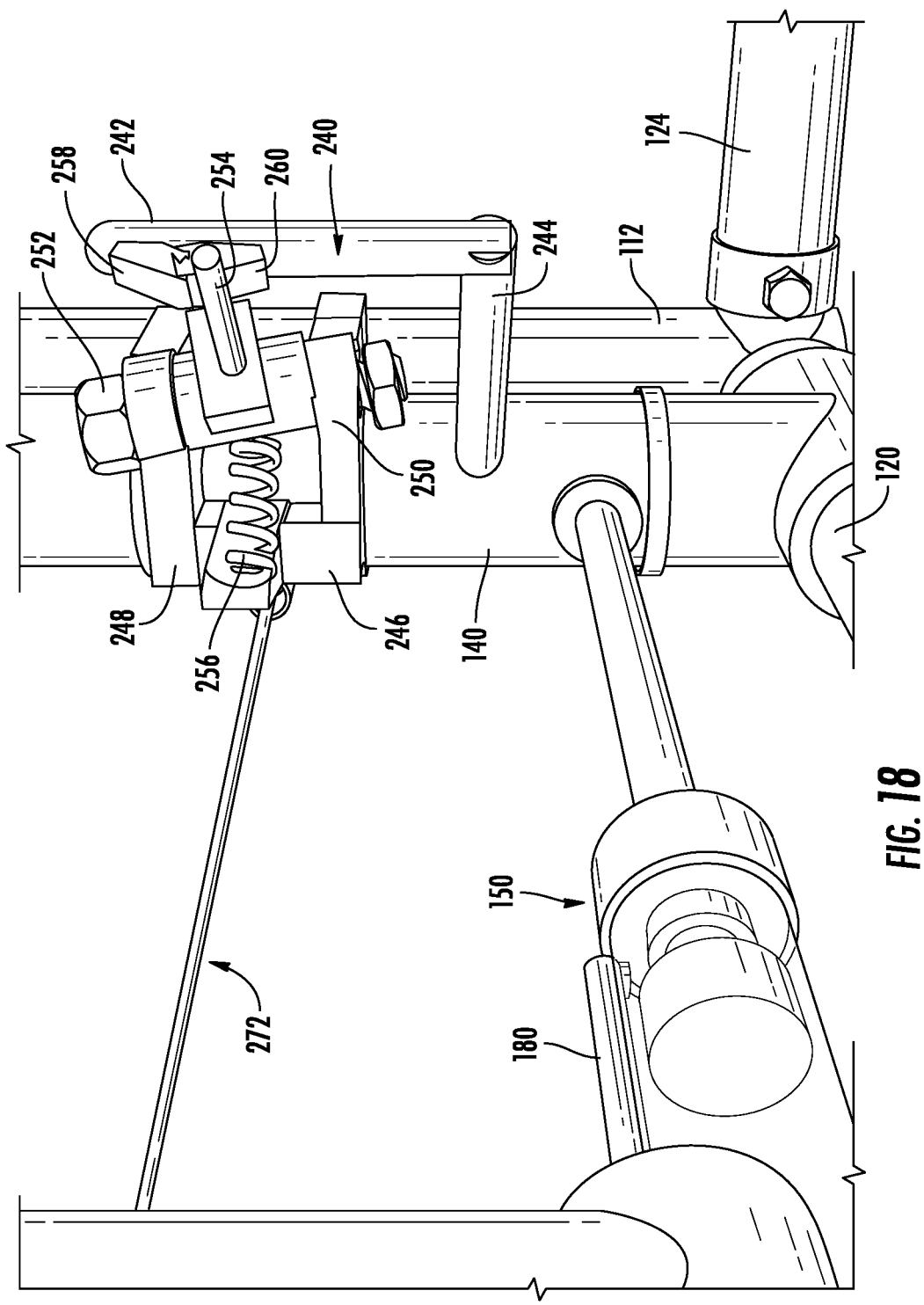
Figure 19:
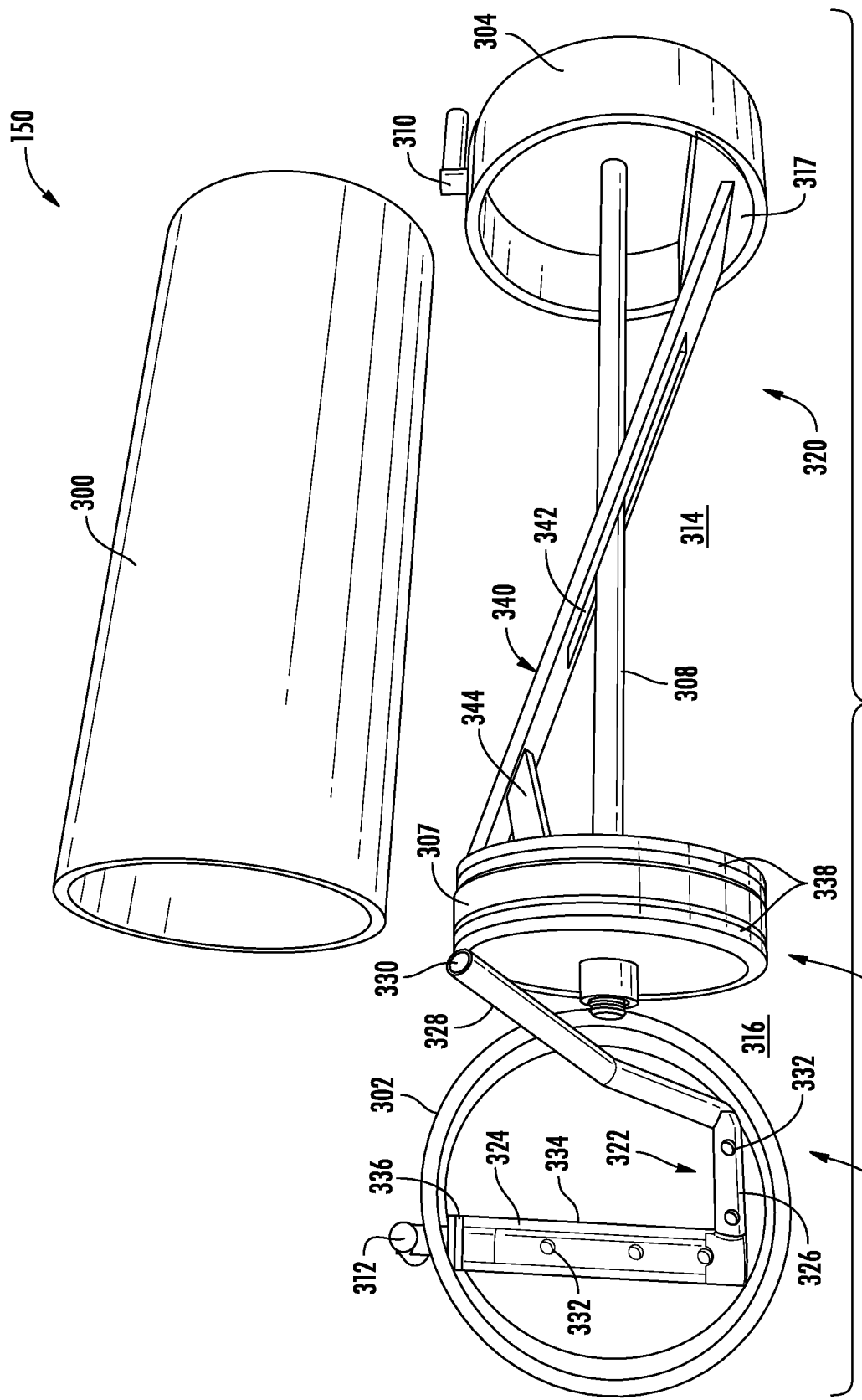
Figure 20:
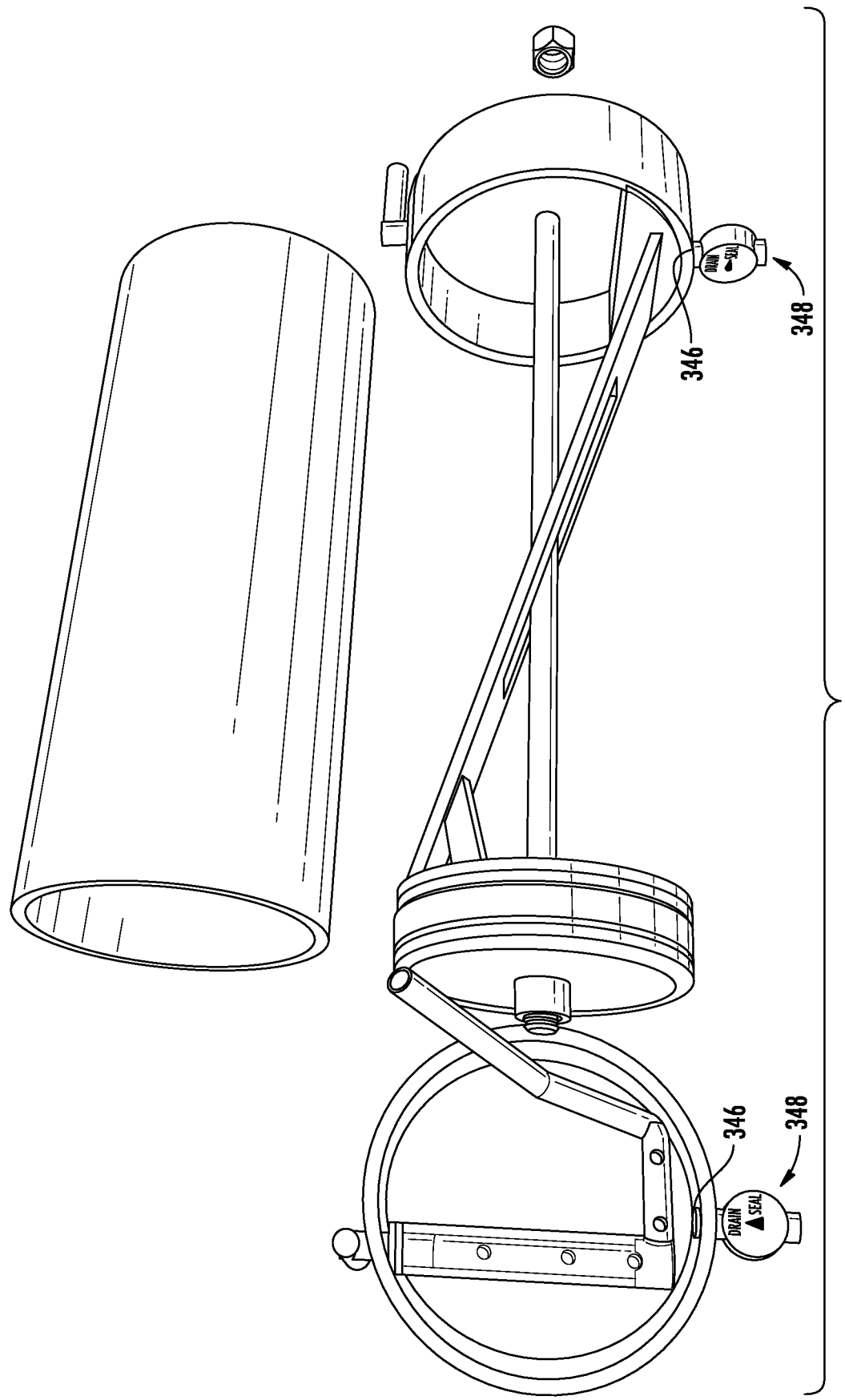
Figure 21:
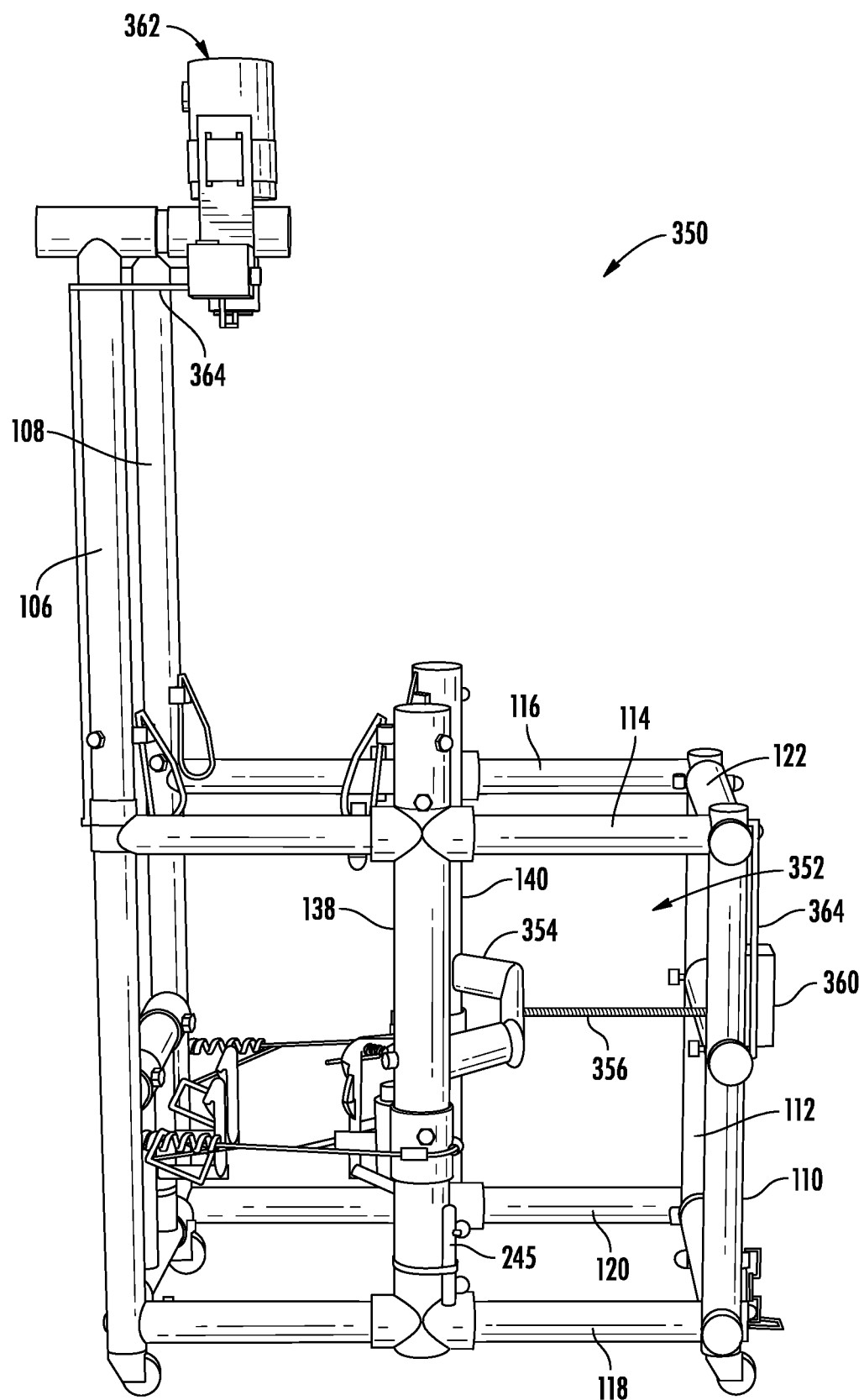
Figure 22:
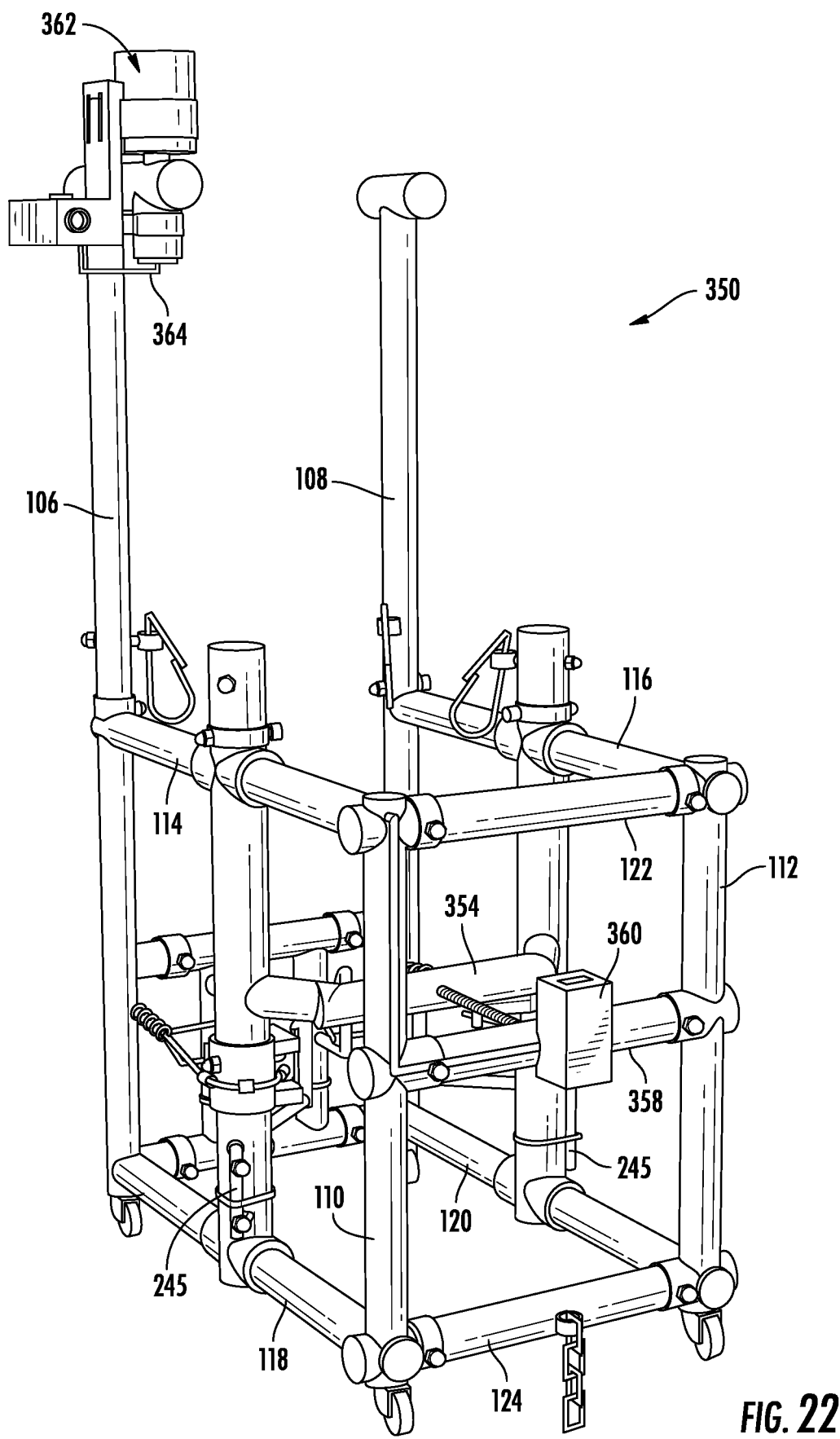
Figure 23:
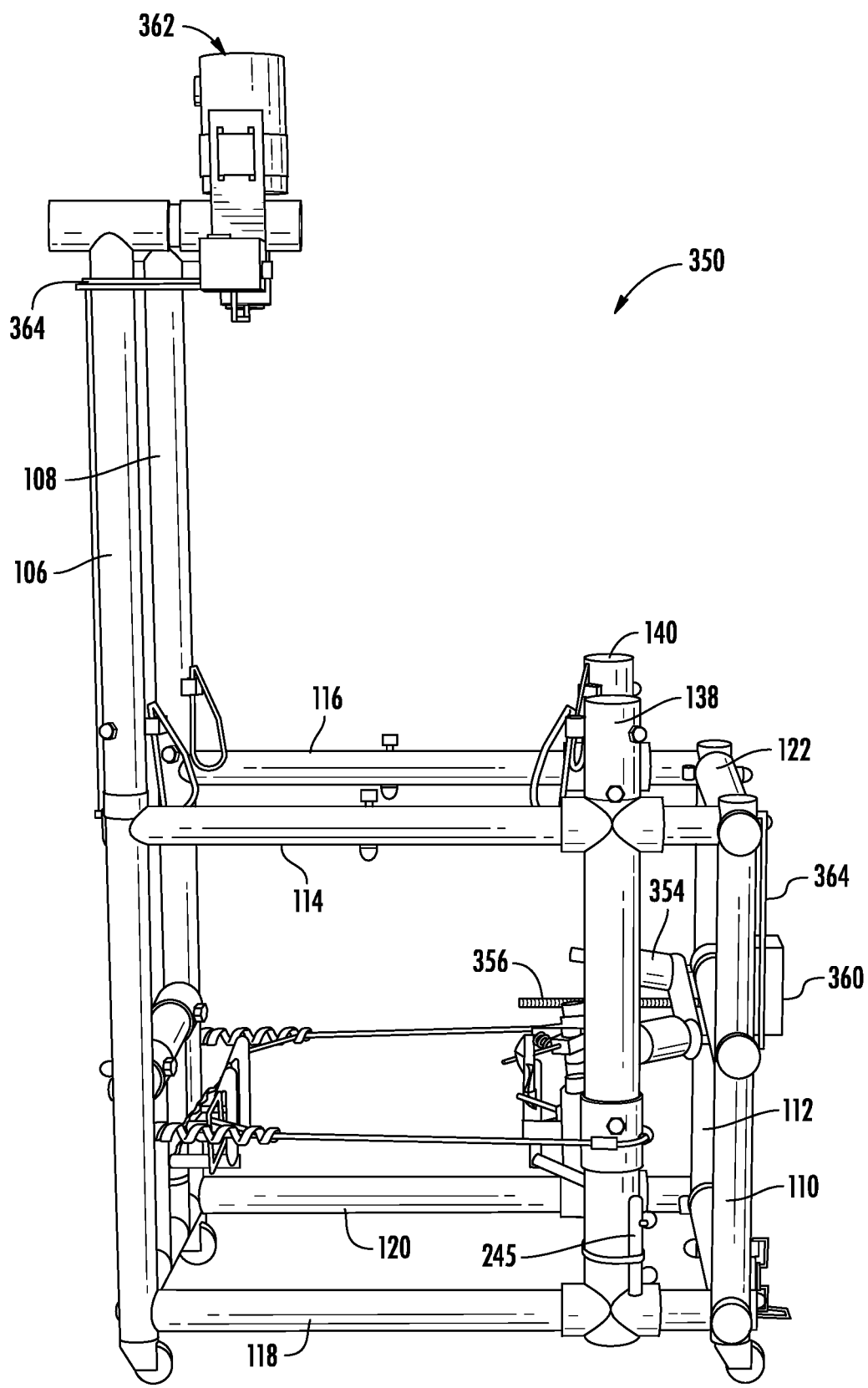
Figure 24:
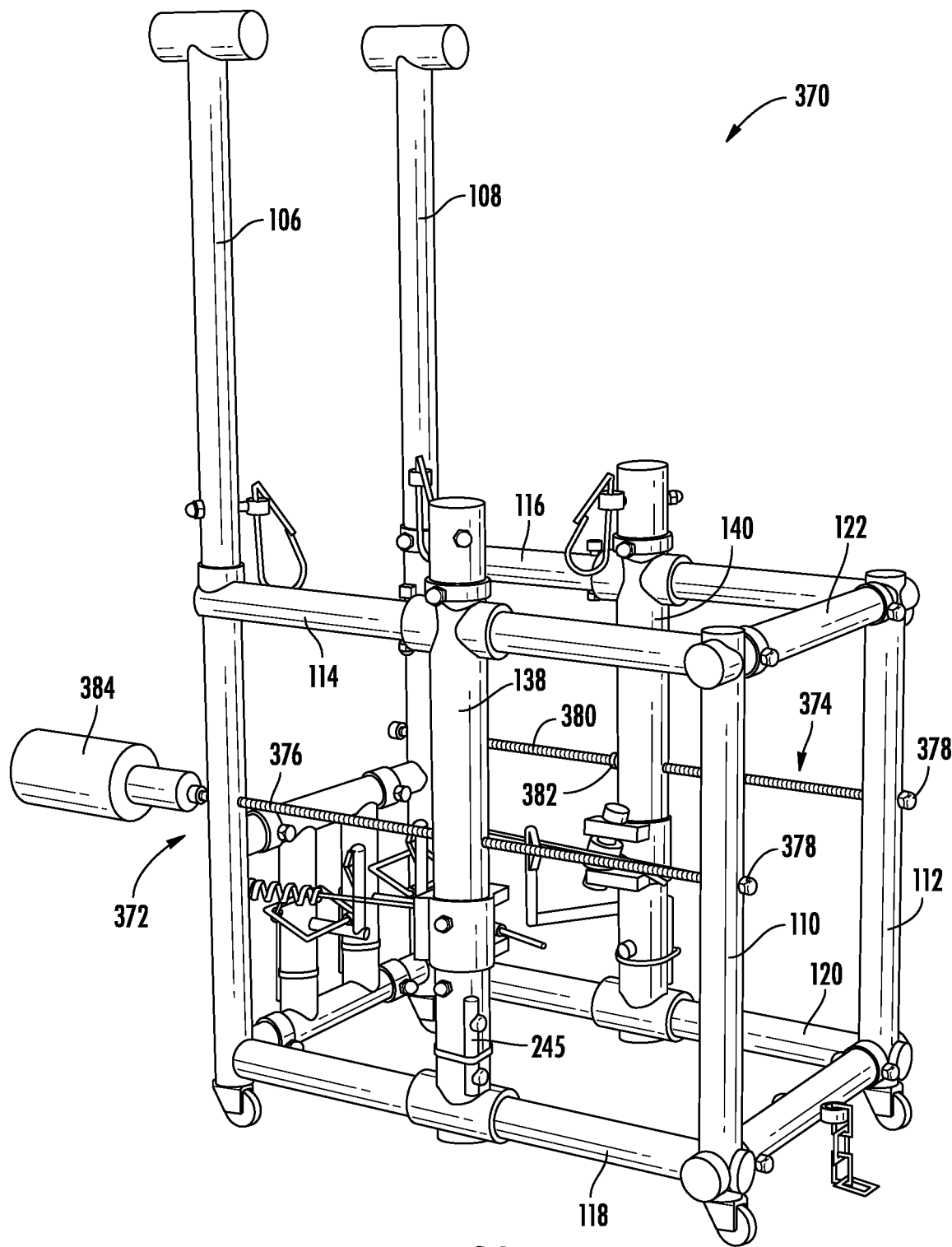
Figure 25:
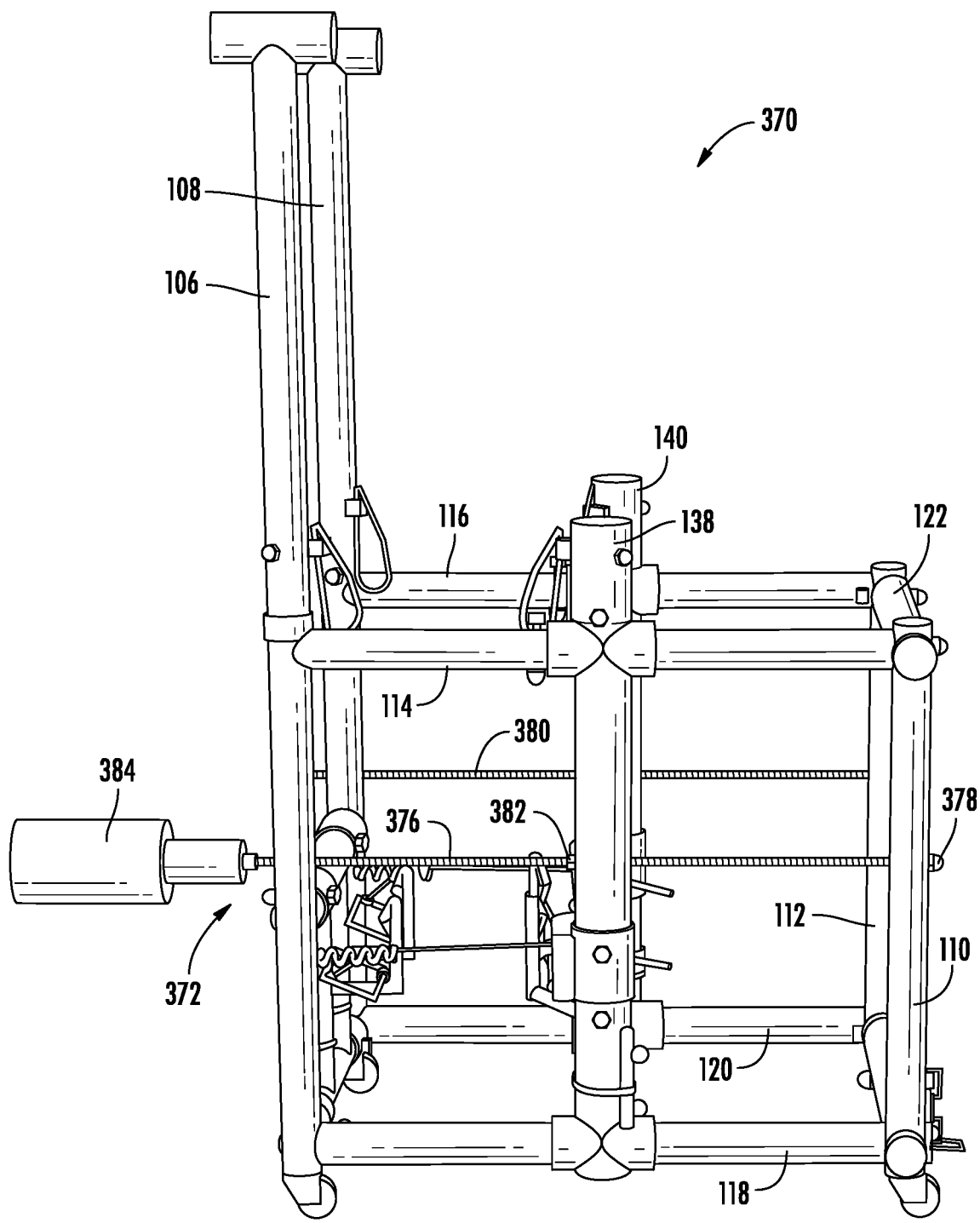
Figure 26:
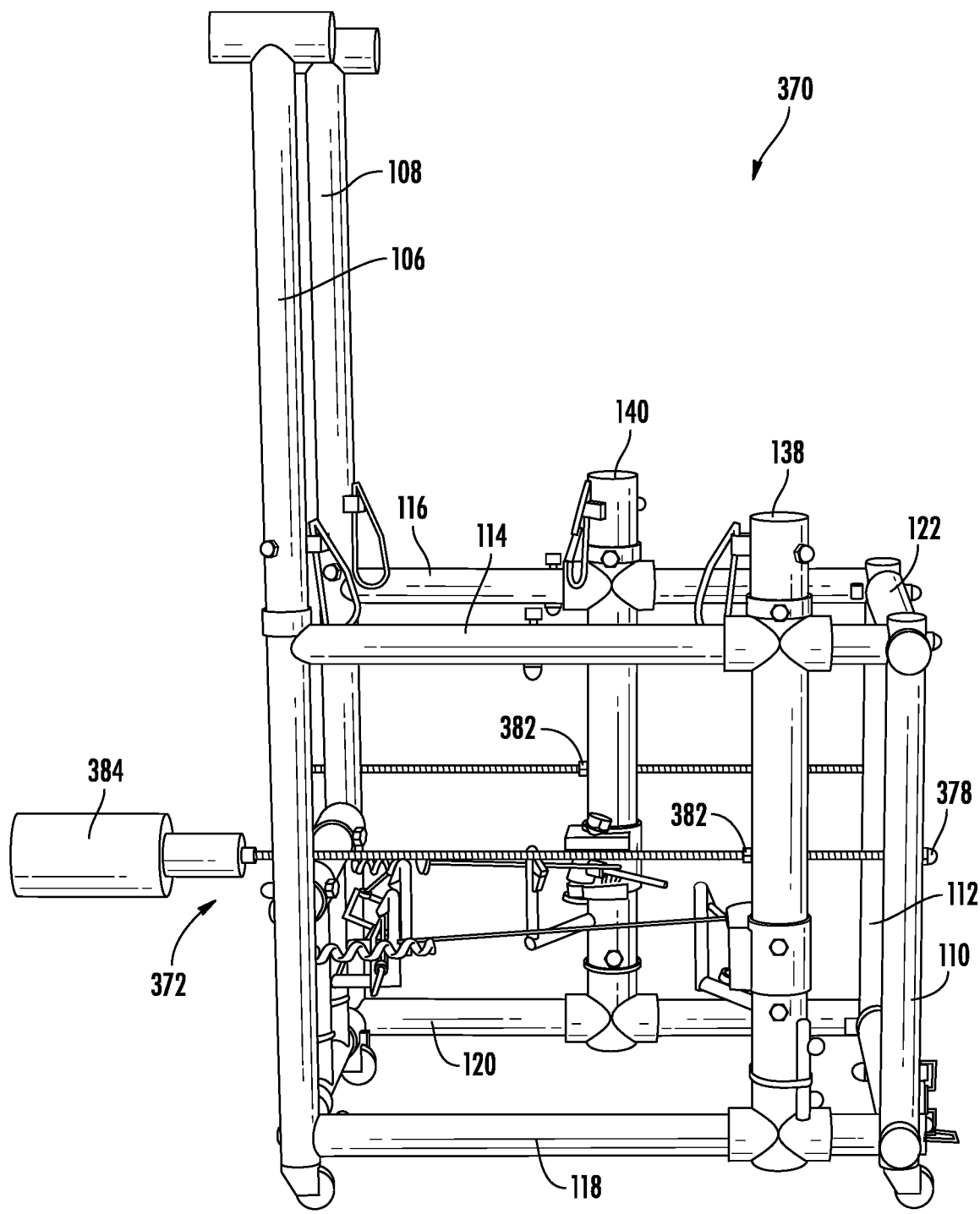
Figure 27:
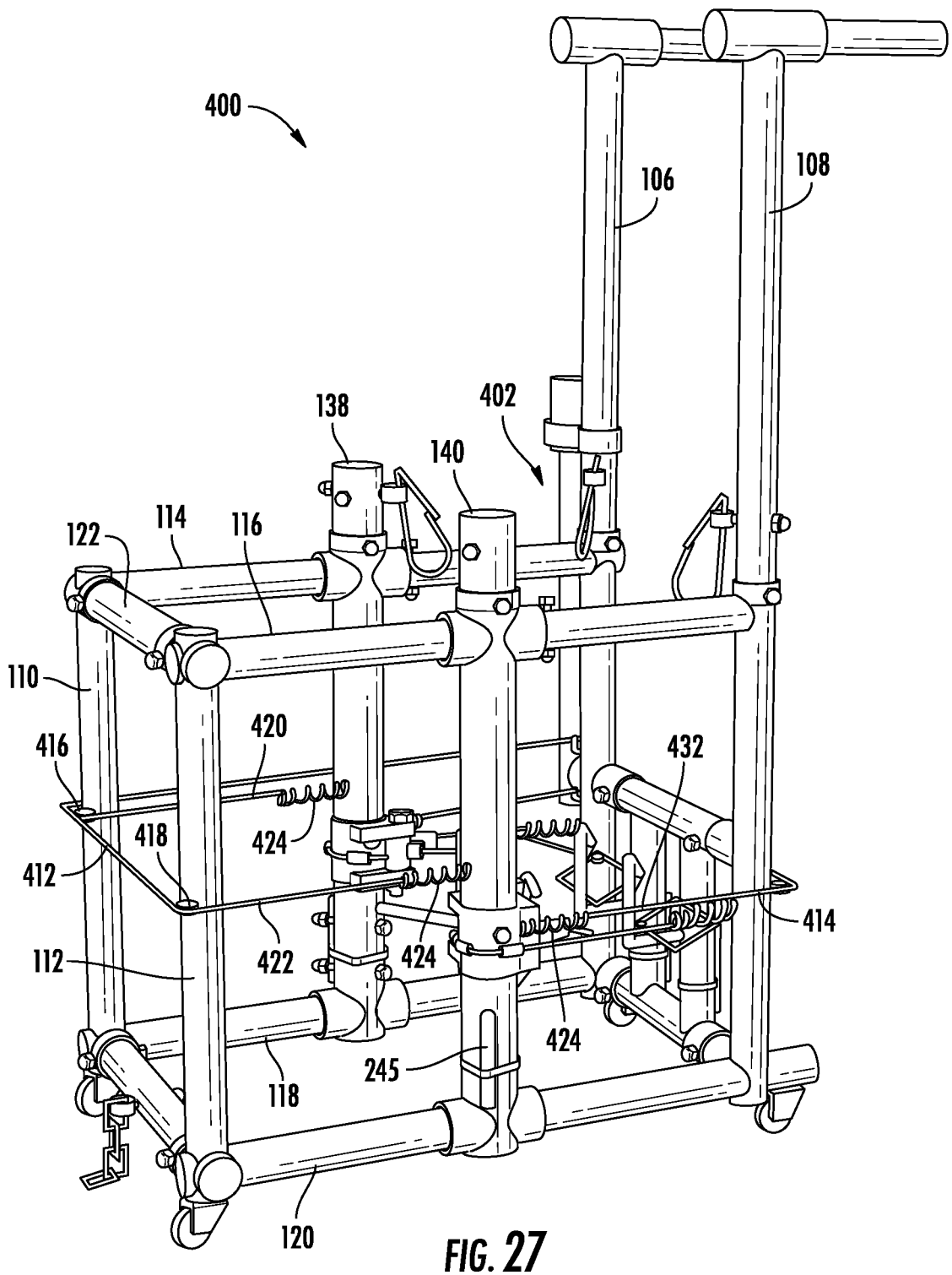
Figure 28:
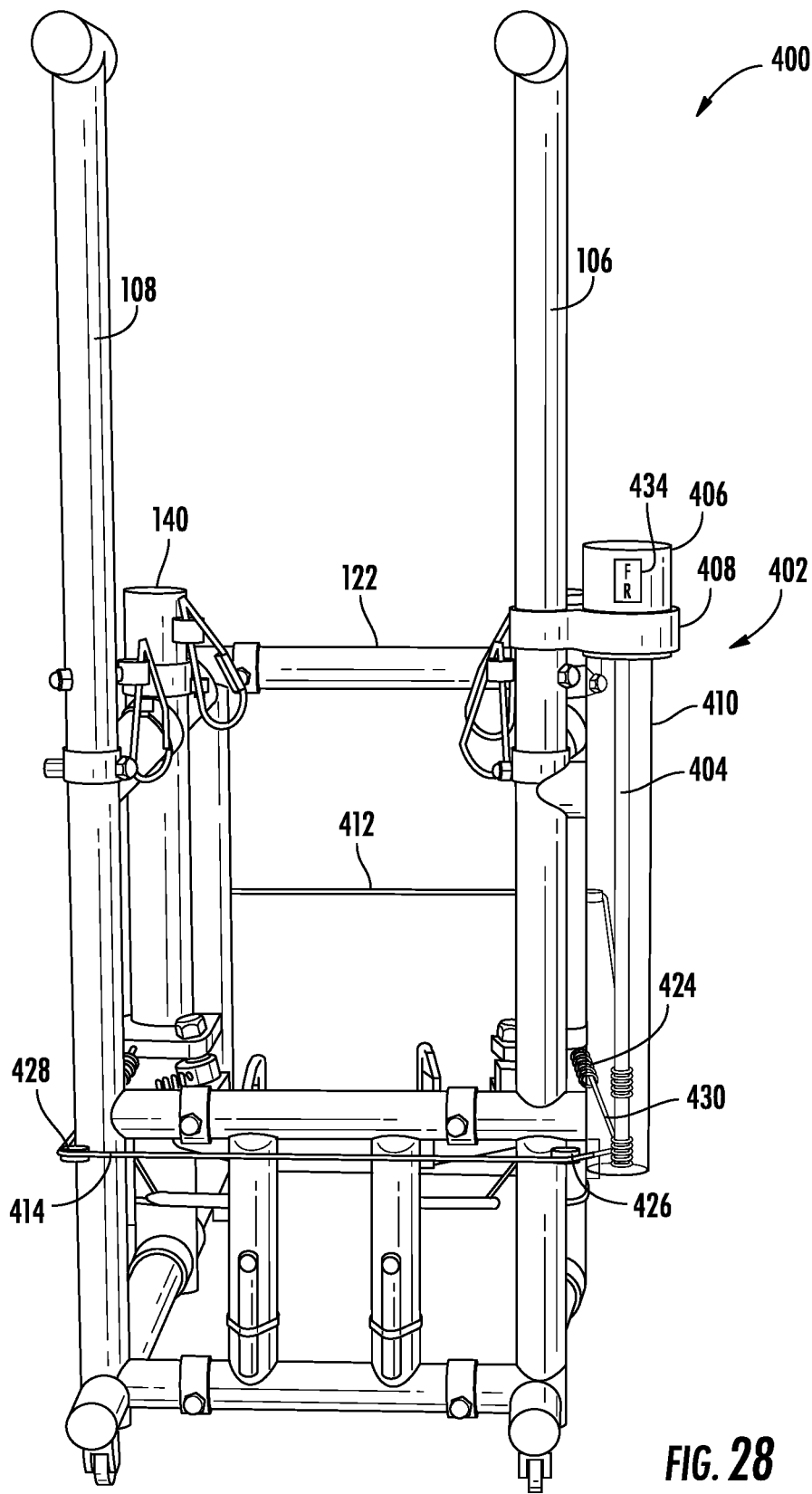
Figure 29:
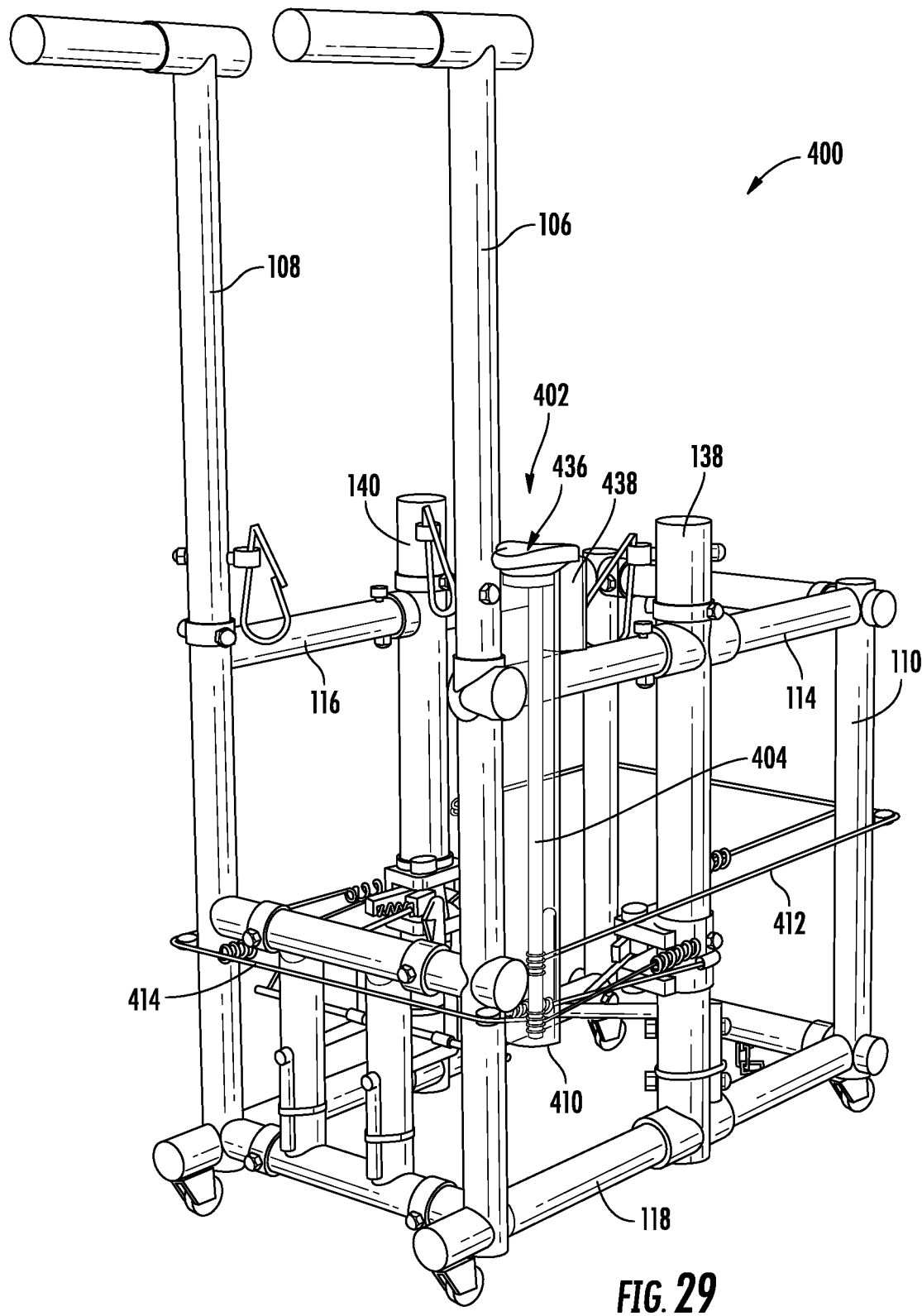
Figure 30:
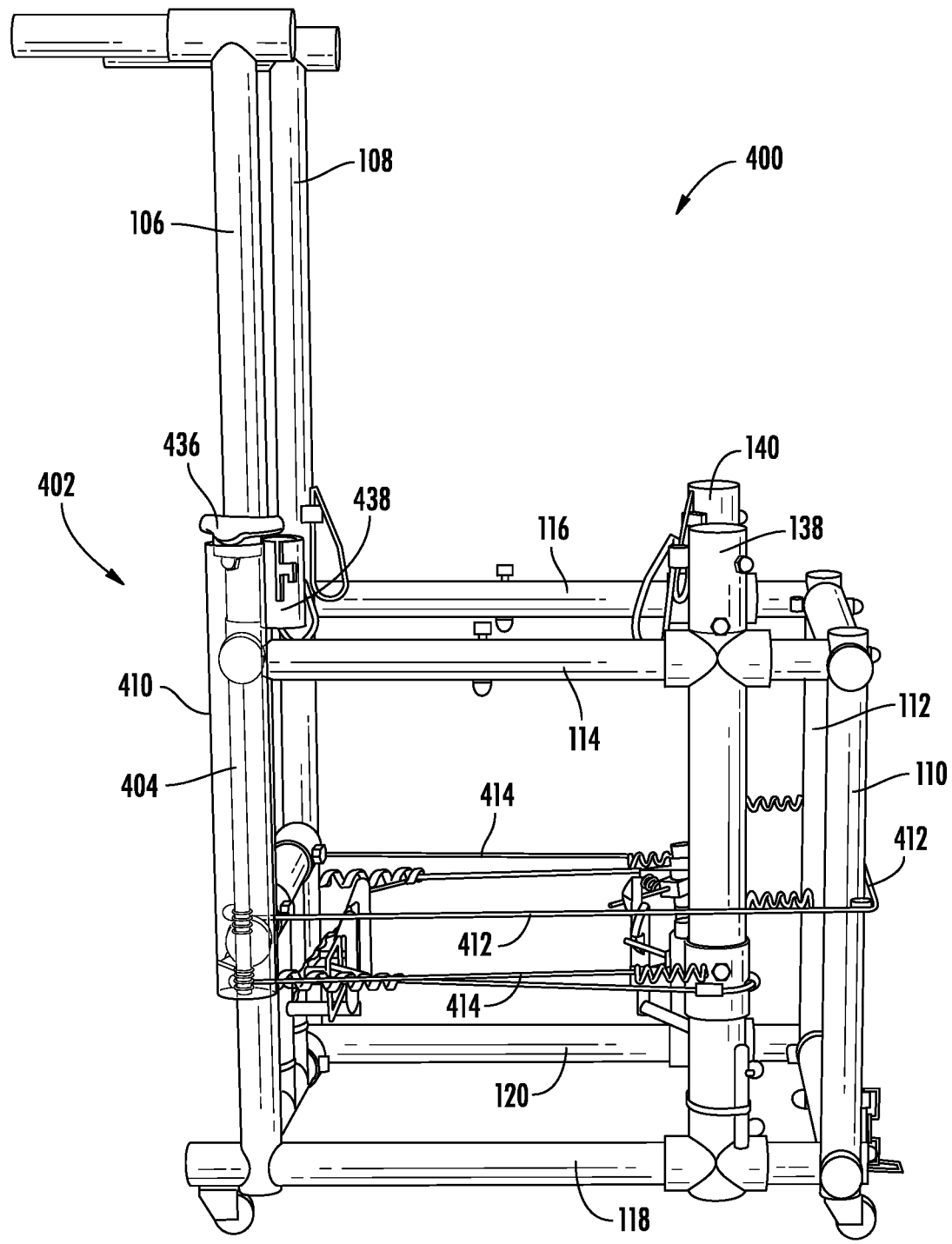
Figure 31:
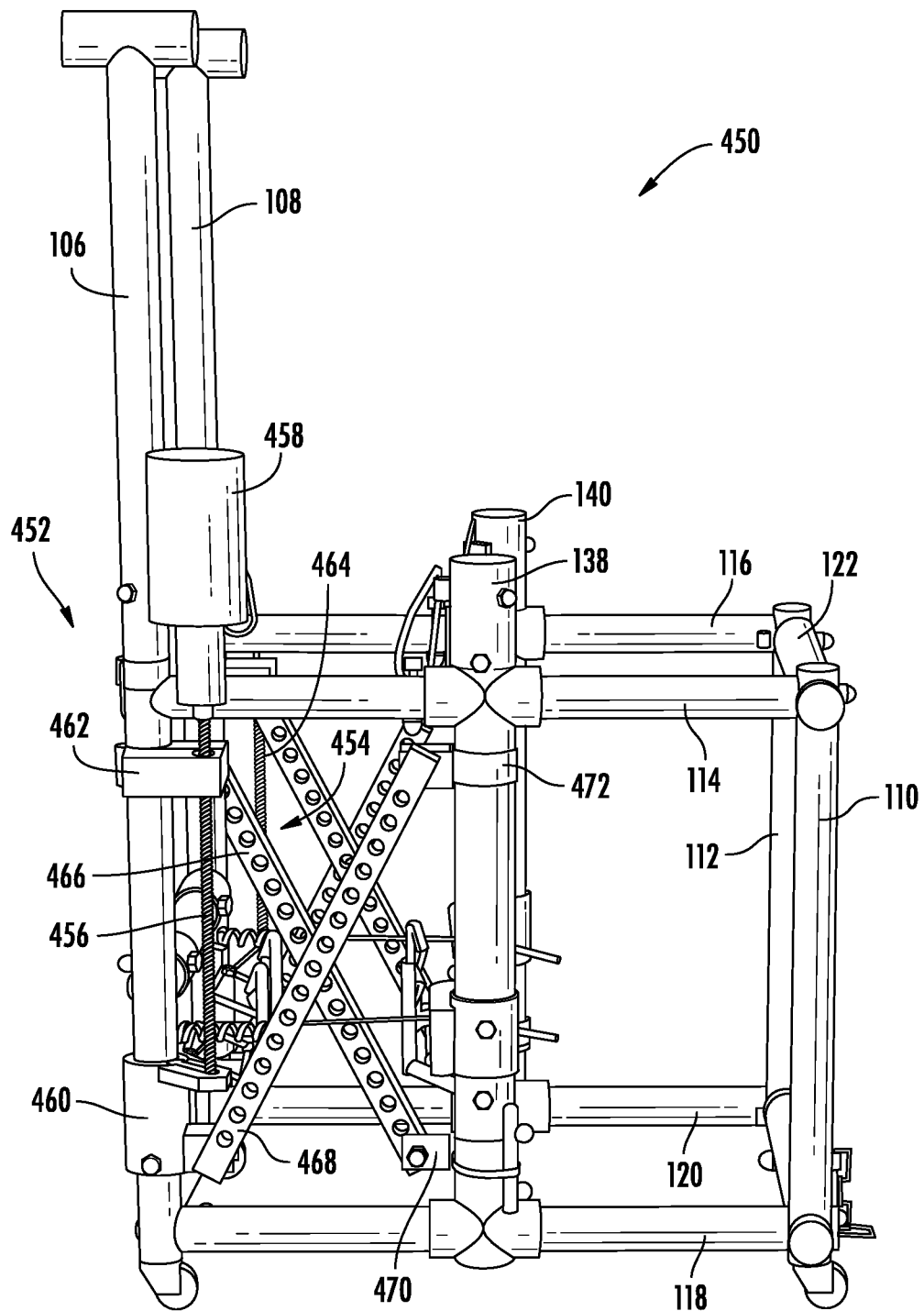
Figure 32:
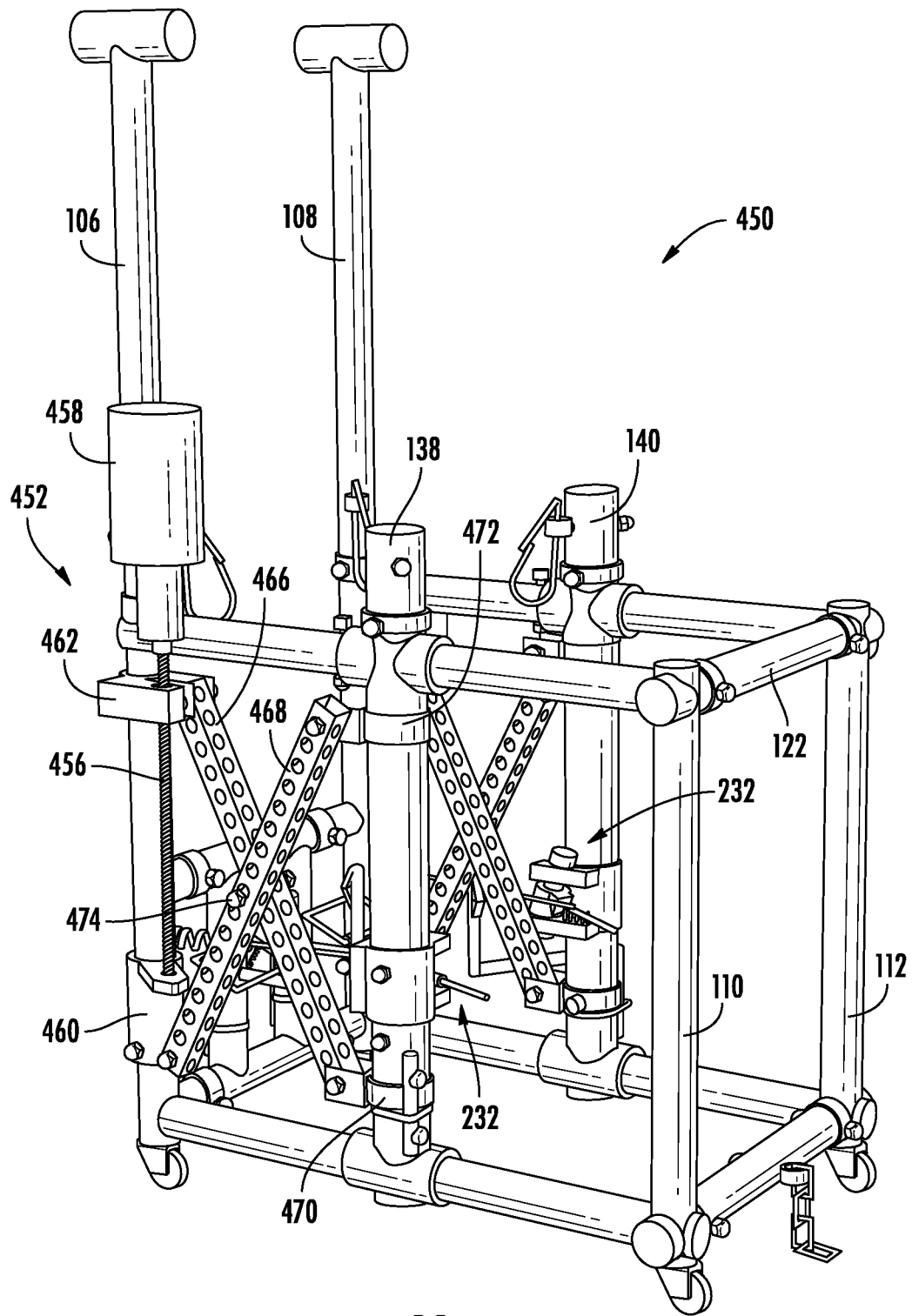
Figure 33:
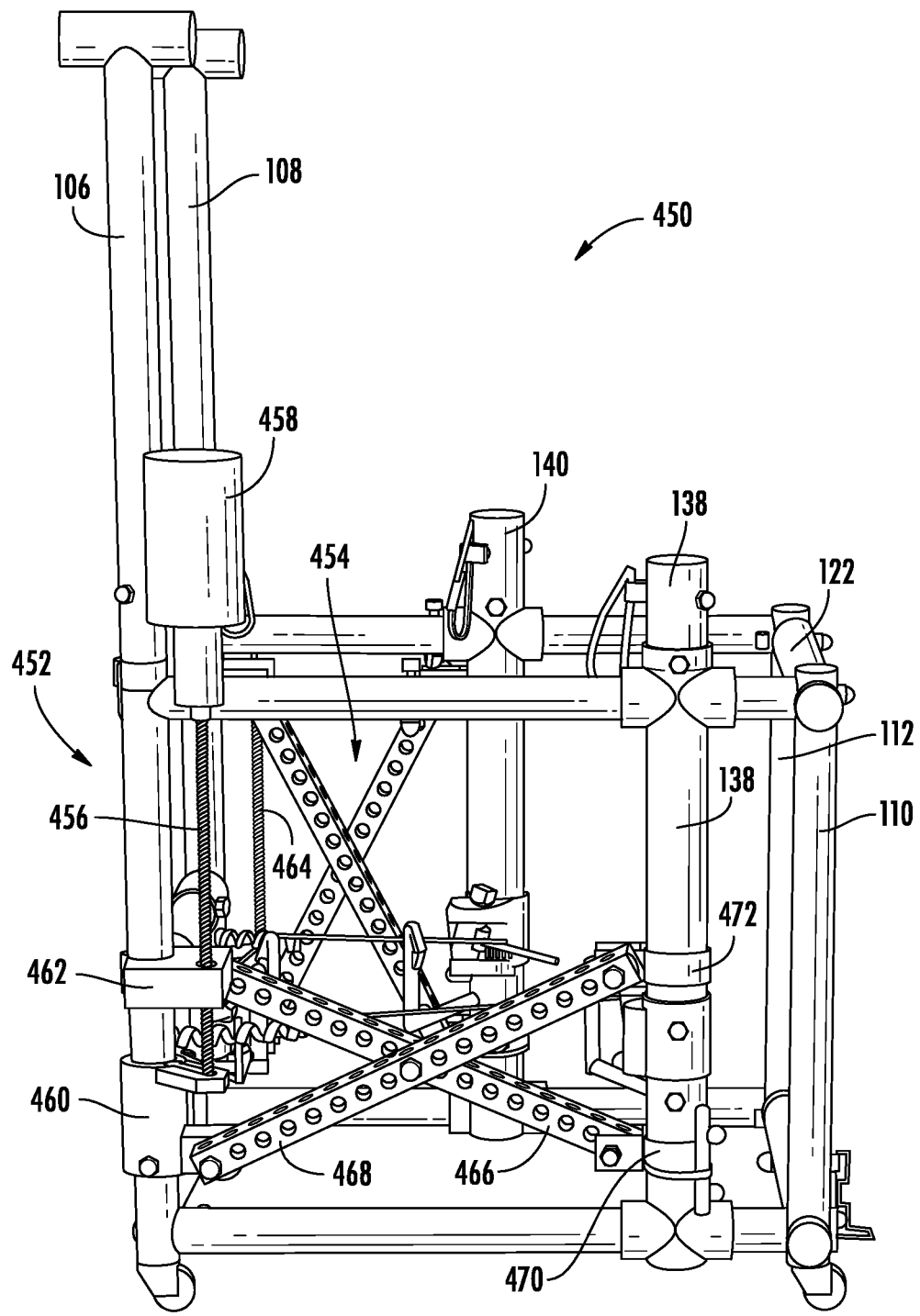
Figure 34:
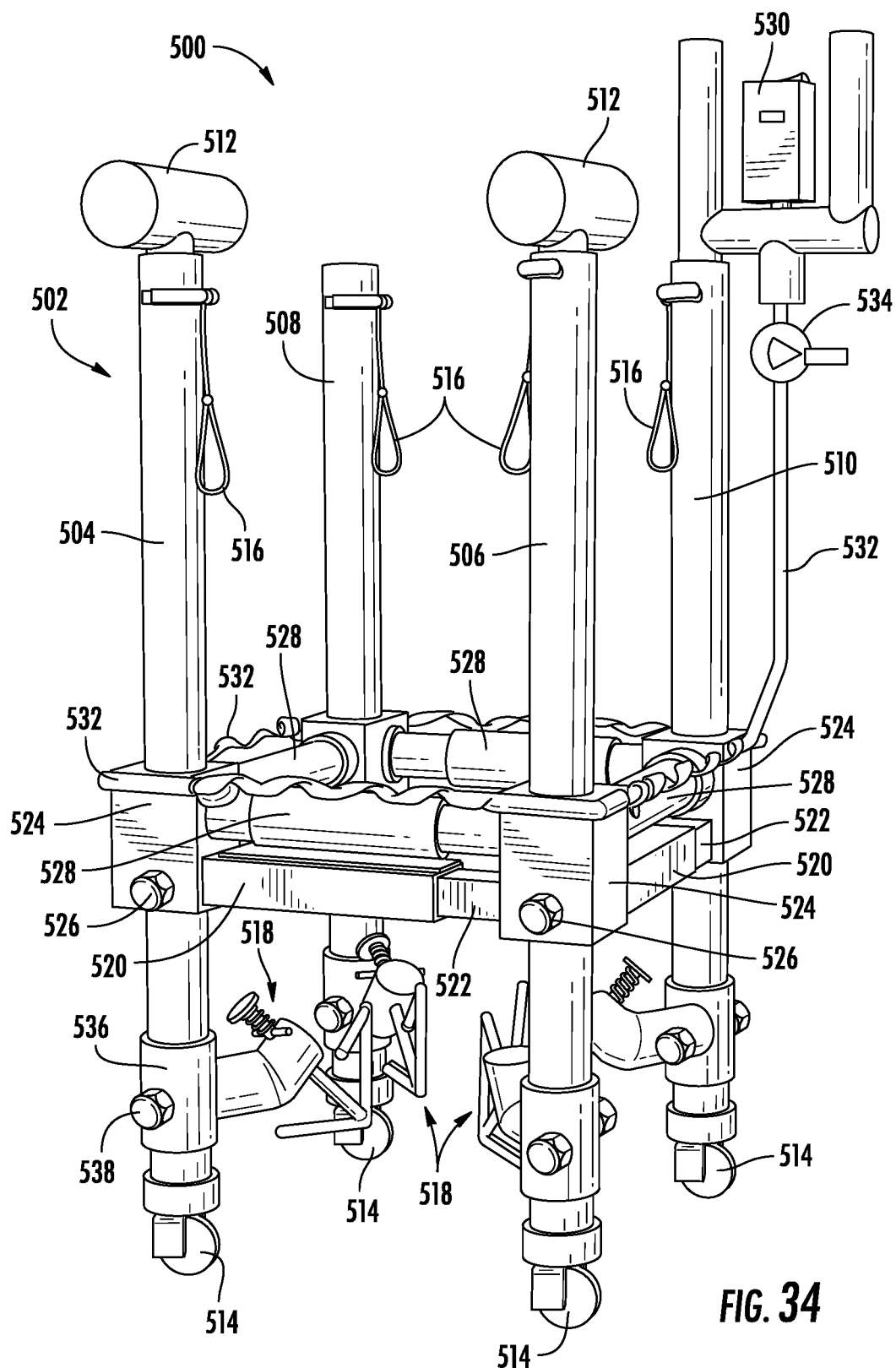
Figure 35:
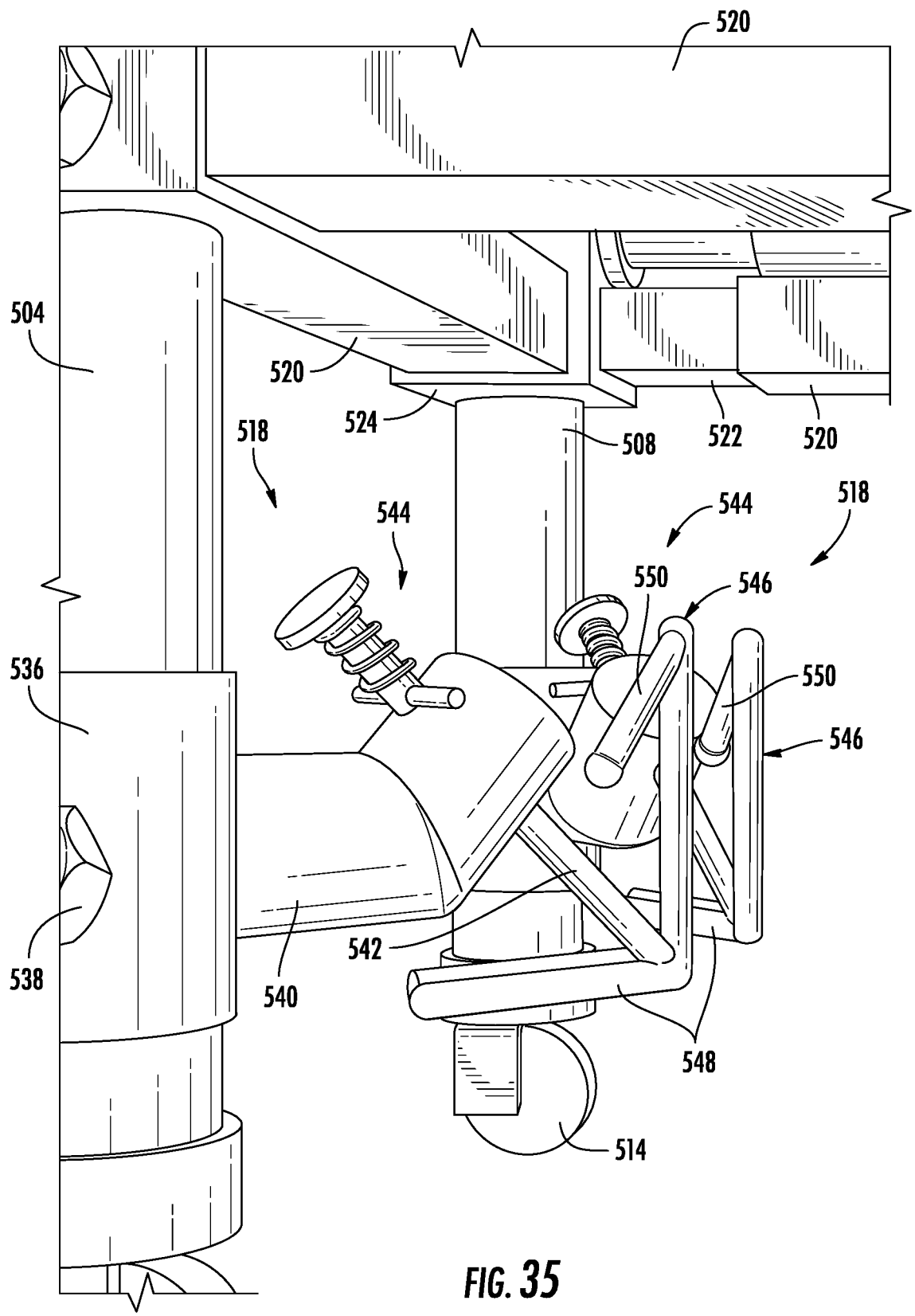
Figure 36:
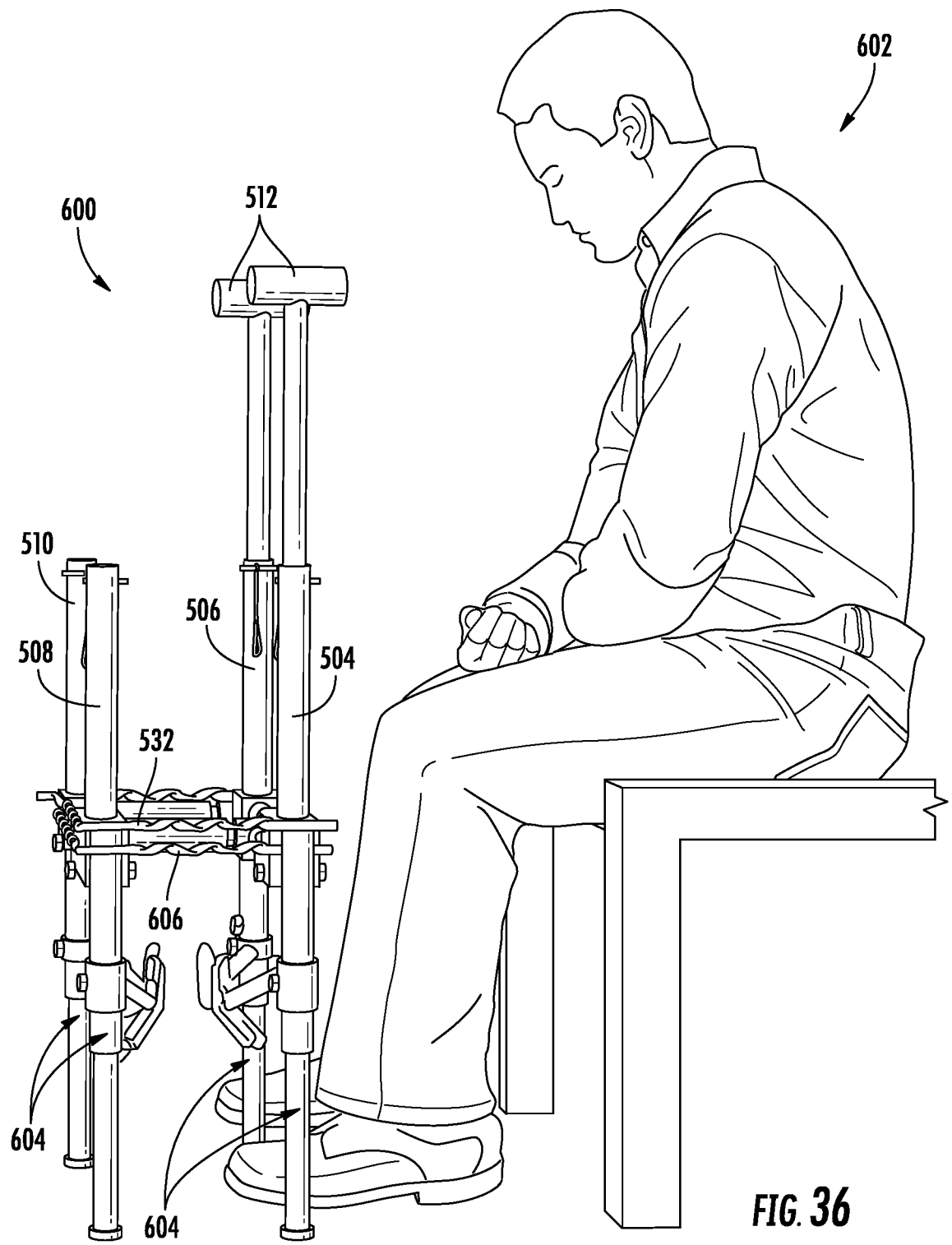
Figure 37:
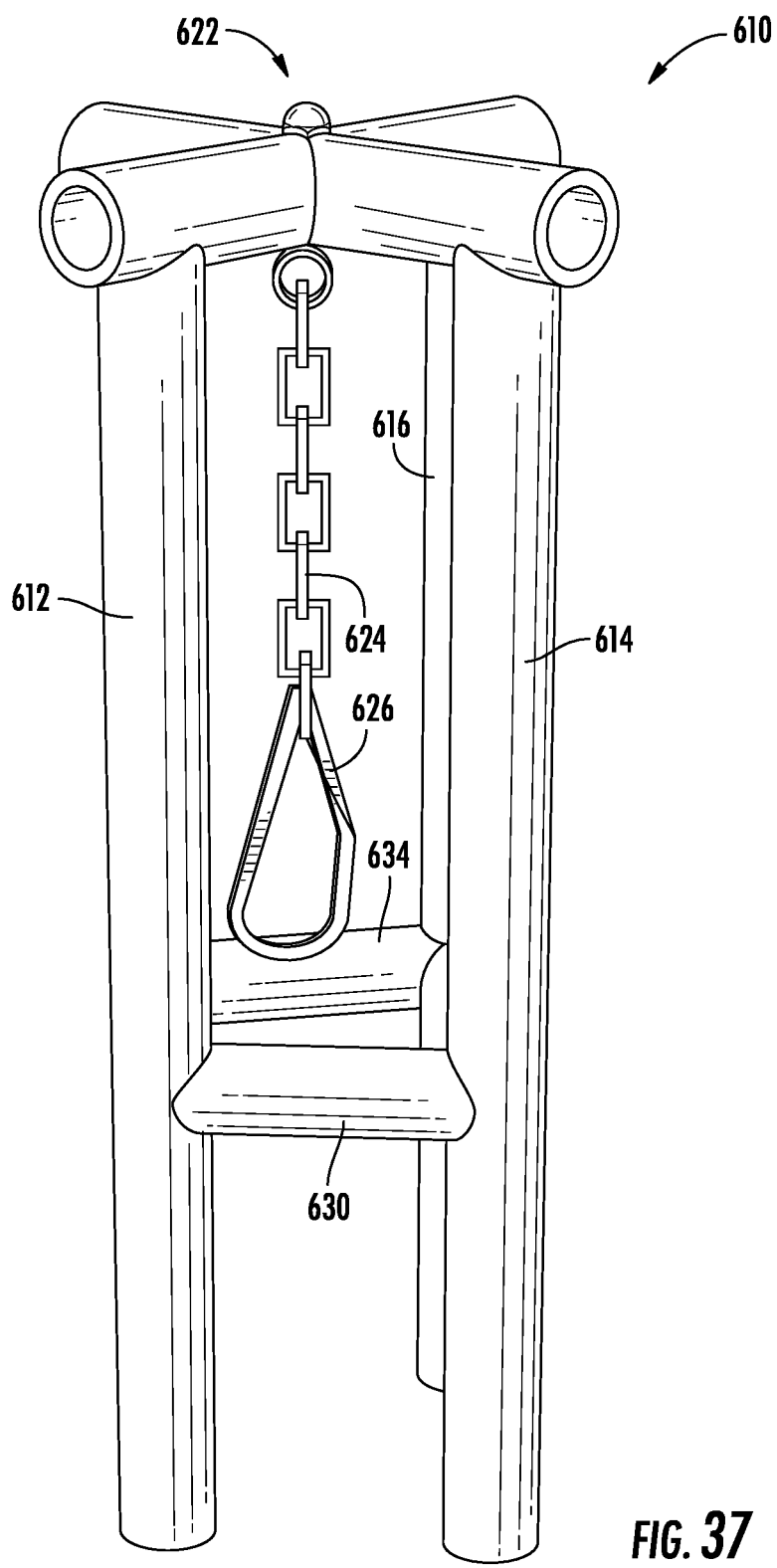
Figure 38:
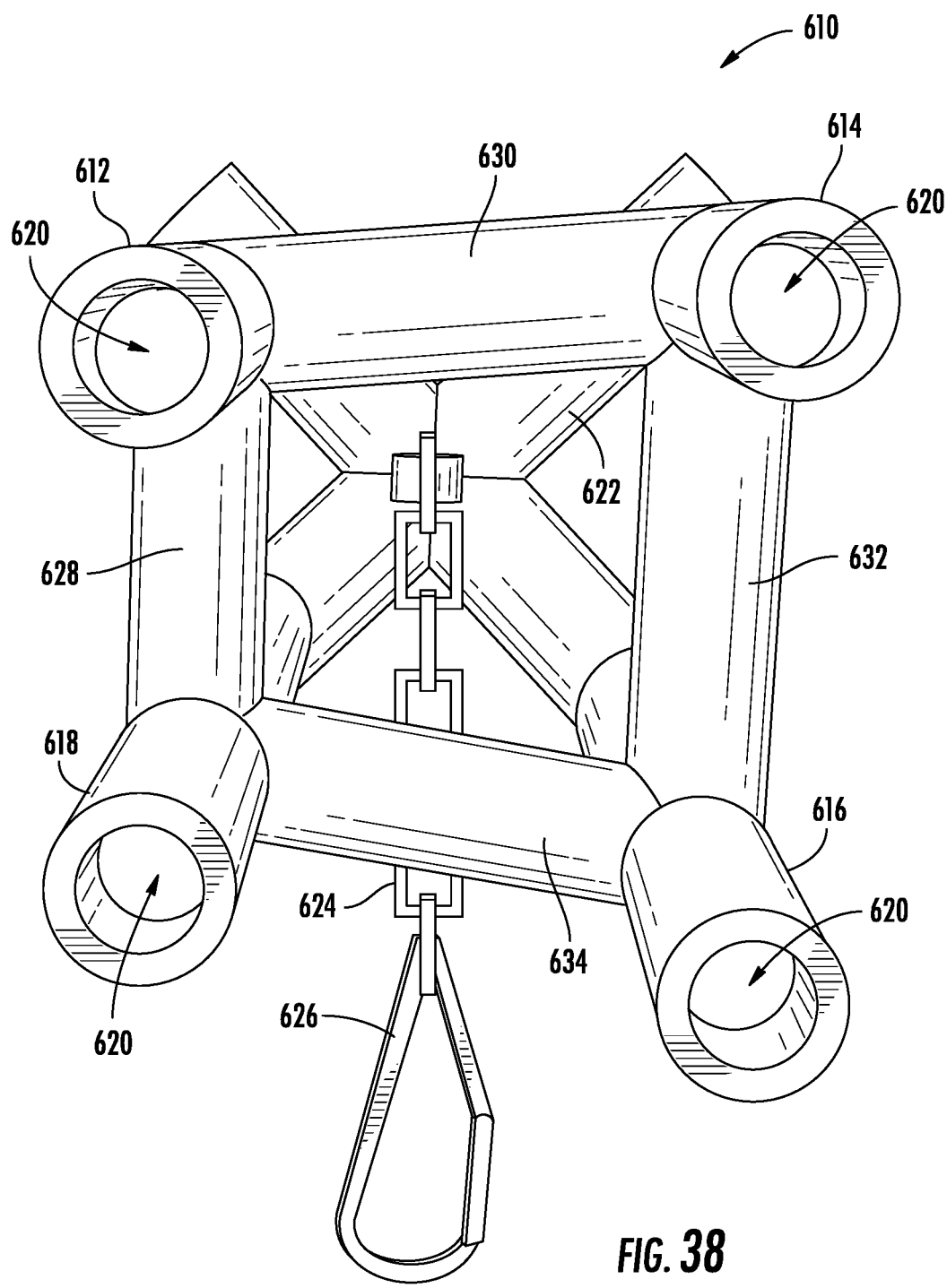
Figure 39:
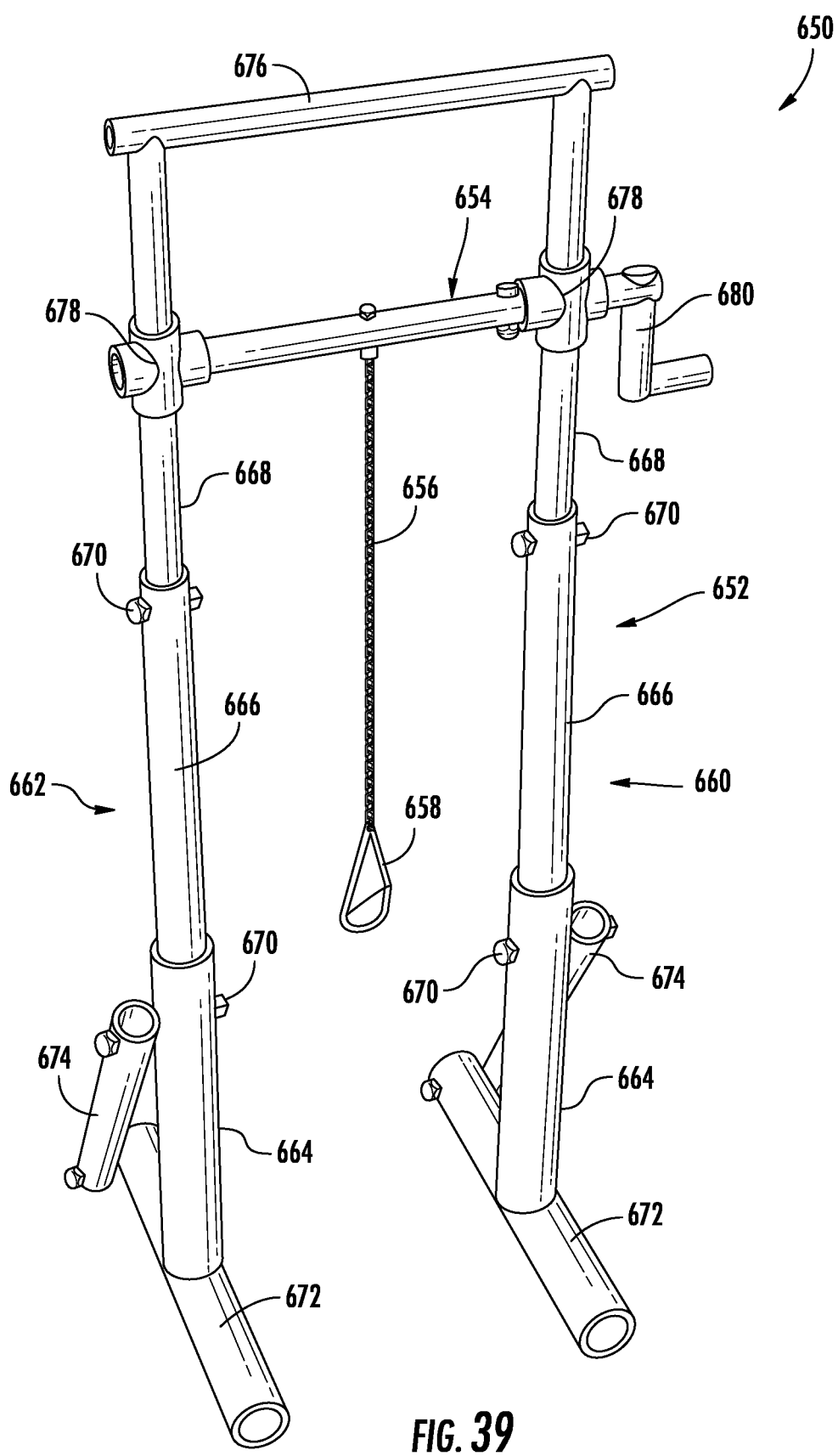
Figure 40:
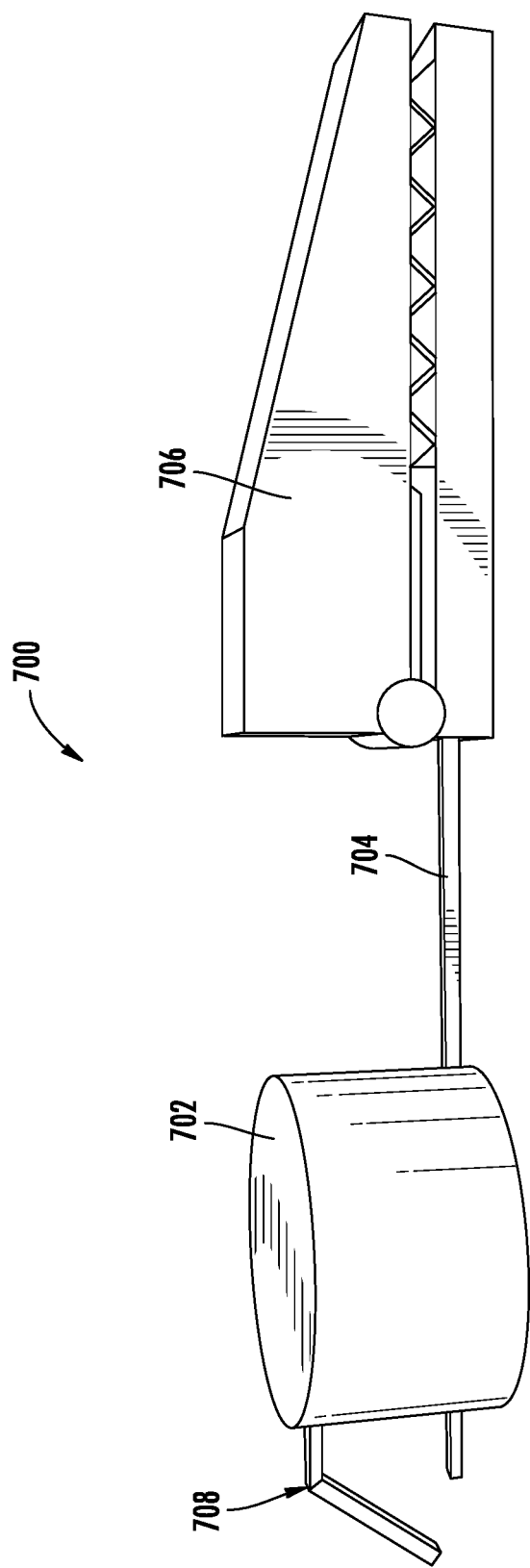
Figure 41:
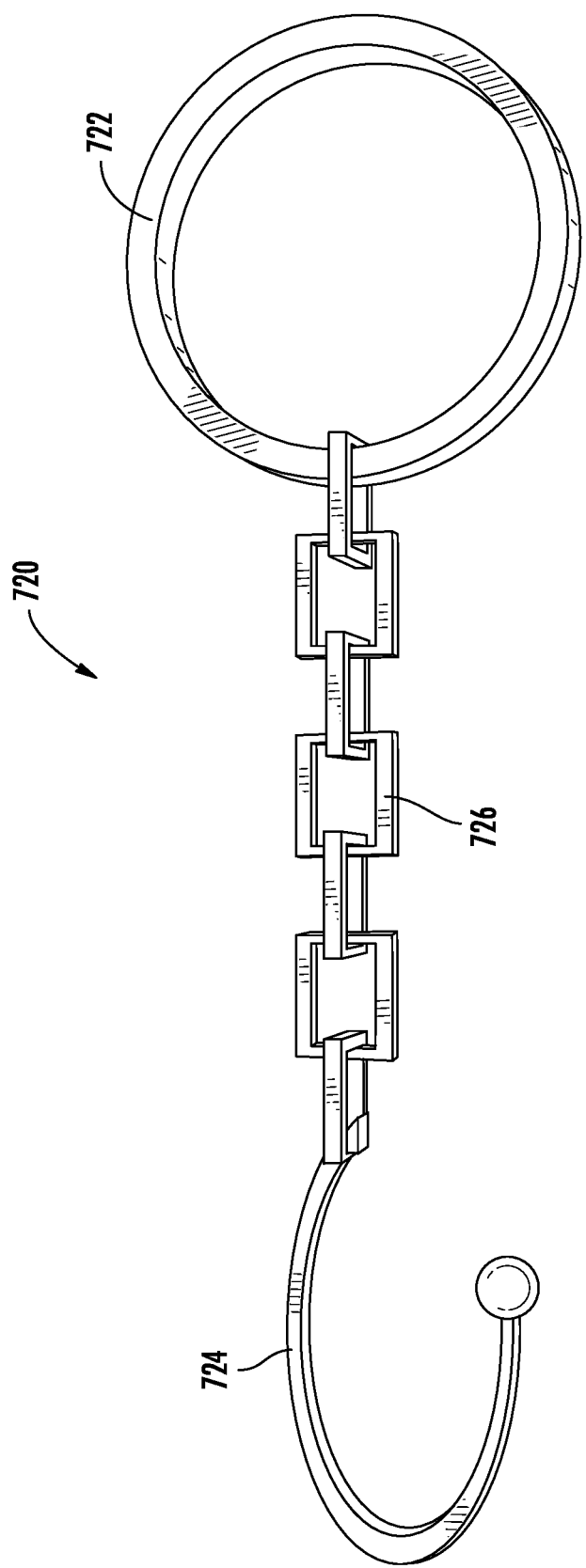
Figure 42:
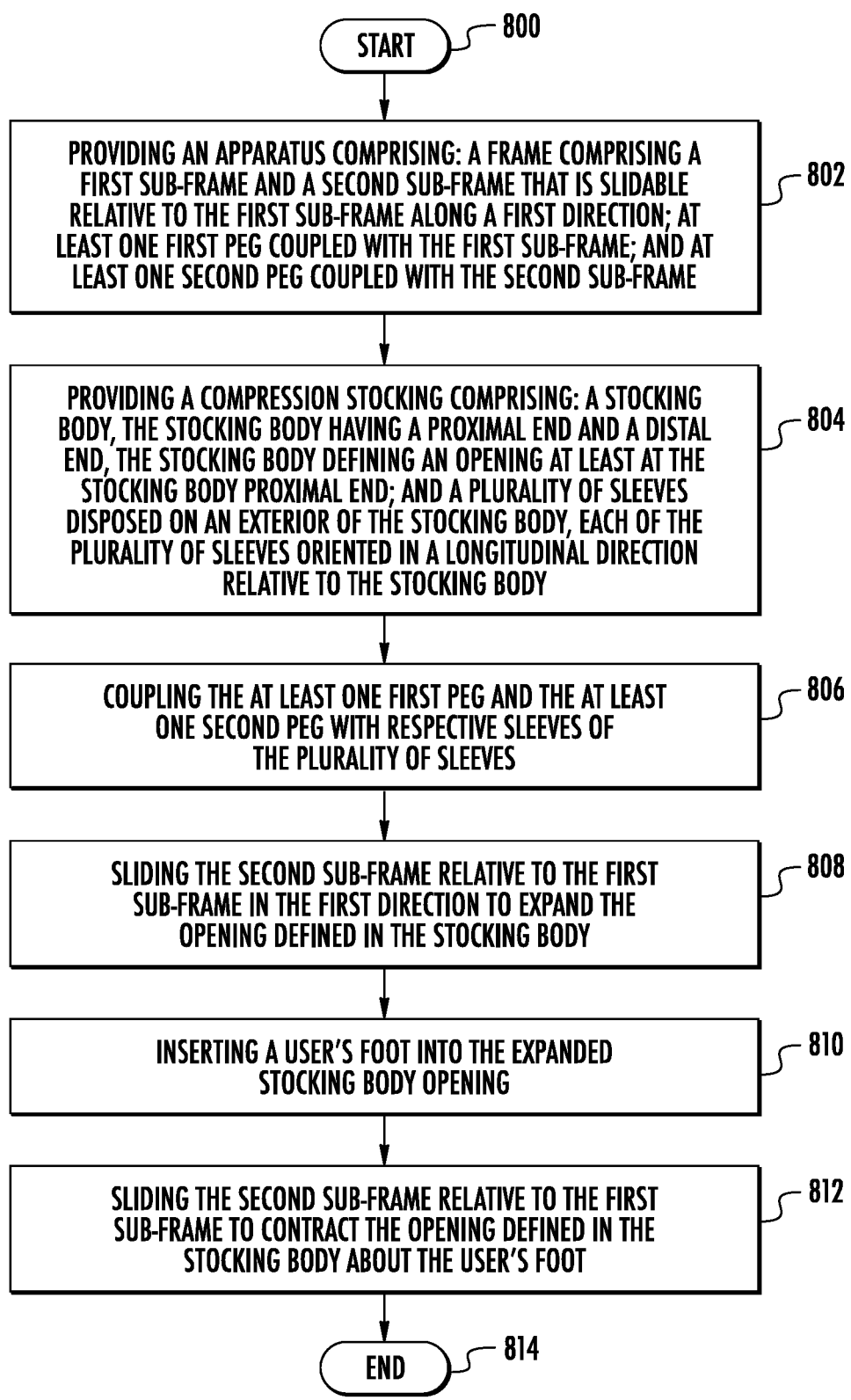
Figure 43:
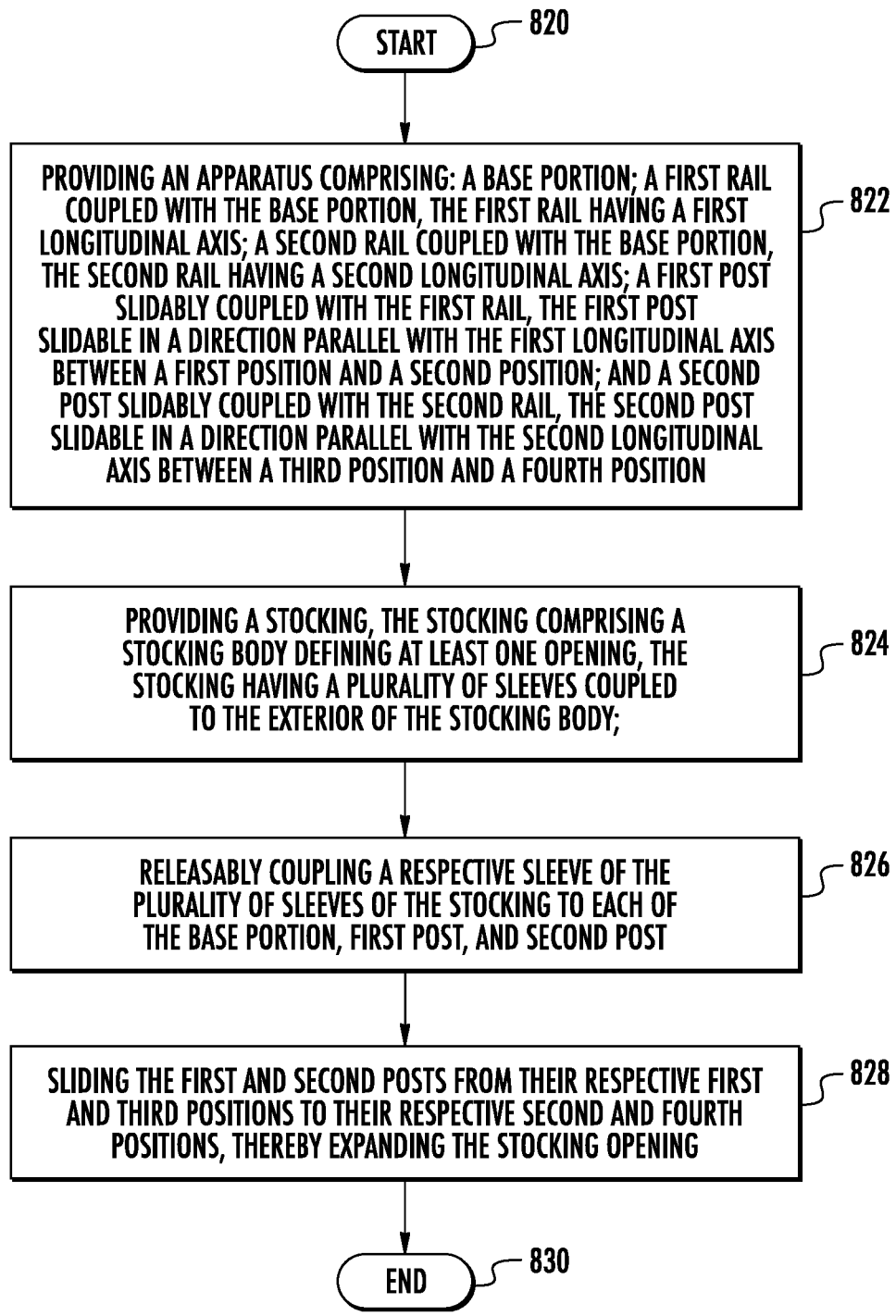
Figure 44:
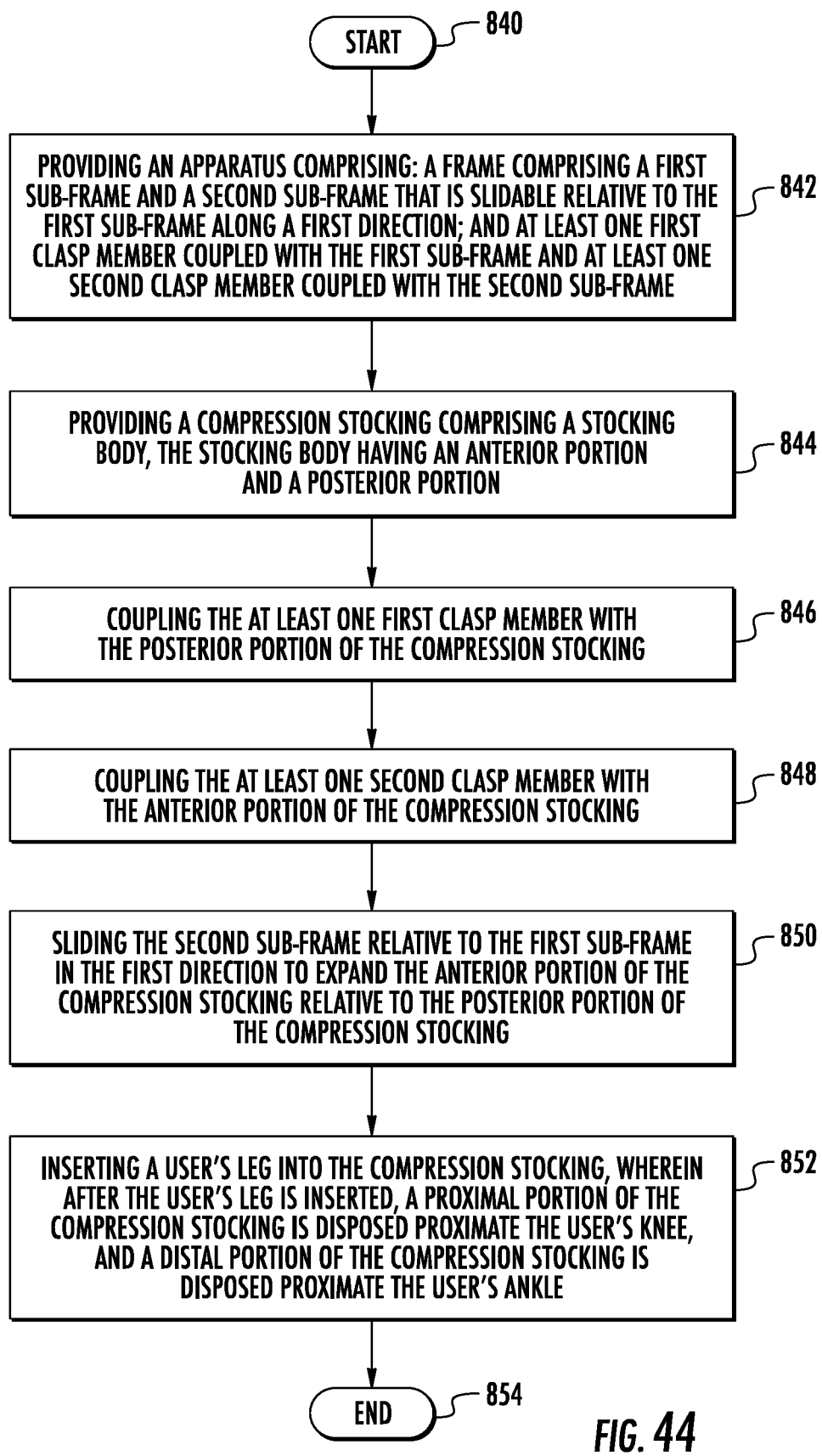

Having thus described some example embodiments in general terms, reference will now be made to the accompanying drawings, which are not necessarily drawn to scale, and wherein:

FIGS. 1a-1c are side elevation views of a human ankle in the extended, flexed, and neutral positions, respectively;

FIG. 2 is a perspective view of a stocking in accordance with an embodiment of the present invention;

FIG. 3 is a schematic top plan view of a stocking in accordance with an embodiment of the present invention;

FIG. 4 is a perspective view of a sleeve in accordance with an embodiment of the present invention;

FIG. 5 is a right-side perspective view of an apparatus for donning and/or doffing a stocking in accordance with an embodiment of the present invention;

FIG. 6 is a front-side perspective view of the apparatus of FIG. 5;

FIG. 7 is a rear-side perspective view of the apparatus of FIG. 5;

FIG. 8 is a partially exploded perspective view of a drive mechanism and control panel in accordance with an embodiment of the present invention;

FIG. 9 is a detail perspective view of a valve assembly that may be used with the control panel of FIG. 8;

FIG. 10 is an exploded view of the valve assembly of FIG. 9;

FIG. 11 is a perspective view of the underside of the control panel of FIG. 8 in accordance with an embodiment of the present invention;

FIG. 12 is a perspective view of the underside of the control panel and drive mechanism of FIG. 8 in accordance with another embodiment of the present invention;

FIG. 13 is a detail plan view of the apparatus of FIG. 5, wherein the clasp members are in an open position;

FIG. 14 is a detail plan view of the apparatus of FIG. 5, wherein the clasp members are in a closed position;

FIG. 15 is a detail perspective view of a clasp member of the apparatus of FIG. 5 in the open position in accordance with an embodiment of the present invention;

FIG. 16 is a detail perspective view of two clasp members of the apparatus of FIG. 5 in the closed position in accordance with an embodiment of the present invention;

FIG. 17 is a detail perspective view of another clasp member of the apparatus of FIG. 5 in the open position in accordance with an embodiment of the present invention;

FIG. 18 is a detail perspective view of the clasp member of FIG. 17 in the closed position in accordance with an embodiment of the present invention;

FIG. 19 is a partially exploded view of a linear actuator in accordance with an embodiment of the present invention;

FIG. 20 is a partially exploded view of a linear actuator in accordance with another embodiment of the present invention;

FIG. 21 is a right-side perspective view of an apparatus for donning and/or doffing a stocking in accordance with another embodiment of the present invention;

FIG. 22 is a front perspective view of the apparatus of FIG. 21;

FIG. 23 is a right-side perspective view of the apparatus of FIG. 21, wherein a sub-frame has been moved from a contracted position to an expanded position and clasp members have been moved from an open position to a closed position;

FIG. 24 is a right-side perspective view of an apparatus for donning and/or doffing a stocking in accordance with another embodiment of the present invention;

FIG. 25 is a right-side elevation view of the apparatus of FIG. 24;

FIG. 26 is a right-side elevation view of the apparatus of FIG. 24, wherein a post has been moved from a contracted position to an expanded position and a clasp member has been moved from an open position to a closed position;

FIG. 27 is a left-side perspective view of an apparatus for donning and/or doffing a stocking in accordance with another embodiment of the present invention;

FIG. 28 is a rear perspective view of the apparatus of FIG. 27;

FIG. 29 is a right-side perspective view of an apparatus for donning and/or doffing a stocking in accordance with another embodiment of the present invention;

FIG. 30 is a right-side perspective view of the apparatus of FIG. 29, wherein a sub-frame has been moved from a contracted position to an expanded position and clasp members have been moved from an open position to a closed position;

FIG. 31 is a right-side perspective view of an apparatus for donning and/or doffing a stocking in accordance with another embodiment of the present invention;

FIG. 32 is another right-side perspective view of the apparatus of FIG. 31;

FIG. 33 is a right-side perspective view of the apparatus of FIG. 31, wherein a post has been moved from a contracted position to an expanded position and wherein a clasp member has been moved from an open position to a closed position;

FIG. 34 is a front-side perspective view of an apparatus for donning and/or doffing a stocking in accordance with another embodiment of the present invention;

FIG. 35 is a detail view of a clasp member of the apparatus of FIG. 34 in accordance with an embodiment of the present invention;

FIG. 36 is a schematic perspective view of a user seated next to an apparatus for donning and/or doffing a stocking in accordance with another embodiment of the present invention;

FIG. 37 is a perspective view of a guiding apparatus in accordance with an embodiment of the present invention;

FIG. 38 is a bottom-side plan view of the guiding apparatus of FIG. 37;

FIG. 39 is a perspective view of a lifting apparatus which may be used with embodiments of the present invention;

FIG. 40 is a side elevation of a clip which may be used with embodiments of the present invention;

FIG. 41 is a perspective view of a hook and ring which may be used with embodiments of the present invention;

FIG. 42 is a flow chart according to example methods in accordance with an embodiment of the present invention;

FIG. 43 is a flow chart according to example methods in accordance with another embodiment of the present invention; and FIG. 44 is a flow chart according to example methods in accordance with another embodiment of the present invention.

Repeat use of reference characters in the present specification and drawings is intended to represent same or analogous features or elements of embodiments of the present invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

Further, either of the terms "or" and "one _____ of and _____," as used in this disclosure and the appended claims is intended to mean an inclusive "or" rather than an exclusive "or." That is, unless specified otherwise, or clear from the context, either of the phrases "X employs A or B" and "X employs one of A and B" is intended to mean any of the natural inclusive permutations. That is, either phrase is satisfied by any of the following instances: X employs A; X employs B; or X employs both A and B, regardless whether the phrases "at least one of A or B" or "at least one of A and B" are otherwise utilized in the specification or claims. In addition, the articles "a" and "an" as used in this application and the appended claims should generally be construed to mean "one or more" unless specified otherwise or clear from the context to be directed to a singular form. Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may.

Embodiments of the present invention comprise apparatus and methods for aiding a user in donning and doffing a stocking. Certain embodiments are described below in the context of a compression stocking, but those of skill in the art will appreciate that the present invention is not so limited. For instance, various embodiments of the present invention may be usable with, employ, and/or comprise any type of stocking. Likewise, in various embodiments, the wearer of a stocking and an operator of an aid apparatus or other device or method may not be the same individual. Accordingly, the term "user" herein is defined to include both the wearer of a stocking and any operator(s) that may be assisting the wearer. Additionally, various embodiments are described with reference to certain anatomical directions relative to a user's body part. When such a directional term is used (e.g., the anatomical anterior to posterior direction), it is intended to include either or both such directions (e.g., the anatomical anterior direction, the anatomical posterior direction, or both the anatomical anterior and the anatomical posterior directions) unless otherwise noted.

As noted above, there are various reasons it may be difficult for a user to don and/or doff a compression stocking. One additional factor that contributes to this difficulty is described with reference to FIGS. 1a-1c, which are side elevation views of a human's ankle 10 in the extended, flexed, and neutral positions, respectively. Ankle 10 has a dimension denoted "A" that represents the transverse distance across the ankle 10 at the base of the human's shin. Ankle 10 also has a dimension denoted "B" that represents the distance between the base of the human's heel (also called the calcaneus tuberosity) to the base of the shin (also called the distal margin of the tibia). As those of skill in the art will appreciate, a stocking that the user intends to don and/or doff may have an opening sized to readily accommodate the dimension A, but the stocking may only accommodate dimension B when the stocking is stretched, and then perhaps only with some difficulty, which may be exacerbated due to swelling of the user's leg, foot, or ankle. As shown in these figures, irrespective of how the human's foot and/or ankle is flexed or extended, the dimension B will always be greater than the dimension A. With known stockings and methods of donning and/or doffing such stockings, it is typically very difficult to pass ankle 10 through the opening defined in the stocking.

In this regard, attempts aid a user in donning and/or doffing a stocking by stretching the stocking in the anatomical lateral to medial direction relative to the user's ankle have little effectiveness. For example, U.S. Pat. No. 255,180 to Master, entitled "Elastic Stocking," discloses a stocking A having a plurality of straps C coupled with stays that extend on each lateral side of stocking A. Straps C, which are disposed at various vertical positions along the stocking A, have their ends attached to stays B so as to form loops or handles that may be grasped when the stocking is to be pulled on. Because of their placement on the lateral sides of socking A, though, straps C can only be used stretch stocking A in the anatomical lateral to medial direction. As such, the stocking disclosed in the '180 Patent cannot be stretched in the anatomical anterior to posterior direction using straps C, and thus this stocking will not facilitate passage of the foot's large dimension B. This would be the case whether the stocking is donned via a user's manual grasping of straps C (as contemplated in the '180 Patent), or even if a machine or apparatus were to be used to hold straps C in a stretched position.

For the same reason, attempts to aid a user in donning and/or doffing a stocking by pulling or applying force to the stocking in the anatomical superior direction relative to the user's ankle, or the anatomical superior and posterior directions relative to the user's ankle, also have limited effectiveness.

Rather, Applicant has determined that stretching the stocking at least in the anatomical anterior to posterior direction relative to the user's ankle has far greater effectiveness, in that the size of the opening defined in the stocking will be increased in a direction that is aligned with the dimension B described above, thereby easing passage of same through the opening. However, it is typically difficult or impossible for a user, alone or with assistance, to maintain the stocking in this stretched position while also donning and/or doffing the stocking.

Referring now to FIG. 2, a stocking 20 in accordance with an embodiment of the present invention comprises a stocking body 22. In various embodiments, stocking body 22 may be analogous to any stocking known to those of ordinary skill in the art. In some embodiments, stocking body 22 may comprise a compression stocking. The stocking body 22 has a proximal end 24 and a distal end 26. An opening 28 may be defined at least at proximal end 24. As will be understood, a user's foot and leg may be inserted into opening 28. When the user's foot and leg are inserted into opening 28, the user's knee may be disposed proximate proximal end 24, and the user's ankle may be disposed proximate distal end 26.

The stocking body 22 can further comprise a foot portion 30 coupled with or integrally formed with the stocking body 22, though foot portion 30 is not required in all embodiments. Where foot portion 30 is not provided, a further opening may be defined at distal end 26. Here, foot portion 30 extends between a heel 32 and toe 34. Likewise, in some embodiments, foot portion 30 may be provided, but may not include toes. In various embodiments, stocking body 22 may extend to the level of a user's shin, knee, or higher, as needed or desired. As shown in FIG. 2, stocking body 22 also defines a longitudinal axis 36. Longitudinal axis 36 extends out of the page in FIG. 3.

As described in more detail herein, in various embodiments, a plurality of sleeves 38 may be disposed on an exterior of stocking body 22. Sleeves 38 preferably are oriented longitudinally relative to stocking body 22. In some embodiments, sleeves may have an opening defined on at least one end thereof and adapted to receive a prong of an apparatus for assisting a user for donning and/or doffing a compression stocking, as described herein. In some embodiments, sleeves 38 may have a longitudinal axis that is parallel with longitudinal axis 36, but this is not required in all embodiments, and in other embodiments, the longitudinal axis of one or more of sleeves 38 may be disposed at an angle relative to longitudinal axis 36. In some embodiments, a tab 40 may be coupled with each sleeve 38 in order to facilitate flattening of sleeve 38 against stocking body 22. Additionally, and also as described below, in some embodiments one or more magnetic discs 42 may be coupled with stocking body 22, either on an interior or exterior surface thereof.

Referring now also to FIG. 3, when viewed in plan, stocking body 22 may define an anterior-to-posterior axis 44 and a lateral-to-medial axis 46. In some embodiments, axes 44 and 46 may intersect longitudinal axis 36 and/or a center point 47 of opening 28, or both. In some embodiments, axes 44, 46 may be perpendicular to one another. Stocking body 22 may further define a first offset axis 48 and a second offset axis 50. In some embodiments, axes 48 and 50 may intersect longitudinal axis 36 and/or the center point of opening 28, or both. In some embodiments, axes 48, 50 may be perpendicular to one another. Axis 50 may be offset from axis 44 by an angle α, and axis 48 may be offset from axis 44 by an angle β. In some embodiments angles α and β may each be about 45 degrees, though they may be other angles in other embodiments.

Stocking body 22 may define an anterior portion 52 and a posterior portion 54. In general, anterior portion 52 may include that part of stocking body 22 forward of lateral-to-medial axis 46 (i.e., toward toe 34), and posterior portion 54 may include that part of stocking body 22 rear of lateral-to-medial axis 46 (i.e., toward heel 32). As described in greater detail herein, in some embodiments, one or more clasp members of an apparatus for aiding a user in donning and/or doffing a stocking may be coupled with each of the anterior and posterior portions 52, 54, respectively. The apparatus may be used to expand the anterior portion 52 of stocking 20 relative to the posterior portion 54 of stocking 20.

Axis 44 may intersect stocking body 22 at a first position 56 that corresponds to an anatomical anterior position. Similarly, axis 44 may intersect stocking body 22 at a second position 58 that corresponds to an anatomical posterior position. Also, axis 46 may intersect stocking body at a first position 60, corresponding to an anatomical lateral position, and at a second position 62, corresponding to an anatomical medial position. Positions 56, 58, 60, and 62 may each be angular positions about longitudinal axis 36.

Axis 48 may intersect stocking body 22 at a first position 64, e.g., an angular position about longitudinal axis 36 that is between positions 56 and 62, and at a second position 66, e.g., an angular position about longitudinal axis 36 that is between positions 58 and 60. Likewise, axis 50 may intersect stocking body 22 at a first position 68, e.g., an angular position about longitudinal axis 36 that is between positions 56 and 60, and at a second position 70, e.g., an angular position about longitudinal axis 36 that is between positions 58 and 62. Each of positions 64, 66, 68, and 70 may be angularly offset from the anatomical anterior and posterior positions (and from the anatomical medial and lateral positions) by a predetermined angle, e.g., 45 degrees. In other embodiments, though, other angles are contemplated, and the selected angle will determine the angular positions at which these axes intersect stocking body 22. For instance, axis 48 need not be offset from axis 44 by the same angle that axis 50 is offset from axis 44 in all embodiments.

As best seen in FIG. 3, in some embodiments, sleeves 38 may be coupled with stocking body 22 at each of angular positions 64, 66, 68, and 70. In some embodiments, the angular positions at which sleeves 38 are disposed may be selected to avoid high pressure points (e.g., the inner and outer ankle malleolus) or points likely to rub against a user's shoe (e.g., at the distal tibia and/or over the Achilles tendon). In other embodiments, though, sleeves 38 may be coupled with stocking body 22 at other angular positions, including at each of angular positions 56, 58, 60, and 62 or other positions. Additionally, in various embodiments, more than or fewer than four sleeves 38 may be coupled with stocking body 22. In other words, in some embodiments, a sleeve 38 could be coupled with stocking body 22 at angular positions 64, 68, and 58. Other configurations are contemplated.

In various embodiments, more than one "layer" of sleeves 38 may be provided. For instance, as shown in FIG. 2, in one embodiment two such layers are provided. Where multiple layers of sleeves are provided, the sleeves in one layer need not be disposed at the same angular positions as the sleeves in another layer, though they may. The length or height of stocking 20 may impact the number of layer of sleeves 38 provided. In some embodiments, a layer of sleeves 38 may be provided at the level of the ankle, a layer of sleeves 38 may be provided at the level of the mid-shin, and a layer of sleeves 38 may be provided at the level of the knee. Again, though, other arrangements are contemplated. In some embodiments, each sleeve 38 in a given layer may be disposed at the same height on stocking body 22, though this too is not required in all embodiments.

In various embodiments, each sleeve 38 may be coupled with stocking body 22 either when the stocking 20 is manufactured or at some point thereafter. Sleeves 38 may be coupled with stocking body 22 by any suitable method familiar to those of skill in the art. For example, in some embodiments, sleeves 38 may be attached to stocking body 22 by sewing, via buttons or snaps, or via a suitable adhesive. In various embodiments, sleeves 38 may be permanently or removably affixed to stocking body 22.

FIG. 4 is a perspective view of a sleeve 38 in accordance with an embodiment of the present invention. In FIG. 4, sleeve 38 is not coupled with a stocking. As an initial matter, it is noted that sleeve 38 is one type of attachment mechanism that may be used to releasably couple a stocking 20 to an apparatus for aiding a user in donning and/or doffing stocking 20. Other suitable attachment mechanisms are contemplated and may be used in various embodiments, including but not limited to eyes, hooks, clasps, and grommets.

In some embodiments, sleeve 38 comprises an elongate body 72 having one or more openings defined therein. As shown, body 72 is cylindrical in shape and defines a bore 73 extending between a first opening 74 and an opposite second opening 76. Body 72 defines a longitudinal axis 78 that extends out of the page in FIG. 4. In other embodiments, body 72 need not be cylindrical in shape. For example, body 72 may have a square, triangular, half-circle or other cross-section in some embodiments.

As noted above, in some embodiments sleeves 38 may be oriented longitudinally relative to stocking body 22. In this regard, and in general, in some embodiments sleeves 38 may be "vertically accessed" by a suitable member (e.g., a prong or the like) of an apparatus for aiding a user in donning and/or doffing a stocking. In other words, in various embodiments, sleeves 38 may be coupled and uncoupled with such a member only via movement of sleeve 38 (and stocking 20) in an upward or downward vertical direction relative to the member, rather than a horizontal or side-to-side direction. Thus, in some embodiments, the sleeve 38 may be affixed to stocking body 22 at a lateral surface of sleeve 38, rather than at its superior or inferior margin. Accordingly, in one embodiment, an aid apparatus's clasp may connect with sleeve 38 by passing partially or entirely through bore 73 in a vertical direction.

In various embodiments, sleeve body 72 may have any suitable dimension relative to stocking body 22. As noted above, in some embodiments, body 72 may be elongate and may have a length that is greater than its width or diameter. In various other embodiments, however, the ratio of the length of body 72 to its width or diameter, as the case may be, is not limited.

Sleeve 38 may be formed of any suitable material in various embodiments. In one embodiment, sleeve 38 may be formed of a non-elastic material. In some embodiments, the material from which sleeve 38 is made may be cloth or cloth-like. In this regard, in some embodiments, it is preferred that sleeve 38 be formed from a soft material that will not put pressure on a user's ankle, foot, or leg when the sleeve 38 is not in use (e.g., when not coupled with an aid apparatus as described herein). It is also preferred in some embodiments that sleeve 38 not be elastic such that it will transfer, rather than absorb, a pulling force from an aid apparatus's clasp, prong, or the like to the stocking 20.

In some embodiments, sleeves 38 may be deformable and/or flattenable so that, when the sleeves 38 are not being used with an aid apparatus, or after a stocking is donned or doffed, the sleeves 38 may be flattened against stocking body 22. This may also be done for cosmetic reasons or to prevent sleeves 38 from catching on another object. In this regard, in FIG. 2, the upper and lower anterior portion sleeves 38 are shown as flattened relative to stocking body 22, while the upper and lower posterior portion sleeves 38 are shown in the open position. Also, as noted above, in some embodiments, a tab 40 coupled with sleeves 38 may be used to secure sleeves 38 in a closed or flattened position against stocking body 22. For instance, tabs 40 may comprise a Velcro material, a button or snap, or another suitable attachment mechanism, to couple tabs 40 with stocking body 22. A tab 40 may be used by pulling its proximal edge upward and affixing it to a part of the stocking body 22 that is separate from sleeve 38. In various embodiments, the use of elastic bands to hold sleeves 38 in a closed position, rather than tabs 40 or another similar structure, is not preferred due to the risk of impairing blood flow in a user having chronic edema.

In some embodiments, sleeves 38 may be biased toward their open position. In some embodiments, a structure 80 optionally may be positioned either within bore 73 (as shown), or on the exterior thereof, to retain or bias sleeves 38 toward their open position. As shown, structure 80 is a ring or coil formed from a semi-rigid material, but other structures may be used in other embodiments. In some embodiments, structure 80 may be removable from bore 73. Where structure 80 is provided, it may also be formed from a material that is not magnetic or only weakly so. In various embodiments, sleeves 38 may be deformable or flattenable even when provided with structure 80.

As noted above, in some embodiments one or more magnetic discs 42 may be coupled with stocking body 22. Magnetic discs 42 may be removably or permanently coupled to stocking body 22 via any suitable attachment mechanism, including but not limited to Velcro, snaps or buttons, sewing, or a suitable adhesive. In various embodiments, magnetic discs 42 may be disposed proximate distal end 26 and proximate one or more sleeves 38, but that is not required in all embodiments. It is contemplated that, where magnetic discs 42 are provided, magnetic discs 42 may help retain stocking 20 in place after one or more sleeves 38 are coupled with a prong of an aid apparatus as described herein. In some embodiments, discs 42 may be particularly useful, such as where a user must attach stocking 20 indirectly, via an intermediate device, such as a reach-extender or the like, or such as a guiding apparatus described herein.

Next, in various embodiments, an apparatus for donning and/or doffing a stocking employs one or more linear actuators (e.g., a double-acting pneumatic cylinder) to cause movement of one or more frame elements relative to a base portion in one or more axes (e.g., an axis that corresponds to the anterior-to-posterior anatomical direction, the medial-to-lateral anatomical direction, and/or the superior-to-inferior anatomical direction). Such movement may cause a stocking (or an opening defined therein) to be stretched in such direction(s). As used herein, the term "linear actuator" refers to any automated or manual actuator for generating motion in a straight line. The term includes, but is not limited to, fluid cylinders (including hydraulic and pneumatic cylinders and including syringes), mechanical linear actuators (including horizontal or vertical screws, wheel-and-axle actuators, cables wound around a vertical shaft, and cams), scissor jacks, and electromechanical actuators. As contemplated herein, linear actuators may be single- or double-acting, and they may be driven by any suitable manual or automated drive mechanism (e.g., a pump (e.g., positive pressure or vacuum), motor (e.g., electric, hydraulic, intrinsic, extrinsic, including third-party removable motors, such as screw-drivers and/or air pumps), handle, crank, knob, etc.).

FIGS. 5-7 are respective right-side, front-side, and rear-side perspective views of an apparatus 100 for donning and/or doffing a stocking in accordance with an embodiment of the present invention. As shown, apparatus 100 comprises a frame 102. Frame 102 in the illustrated embodiment comprises a base portion 104 comprising a first post 106 having a first longitudinal axis and a second post 108 having a second longitudinal axis. The longitudinal axes of first and second posts 106, 108 may be parallel in some embodiments and may lie on a first plane. Base portion 104 may also comprise a third post 110 and a fourth post 112 which define respective third and fourth longitudinal axes. The longitudinal axes of third and fourth posts 110, 112 may be parallel in some embodiments and may lie on a second plane. The second plane may, in some embodiments, be parallel with the first plane but spaced apart therefrom.

Frame 102 may also comprise a first rail 114 extending between first post 106 and third post 110 to couple first and third posts 106, 110 together, and a second rail 116 extending between second post 108 and fourth post 112 to couple second and fourth posts 108, 112 together. Similarly, frame 102 may also comprise a third rail 118 extending between first post 106 and third post 110 to couple first and third posts 106, 110 together, and a fourth rail 120 extending between second post 108 and fourth post 112 to couple second and fourth posts 108, 112 together. In various embodiments, any number of rails may be provided, as needed or desired.

Each of rails 114, 116, 118, and 120 may define respective fifth, sixth, seventh, and eighth longitudinal axes. In some embodiments, all such longitudinal axes may be parallel, though that is not required. In some embodiments, fifth and seventh longitudinal axes of rails 114 and 118 may be parallel and lie on a third plane. The third plane may be perpendicular to the first and/or second planes described above. In some embodiments, sixth and eighth longitudinal axes of rails 116 and 120 may be parallel and lie on a fourth plane. The fourth plane likewise may be perpendicular to the first and/or second planes described above. The third and fourth planes may in some embodiments be parallel but spaced apart.

In various embodiments, frame 102 may also comprise a fifth rail 122 extending between upper ends of posts 110 and 112 and a sixth rail 124 extending between respective lower ends of posts 110 and 112. Fifth and sixth rails 122, 124 may define respective ninth and tenth longitudinal axes. These ninth and tenth longitudinal axes may in some embodiments be parallel and in some cases may lie on the second plane, though this is not always required. Additionally, in various embodiments, frame 102 may also comprise a seventh rail 126 extending between posts 106 and 108 and an eighth rail 128 extending between respective lower ends of posts 106 and 108. Seventh and eighth rails 126, 128 may define respective eleventh and twelfth longitudinal axes. These eleventh and twelfth longitudinal axes may in some embodiments be parallel and in some cases may lie on the first plane, though this is not always required.

Frame 102 can comprise an anterior side, which in use may correspond to the anatomical anterior direction relative to the user (or a user's appendage), and a posterior side, which in use may correspond to the anatomical posterior direction relative to the user. As shown, for example, first and second posts 106, 108 are on the posterior side, and third and fourth posts 110, 112 are on the anterior side. An interior volume 130 may be defined by posts 106, 108, 110, 112 and rails 114, 116, 118, 120, 122, 124, 126, and 128. In use, a user's foot and/or leg may be disposed within interior volume 130, with the toes facing the anterior side of frame 102. Because a user may typically be seated when using apparatus 100, rail 126 (where provided) may be disposed at a lower height relative to rail 128 than rail 122 is disposed relative to rail 124 in order to allow the user's foot and/or leg to more easily access interior volume 130. Additionally, to facilitate user access to and control of apparatus 100, handles 132 may be disposed at upper ends of posts 106, 108 and wheels (e.g., casters, which may be 360-degree rotational or fixed) 134 may be disposed at lower ends of posts 106, 108, 110, and 112. Wheels 134 may allow the user to move and/or tilt the device around the user's appendage so that the stocking may be donned or doffed without the user having to flex his or her hip.

In use, a user may grasp handles 132 and roll, pivot, tilt or otherwise move apparatus 100 on wheels 134. The handles 132 may allow a seated user to move the device far enough and tilt it toward himself or herself such that the user may have adequate clearance of a loaded stocking's knee-level edge. This may allow the user to insert or withdraw the user's foot with minimal hip flexion. Of course, handles 132 and wheels 134 are not required in all embodiments. Further, and also to facilitate user access to and control of apparatus 100, posts 106, 108 may each have a telescoping portion defined at the upper ends thereof, e.g., beneath handles 132, such that the length of posts 106, 108 may be extended or retracted based on the height of a user.

In various embodiments, frame 102 may be made from any suitable material. In some embodiments, frame 102 may be formed from a high strength, lightweight material, such as a plastic or metal material, or a composite thereof. In the illustrated embodiment, various components of frame 102, including posts 106, 108, 110, 112 and rails 114, 116, 118, 120, 122, 124, 126, and 128, may be formed from lengths of cylindrical PVC tubing and connectors (e.g., couplings, tees, 2-, 3-, and 4-way elbows, etc.). In other embodiments, aluminum tubing, among other materials, could be used. In various embodiments, such components may have any suitable cross-sectional shape and may be solid or hollow. Likewise, in various embodiments, each frame element or component may be unitary or may itself comprise multiple individual components or elements. Also, in some embodiments, multiple frame elements may be replaced by walls or panels; for instance, individual rails 122 and 124 and posts 110 and 112 could be replaced by a single wall or panel in some embodiments. Where, as shown, components of frame 102 are formed of a plastic material, a chain 136 or another suitable grounding device may be coupled with a portion of frame 102. Here, chain 136 is shown coupled with rail 124. As those of skill in the art will appreciate, chain 136 may be allowed to contact the surface on which apparatus 100 is disposed, and it may be useful to discharge and/or avoid the buildup of static electricity.

Additionally, in the illustrated embodiment, frame 102 may comprise a fifth post 138 movably coupled between rails 114 and 118 and a sixth post 140 movably coupled between rails 116 and 120. In this regard, fifth post 138 may comprise a first coupling 142 (e.g., a 4-way elbow) at an upper end thereof and a similar second coupling 144 at a lower end thereof. Couplings 142 may each have at least one bore defined therethrough sized to slidably receive rails 114, 118. Thereby, fifth post 138 can be slid along rails 114, 118 in a direction parallel with the longitudinal axes of rails 114, 118 (or, e.g., toward and away from the anterior and posterior sides of frame 102). Sixth post 140 can be similarly movably coupled between rails 116 and 120 via couplings 146 and 148, respectively, such that sixth post 140 can be slid along rails 116, 120 in a direction parallel with the longitudinal axes of rails 116, 120 (or, e.g., toward and away from the anterior and posterior sides of frame 102). In various embodiments, posts 138 and 140 and couplings 142, 144, 146, and 148 may define or be a part of a sub-frame that is movable or slidable relative to other components of frame 102. Although slidable attachment of posts 138 and 140 between rails 114, 116, 118, and 120 is described via couplings 142, 144, 146, and 148 in this embodiment, those of skill in the art will appreciate that many other methods for facilitating slidable attachment (e.g., rollers, bearings, a track defined in each rail, etc.) may be used in other embodiments, and a coupling that surrounds each rail 114, 116, 118, and 120 need not be used in all embodiments.

In various embodiments, apparatus 100 may comprise one or more linear actuators. The one or more linear actuators may be operative to cause movement of one or more clasp members coupled with the movable sub-frame relative to one or more other clasp members coupled with the stationary portions of frame 102 (e.g., base portion 104) in or along one or more directions (e.g., the anatomical anterior-to-posterior direction). In some embodiments, posts 138, 140 (along with any associated clasp members) may be movable (either together or independently) between a first, retracted position and a second, extended position, the latter being shown in FIG. 5. As described herein, a stocking (or portions or sleeves thereof) may be coupled between two or more such clasp members such that actuation of the linear actuator(s) stretches and relaxes an opening defined in the stocking. The clasp members are described in greater detail below.

In the embodiment shown in FIGS. 5-7, four linear actuators 150 are provided. As shown, in this embodiment, two linear actuators 150 may be coupled between post 106 and post 138, and two linear actuators 150 may be coupled between post 108 and post 140. Other arrangements are contemplated, though, and examples are described herein. In some embodiments, only one linear actuator 150 may be provided between each of posts 106, 138 and posts 108, 140. In general, linear actuators 150 may be disposed below rails 114 and 116 and above rails 118 and 120, though again any suitable configuration is within the scope of various embodiments. In some embodiments, linear actuators 150 may be disposed within a suitable housing such that they are not ordinarily visible to a user.

In this embodiment, linear actuators 150 are dual-acting pneumatic cylinders, though as noted above, any suitable linear actuator may be used. As described in more detail herein, linear actuators are in fluid communication with a drive mechanism 152, which in this embodiment may comprise a positive pressure air pump. Drive mechanism 152 may be disposed in any suitable location on apparatus 100 in various embodiments, but as shown, drive mechanism 152 is coupled with a projection 154 extending from handle 132. As a result, a user may have ready access to drive mechanism 152 to control the operation of apparatus 100. In some embodiments, more than one drive mechanism 152 may be provided. In various embodiments, a control panel or box 156 may be coupled with and/or operatively connected to drive mechanism 152. Control panel 156 may be operative to selectively actuate one or more valves as described herein.

The operation of one embodiment of a drive mechanism 152 and control panel 156 is described with further reference to FIGS. 8-12. Turning first to FIGS. 5-6, 8, and 12, as noted above, drive mechanism 152 in this embodiment comprises a positive pressure air pump 158 having a cylindrical housing. Air pump 158 may have an on/off button 160 disposed on the housing. In various embodiments, air pump 158 may be a battery operated and/or rechargeable pump that is available as an independently attachable component. Drive mechanism 152 may further comprise a support structure for pump 158 and control panel 156 comprising a post 162 coupled with a ring 164. In this regard, post 162 defines a pair of slits 166 therethrough, and pump 158 in this embodiment is coupled with post 162 via a strap 168 that encircles the housing of pump 158 and which passes through slits 166 such that the housing of pump 158 is held fast against post 162. Additionally, the support structure of drive mechanism 152 may be coupled with apparatus 100 via ring 164. For example, projection 154 may have a depending portion 170, and ring 164 may be sized to be snugly received and/or tightened over depending portion 170 in one embodiment (best seen in FIGS. 6 & 12). In this embodiment, depending portion 170 may define an aperture therein, and a stopper (formed, e.g., of a suitable rubber material) 172 may be disposed within the aperture. As described in more detail below, air pump supply tubing 174 may extend downstream of stopper 172 to control panel 156, and it may be fluidically coupled with air pump 158 upstream of stopper 172, for example through projection 154.

Control panel 156 in this embodiment comprises a valve box 176. Valve box 176 may comprise a generally rectangular housing in which a valve assembly 178 is disposed, as described herein. In general, air pump supply tubing 174 may enter valve box 176 (e.g., through a lateral side thereof, as shown in FIGS. 8 & 11, or a bottom side thereof, as shown in FIGS. 5-7 & 12) and may be in fluid communication with valve assembly 178. Contraction side supply/exhaust tubing 180 and expansion side supply/exhaust tubing 182, both of which also are in fluid communication with valve assembly 178 at an upstream end thereof, may exit valve box 176 on another lateral side thereof and extend to respective contraction and expansion sides of the one or more linear actuators 150 of apparatus 100. Tubing 174, 180, and 182 may, in various embodiments, be formed of a material that does not expand significantly in volume during use in order to better transfer the pressure between air pump 158 and linear actuators 150, such as but not limited to PTFE, polyurethane, or silicone materials.

Valve box 176 may comprise a cover in some embodiments, for example having a left side 184 and a right side 186. An aperture 188 can be defined through cover left and right sides 184, 186 such that a rotatable selector post 190 of valve assembly 178 may extend therethrough. An upper end 192 of selector post 190 may be disposed above the cover of valve box 176, and a lower end 194 (FIG. 10) of selector post 190 may be disposed within valve box 176. A selector tab 196 may project from post 190 at upper end 192 thereof and is therefore accessible to and actuatable by a user, for example to actuate a valve of valve assembly 178. As described herein, actuation of the valve can cause air supplied from pump 158 to switch from supplying air to expansion side supply tubing 182 (which, in turn, causes expansion of a linear actuator 150) to supplying air to contraction side supply tubing 180 (which, in turn, causes contraction of the linear actuator 150). Although a manually operated tab 196 is shown for actuating a valve of valve assembly 178 in certain embodiments, in other embodiments, valve assembly 178 can instead comprise an automatic valve.

Referring now also to FIGS. 9-11, in one embodiment valve assembly 178 further comprises a valve member 198 that projects from post 190. (In use, valve member 198 may be disposed within valve box 176, but to facilitate illustration, valve box 176 is not shown in FIGS. 9-10.) Valve member 198, which may rotate with selector post 190, may take various forms in various embodiments, but in the illustrated embodiment valve member 198 may be a generally rectangular body that is adapted to engage with and selectively compress supply and exhaust tubing, as described herein, based on the position of selector tab 196 to control the flow of air in the system.

A block 200 is disposed at lower end 194 of selector post 190 and also is adapted to rotate with selector post 190 in response to movement of selector tab 196. For example, as shown in FIG. 10, in some embodiments, lower end 194 of selector post 190 may define a rectangular portion 207 that is received in a similarly shaped recess 209 defined in block 200. In any event, block 200 may have an aperture 201 defined therein in which a bolt 202 (or another suitable fastener, pin, or the like) is rotatably received. In other words, bolt 202, the head of which is visible in FIG. 9, may rotate with respect to block 200. One end of a spring 204 can be coupled with the shaft of bolt 202 and is secured therewith via a suitable nut 206 (e.g., an acorn nut). The other end of spring 204 can be coupled with the shaft of another bolt 208 and secured therewith via a nut 210. In the illustrated embodiment, spring 204 may be a helical tension spring. Those of skill in the art can select a suitable spring 204 that exerts force sufficient to cause valve member 198 to compress the tubing portions described below when pressed against them.

As best seen in FIG. 11, bolt 208 passes through an aperture 212 defined in valve box 176 in this embodiment. Thus, while bolt 208 may be rotatable with respect to valve box 176, bolt 208 is restrained from other movement with respect to valve box 176. It is noted that these components are not visible in FIG. 12 for the sake of simplifying that figure. In some embodiments, however, these components may also be disposed within valve box 176 such that they are not visible to the user.

Accordingly, and as those of skill in the art will appreciate, these components of valve assembly 178 may operate in a manner analogous to an over-center linkage. For instance, when post 190 is rotated via tab 196 such that block 200 moves "over center" (e.g., wherein the "center" point may be the point at which a longitudinal axis of block 200 is generally parallel with one of the short sides of valve box 176 as seen in plan in FIG. 8) from the right-hand side (e.g., the cover 186 side) of valve box 176 to the left-hand side (e.g., the cover 184 side) of valve box 176, tension spring 204 may apply a force to bolt 202 and, correspondingly, to block 200 and post 190, that causes post 190 to rotate to the left. As a result, valve member 198 is pulled in the same direction of rotation, and the force of spring 204 will hold valve member 198 in place against supply and exhaust tubing, causing compression thereof sufficient to block the passage of air therethrough, until a user causes tab 196 to rotate back over center, e.g., to cause expansion of one or more linear actuators 150.

In that regard, one example of a portion of a fluid circuit defined within valve box 176 is described with reference to FIGS. 9-10. As noted, in this embodiment, pump 158 is adapted to supply air to supply tubing 174, which passes into valve box 176. Within valve box 176, supply tubing 176 may be in fluid communication with one branch of a wye fitting 214, the other branches of which are respectively fluidly connected with an upstream end of first internal supply tubing 216 and an upstream end of second internal supply tubing 218. One branch of a second wye fitting 220 is coupled with an upstream end of expansion side supply/exhaust tubing 182, and one branch of a third wye fitting 222 is coupled with an upstream end of contraction side supply/exhaust tubing 180. The downstream end of first internal supply tubing 216 can be coupled with another branch of wye fitting 220, and the downstream end of second internal supply tubing 218 can be coupled with another branch of wye fitting 222. Additionally, the third branch of wye fitting 220 is coupled with an upstream end of a first internal exhaust tubing 224, and the third branch of wye fitting 222 is coupled with an upstream end of a second internal exhaust tubing 226. The downstream ends of first and second internal exhaust tubing 226 respectively are coupled with an exhaust port 228. As best seen in FIG. 12, exhaust port 228 may extend from and vent to the exterior of valve box 176. In some embodiments, a filter for microbial particles may be disposed within exhaust port 228. Such a filter may reduce the dispersion of microbes, for example which may be disposed in lubricant fluid, into the air that a user may breathe.

Based on the user's selection of the position of tab 196, valve member 198 may selectively block internal tubing to cause expansion or contraction of the linear actuator(s) to which air pump 158 is fluidly coupled. For instance, as shown in FIG. 9, tab 196 is positioned such that valve member 198 is disposed against internal supply tubing 216 and internal exhaust tubing 226. In use, the force of spring 204 causes valve member 198 to compress tubing 216 and 226 to block airflow therethrough. Thus, with valve member 198 in this position, air entering from supply tubing 174 will flow through internal supply tubing 218, through wye fitting 222, and out of valve box 176 via contraction side supply/exhaust tubing 180. Because of the position of valve member 198, air will not flow through internal supply tubing 216 in this example. Tubing 180 extends along and/or within frame 102 such that it is (or branches thereof are) in fluid communication with contraction side port(s) (FIGS. 19-20) of the linear actuator(s) 150. As a result, with valve member 198 in this position, the linear actuator(s) 150 will contract, causing movement, e.g., of posts 138 and 140 away from the position shown in FIG. 5 in a direction parallel with the longitudinal axes of rails 114, 116 (e.g., in a posterior direction). As the linear actuator(s) 150 contract, air will be pushed out of an expansion side port in the linear actuator(s) 150 that is coupled with a terminal end of each branch of expansion side supply/exhaust tubing 182. Air will return to valve box 176 via tubing 182 and will flow through internal exhaust tubing 224 to exit exhaust port 228. Again, because of the position of valve member 198, exhaust air will not flow through internal exhaust tubing 226 in this example.

Similarly, if tab 196 is repositioned such that valve member 198 is disposed against internal supply tubing 218 and internal exhaust tubing 224, the opposite flow will occur and linear actuator(s) 150 will expand. Specifically, the force of spring 204 will cause valve member 198 to compress tubing 218 and 224 to block airflow therethrough. Thus, with valve member 198 in this position, air entering from supply tubing 174 will flow through internal supply tubing 216, through wye fitting 220, and out of valve box 176 via expansion side supply/exhaust tubing 182. Because of the position of valve member 198, air will not flow through internal supply tubing 218 in this example. Tubing 182 likewise extends along and/or within frame 102 such that it is (or branches thereof are) in fluid communication with expansion side port(s) (FIGS. 19-20) of the linear actuator(s) 150. As a result, with valve member 198 in this position, the linear actuator(s) 150 will expand, causing movement, e.g., of posts 138 and 140 to the position shown in FIG. 5. As the linear actuator(s) 150 expand, air will be pushed out of a contraction side port in the linear actuator(s) 150 that is coupled with a terminal end of each branch of contraction side supply/exhaust tubing 180. Air will return to valve box 176 via tubing 180 and will flow through internal exhaust tubing 226 to exit exhaust port 228. Again, because of the position of valve member 198, exhaust air will not flow through internal exhaust tubing 224 in this example.

In other embodiments, rather than using a positive pressure air pump for both contraction and expansion of a linear actuator, an air pump could be used for expansion in conjunction with a vacuum pump used for contraction. Rather than employing the valve assembly described above, such an embodiment may be used with a simple 3-way valve familiar to those of skill in the art. Alternatively, some embodiments may employ oppositely-oriented single-acting linear actuators that are selectively operated via an air pump or vacuum pump to expand and contract a sub-frame relative to a base portion of the frame. Further, in various embodiments, more than one type of linear actuator may be used with and/or provided on an apparatus for donning and/or doffing a stocking. Those of skill in the art will appreciate that many other arrangements are contemplated.

Based on the above, it will be appreciated that tubing portions 216, 218, 224, and 226 are selected from materials that are compressible as a result of the force applied thereto by valve member 198 and spring 204 to a degree that is sufficient to block the passage of air therethrough. In various embodiments, these tubing portions may be formed of a soft rubber material. Those of skill in the art can select suitable tubing for this purpose.

As noted above, in various embodiments, apparatus 100 may be provided with one or more clasp members. The clasp members may be adapted for engagement with a portion or sleeve or other attachment mechanism of a stocking (see, e.g., FIGS. 2-4), such that movement of posts 138, 140 in response to actuation of linear actuators 150 will cause expansion and contraction of an opening defined in the stocking. In general, apparatus 100 may have at least one clasp member coupled with a stationary portion of frame 102, e.g., with posts 106 or 108, and at least one clasp member coupled for movement with either or both of posts 138 and 140. In various embodiments, however, more clasp members may be provided. In some embodiments, the number of clasp members may correspond to the number of sleeves available on the type of stocking that is to be used with apparatus 100. In some embodiments, clasp members may not engage with a sleeve on a stocking at all (and the stocking may not be provided with such sleeves), and the number of clasp members provided is a number sufficient to suitably expand and contract an opening defined in the stocking.

Certain embodiments of clasp members in accordance with embodiments of the present invention are described below with reference to FIGS. 5-7 and 13-18. Apparatus 100 in this example comprises eight clasp members. More particularly, four such clasp members are in the form of carabiners 230. As shown, one carabiner 230 is coupled with each of posts 106, 108, 138, and 140 at locations above rails 114 and 116, though this is not required in all embodiments. Carabiners 230 may be used to engage with sleeves of a stocking that are proximate the level of a user's knee (e.g., disposed at a proximal end of the stocking). In other embodiments, S-hooks or other suitable clasp members may also be used in place of carabiners 230. In some embodiments, such clasp members may be lined with a rubber material to reduce the likelihood of detachment from a stocking.

Additionally, apparatus 100 in this example comprises two anterior clasp members 232 and two posterior clasp members 234. Each anterior clasp member 232 is coupled with a respective post 138, 140 and movable therewith. In the illustrated embodiment, each anterior clasp member 232 is disposed proximate a lower end of each of posts 138, 140. Each posterior clasp member 234 is coupled with a stationary portion of frame 102. In one embodiment, a posterior clasp member 234 may be coupled with rails 126, 128 and/or posts 106, 108. In the illustrated embodiment, frame 102 additionally comprises posts 236, 238, each of which extends between rails 126 and 128, and each posterior clasp member 234 is coupled with a respective post 236, 238. Posterior clasp members 234 may be coupled with posts 236, 238 proximate the lower ends thereof, or at a location generally co-planar with anterior clasp members 232. Clasp members 232 and 234, which may be used to engage with sleeves of a stocking that are proximate the level of a user's ankle, are described in greater detail below. In various embodiments, clasp members 232, 234 may be adjustable in height along posts 106, 108, 138, and 140.

Although the illustrated embodiment includes carabiners at one level and different types of anterior and posterior clasp members at another level, those of skill in the art will appreciate that, in various embodiments, any type of clasp member may be provided at any level of or location on the device, and not all clasp members of a similar type need be disposed at the same level or location as other such clasp members. Likewise, in some embodiments, clasp members may only be disposed at one level or location, may be disposed at two different levels or locations, or may be disposed at three or more different levels or locations.

In various embodiments, both anterior clasp members 232 and posterior clasp members 234 may comprise a static component that is adapted to engage with a portion of a stocking, such as a sleeve thereof, to facilitate stretching and relaxation of the stocking. In one embodiment, such a static component may be in the form of a prong 240 that projects into interior volume 130 and that has a shaft 242 extending vertically from a horizontal projection 244. Prongs 240 in various embodiments may be formed of a rigid material, such as steel or hardened plastic.

In some embodiments, it is contemplated that introducer pegs may be coupled with shafts 242 of prongs 240. Such introducer pegs, which may be semi-rigid or flexible extensions of a prong 240 shaft 242, may assist a user with doffing a stocking and, in particular, with introducing a sleeve coupled with a stocking onto a shaft 242 of a prong 240. This may be useful, for instance, to accommodate different users' leg sizes or users with visual or motor impairments. The introducer pegs may extend vertically from shafts 242 and may each have a different height, which may allow a user to focus on introducing one shaft 242 into one sleeve at a time, rather than attempting to introduce all shafts 242 into all respective sleeves at one time. For instance, once one sleeve is connected with its respective introducer peg, a user may move his/her appendage into a different position to insert another introducer peg into another sleeve without fear that the previously connected sleeve(s) would have their associated prongs accidentally slip out of the sleeves. A user may insert a stocking sleeve over the tallest introducer peg first and then proceed through the other introducer pegs in order of reducing height, introducing a respective sleeve over the shortest introducer peg last.

Horizontal projection 244 may be coupled with a respective post 138, 140, 236, 238 by any suitable means. For example, horizontal projection 244 may extend through an aperture defined in each post 138, 140, 236, and 238, and prongs 240 may each have a depending shaft 245 that extends downward from horizontal projections 244, as illustrated in FIGS. 7 & 21-33, and which may be fixedly connected with each post. In various embodiments, suitable fasteners, zip ties, or the like, may be used. As will be appreciated, depending shaft 245 may provide additional strength and support to each clasp member. In some embodiments, depending shaft 245 may be coupled with horizontal projection 244 after horizontal projection 244 has been inserted through the aperture defined in each post. In other embodiments, the shaft 242, horizontal projection 244, and depending shaft 245 of prongs 240 may be formed integrally prior to assembly. In the latter case, to couple the prongs 240 with each post, each post may initially define an elongated aperture larger than the diameter of the horizontal projection 244 in order to allow prongs 240 to be inserted therethrough. After each prong 240 is fixed in place, the elongated aperture may or may not then be partially closed, or filled in, around horizontal projection 244.

As shown in the figures, in one embodiment, prongs 240 of anterior clasp members 232 may extend into interior volume 130 at an angle relative to the longitudinal axis of rails 114, 116, whereas prongs 240 of posterior clasp members 234 may extend into interior volume 130 in a direction parallel with the longitudinal axes of rails 114, 116, though this is not required. In some embodiments, the locations of prongs 240 when linear actuators 150 (and posts 138, 140) are in the contracted position may correspond generally to the locations of sleeves 38 of stocking 20 described above with reference to FIG. 3. In use, sleeves coupled with a stocking may be received over each prong 240 such that, when posts 138, 140 are moved from the contracted position to the expanded position, they cause the stocking to stretch open.

Although not required in all embodiments, in some embodiments, anterior clasp members 232 and/or posterior clasp members 234 may also have dynamic latch mechanisms that are adapted to retain a sleeve of a stocking in place on prongs 240 after the sleeves have been placed thereon. For example, in this embodiment, anterior clasp members 232 can comprise a bracket 246 that is adapted to be coupled with a post 138, 140. Here, bracket 246 defines a pair of angled flanges 248, 250, each of which defines an aperture therethrough. A suitable fastener, such as a pin or bolt 252, is coupled with bracket 246 via the apertures defined in flanges 248, 250. As a result of the angle and position of flanges 248, 250, bolt 254 may be angled in a generally posterior direction. A rod 254 can be rotatably coupled with (e.g., received over) a shaft of the bolt 252. Rod 254 can be rotatable from a first position, at which rod 254 engages bracket 246 (FIG. 17), and a second position, at which rod engages prong 240 (FIGS. 14 & 18). Due to the angled position of bolt 252, rod 254 may rotate thereabout in a generally upward direction. Thus, when engaging prong 240, rod 254 may apply a force in the superior and anterior anatomical directions. Rod 254 may also be normally biased toward the first position via a spring 256 that extends between bracket 246 and rod 254. In some embodiments, shaft 242 of prong 240 may define an overhang 258, beneath which is disposed an engagement surface 260, which in one embodiment is formed from a suitable resilient foam material.

Additionally, and for example, posterior clasp members 234 can comprise a latch member 262 rotatably coupled with prong 240. Although a variety of suitable configurations of latch member 262 are contemplated, in the illustrated embodiment, latch member 262 comprises a rectangular frame 264 that is rotatably coupled with a collar 266. Collar 266, which in one embodiment may comprise a nut or the like, may be coupled with either horizontal projection 244 or shaft 242 of prong 240, or both. In use, frame 264 of latch member 262 may rotate with respect to collar 266 and prong 240 from a first position, at which frame 264 may contact post(s) 238 and/or 108 (FIG. 15), and a second position, at which frame 264 engages prong 240 (FIGS. 14 & 16). Frame 264 may also be normally biased toward the first position via a spring 268. Again, shaft 242 of prong 240 may define an overhang 258, beneath which is disposed an engagement surface 260, which in one embodiment is formed from a suitable resilient foam material.

In various embodiments, each rod 254 of each anterior clasp members 232 and each latch member 262 of each posterior clasp member 234 may be independently rotatable. In some embodiments, rods 254 and latch members 262 may be rotatable simultaneously, for example in response to and, in some cases, proportionately to the extension/retraction of, linear actuators 150. One such embodiment is shown in the figures. Specifically, a cable 270 may be coupled with and extend between post 106 and post 138, and a cable 272 may be coupled with and extend between post 108 and post 140. Cable 270 has a distal end 274 that can be attached to a rod 254 of the anterior clasp member 232 that is coupled with post 138, and cable 272 has a distal end 276 that can be attached to a rod 254 of the anterior clasp member 232 that is coupled with post 140. As shown in the figures, in this embodiment the respective distal ends 274, 276 of cables 270, 272 extend around posts 138, 140 to attach to each rod 254. In various embodiments, the cables may be formed of a variety of suitable materials, such as synthetic nylon or PVDF materials that are stretch resistant (e.g., analogous to fishing line) so that they will transfer rather than absorb the force applied to them but be flexible enough to extend around posts 138 and 140. In some embodiments, the cables may also be formed of steel wire or another suitable material.

In addition, cable 270 has a proximal end 278 that can be attached to a frame 264 of the posterior clasp member 234 that is coupled with post 236, and cable 272 has a proximal end 280 that can be attached to a frame 264 of the posterior clasp member 234 that is coupled with post 238. Springs 282, 284 (or other suitable resilient members) may be coupled between respective cables 270 and 272 and each of posts 106 and 108. In some embodiments, springs 282, 284 may be integral with or otherwise form a part of cables 270, 272, and in other embodiments, springs 282, 284 may be separate components. In some embodiments, springs 282, 284 need not be provided at all. In various embodiments, the provision of springs 282, 284 may permit adjustment of the travel of posts 138, 140 and linear actuators 150 without the need to adjust the length of cables 270, 272. In other words, in some embodiments, springs 282, 284 may prevent slack in cables 270, 272 so that they do not sag when the posts 138, 140 are in the contracted position. In some embodiments, springs 282, 284 may be in a relaxed state when linear actuators 150 are in the contracted position. In some embodiments, springs 282, 284 may have a spring rate that is selected so that it does not overcome the tendency of springs 256 and 268 respectively to bias rods 254 and frames 264 toward the first positions described above.

Accordingly, and based on the above, when linear actuators 150 are actuated and move to the expanded position, causing posts 138 and 140 to move in a direction parallel with the longitudinal axes of rails 114, 116, such movement of posts 138, 140 will exert a pulling force on cables 270 and 272. This pulling force will cause rods 254 and frames 264 to move from their respective first positions to their respective second positions, for instance as shown in FIGS. 13-18. Those of skill in the art will appreciate that the above-described dynamic portions of anterior clasp members 232 and posterior clasp members 234 may be useful in the process of donning and/or doffing a stocking. For example, after a stocking (or, e.g., a sleeve thereof) is engaged with each prong 240 of clasp members 232 and 234, movement of rods 254 and frames 264 into engagement with each prong 240 will act to hold the stocking in place on each prong 240 while a user inserts and/or removes an appendage into/from the stocking. This may prevent inadvertent removal of the stocking from the prongs 240.

Other automated latch mechanisms and/or dynamic clasp members may be provided in other embodiments, for example to accomplish reversible catchment of sleeves of a stocking. For example, pneumatic pistons, inflatable durable balloons, servo motors, and/or electromagnetic connections all could be used, among others.

With reference to FIGS. 5 & 14, in some embodiments, the length or distance of travel of the sub-frame, or of posts 138, 140 along rails 114, 116 may be adjustable. This may be desirable, for example, to accommodate users of various sizes and to prevent posts 138, 140 and their associated clasp members from over-contracting, such that they come into contact with a user's appendage. In this regard, rails 114 and 116 may have a plurality of apertures 286 defined therein. A bolt 288 (or another suitable fastener) may be removably positioned in one such aperture on each rail 114, 116 such that the head of the bolt 288 is disposed above each rail 114, 116. Thereby, the contraction travel of posts 138 and/or 140 may be limited, in that during the process of contraction, a post 138 and/or 140 may interfere with the head of the bolt 288.

As noted above, a variety of linear actuators may be used in various embodiments of the present invention. Those of skill in the art are familiar with the operation of such linear actuators and can select suitable linear actuators based on the description herein. However, certain embodiments of a linear actuator in accordance with the present invention are discussed in detail with reference to FIGS. 19-20, both of which are partially exploded views.

In some double-acting pneumatic cylinders, friction between a piston head (which may be surrounded by an O-ring or the like) and the cylinder body can limit or prevent the device from moving. The amount by which movement is limited may depend on the air pressure applied. While it is possible to increase the air pressure applied, doing so may also require a larger air pump, which may not be desirable or practical in all embodiments. Accordingly, in certain embodiments, a linear actuator having a lubrication system that circulates lubricant during use may be provided.

For example, a linear actuator 150 may comprise a housing 300, which may be cylindrical in shape, that extends between a head cap 302 and an end cap 304. Within housing 300, a piston head 306 disposed at an end of a piston rod 308 may reciprocate in response to a gas (e.g., air) supplied via a contraction side port 310 and an expansion side port 312. Piston head 306, which may also be cylindrical in shape, may have an O-ring 307 disposed on an exterior surface thereof that is in contact with an internal surface of housing 300. Gas supplied into contraction side port 310 may fill a contraction chamber 314, causing movement of piston head 306 and rod 308 toward the position shown in FIGS. 19-20, and causing gas disposed in an expansion chamber 316 to be exhausted out of expansion side port 312. Likewise, gas supplied into expansion side port 312 may fill expansion chamber 316, causing movement of piston head 306 and rod 308 away from the position shown in FIGS. 19-20, and causing gas disposed in the contraction chamber 314 to be exhausted out of contraction side port 310. In various embodiments, a predetermined amount of lubricant 317 is provided within housing 300.

Additionally, linear actuator 150 may comprise either or both of an active lubrication system 318 and a passive lubrication system 320, or both. Also, in some embodiments, both the active lubrication system 318 and the passive lubrication system 320 may be disposed in each of contraction chamber 314 and expansion chamber 316. To facilitate explanation, however, in FIGS. 19-20, the active lubrication system 318 is disposed only within expansion chamber 316, and the passive lubrication system 320 is disposed only within contraction chamber 314.

In this embodiment, active lubrication system 318 comprises a lubrication tube 322 fluidly connected with port 312. Lubrication tube may be formed from a suitable flexible tubing material. Lubrication tube 322 may have a descending portion 324 extending downward along an interior surface of head cap 302 and a horizontal portion 326 extending laterally along the interior surface of head cap 302. An ascending portion 328 of lubrication tube 322 may be coupled with piston head 306 at a location proximate O-ring 307 but in a manner that does not cause ascending portion 328 to contact the interior surface of housing 300 during reciprocation of piston head 306. Due to the length and flexible nature of lubrication tube 322, ascending portion 328 is able to reciprocate with piston head 306 in some embodiments. Ascending portion 328 may have an outlet 330, and a plurality of apertures 332 may be defined in descending portion 324 and horizontal potion 326. A retention tube 334 may be disposed over descending portion 324 and may be secured via an adapter 336 that is connected between descending portion 324 and port 312. At its superior end, retention tube 334 may define an air-tight seal with adapter 336, and retention tube 334 may be open to and or reside within the lubricant 317 at its inferior end. In other words, the amount of lubricant 317 within housing 330 may cause it to be at a level that is above apertures 332 and the inferior end of retention tube 334. Further, a conduit band 338 may be disposed over piston head 306 on each side of O-ring 307. Conduit band 338 may have an outer diameter less than that of O-ring 307, such that conduit band 338 does not contact the interior surface of housing 300. Conduit band 338 may be formed of a suitable microfiber material to encourage wicking in some embodiments, and it may have anti-microbial properties (e.g., being embedded with silver).

In use, the active lubrication system 318 may operate as follows. A gas may enter expansion chamber 316 via port 312, adaptor 336, lubrication tube 322, and outlet 330. Lubricant 317 may have entered lubrication tube 322, for example, via apertures 332 in horizontal portion 326, either between strokes or at other parts of the cycle. As the gas enters, it may push lubricant 317 ahead of it and cause the lubricant to be deposited on conduit band 338. Conduit band 338 may transfer lubricant 317 to or around O-ring 307. During contraction, the gas exits expansion chamber 316 via outlet 330. The gas may encounter and push against some lubricant 317 in horizontal portion 326, and it may force some lubricant 317 into descending portion 324 as a result. Much of any such lubricant 317 may exit the descending portion 324 via apertures 332 defined therein. This lubricant 317 may be returned to expansion chamber 316 via the inferior end of retention tube 334, and air may exit tube 322 via port 312.

Thus, in various embodiments, active lubrication system 318 may reduce "running friction" between O-ring 307 and the interior surface of housing 300. Although the passive lubrication system 320 described below may help overcome initial, "break away" friction, much of any lubricant provided via passive lubrication system 320 may be wiped from the interior surface of housing 300 after the first stroke of piston head 306, and so in various embodiments, active lubrication may be needed or desired.

Next, in this embodiment, passive lubrication system 320 may comprise a strip 340 extending between piston head 306 and end cap 304. Strip 340 may be formed of a flexible material adapted to transfer lubricant 317 from the lower portion of housing 300, where the lubricant 317 may reside, and conduit band 338. Strip 340 may define an aperture 342 therein through which piston rod 308 may pass. In some embodiments, strip 340 may act to transfer lubricant 317 via capillary action or wicking. In some embodiments, strip 340 may be formed from a porous material. In some embodiments, strip 340 may be formed from a length of rope or a fabric material, and the material selected may be the same as that of conduit band 338 in some embodiments. In various embodiments, strip 340 may also define one or more fringes 344 coupled between strip 340 and conduit band 338.

In use, and particularly after linear actuator 150 has been at rest for some period of time, strip 340 may facilitate the transfer of lubricant 317 to conduit band 338. As a result, passive lubrication system 320 will provide additional lubricant to or around O-ring 307. This may reduce "break away" friction once use of linear actuator 150 is resumed, such that piston head 307 does not "stick" and impair the operation of actuator 150.

Additionally, as shown in FIG. 20, one or more lubricant drain(s) 346 may be provided in some embodiments. In this regard, stagnant fluid of any type may become colonized with microbes (fungi, bacteria, etc.) which may pose a health risk in some circumstances, in that the air that is exhausted from exhaust port 228 may be inhaled by a user. Thus, in addition to the filter in the exhaust port 228 described above, drain(s) 346 may be defined in housing 300 (for example, in each of expansion chamber 316 and contraction chamber 314) and fluidly coupled with valve(s) 348. Valves 348, which may normally be closed, may be actuated to drain lubricant 317 from housing 300. Regular changing of fluids may reduce the risk of microbe buildup.

Next, FIGS. 21-23 illustrate an apparatus 350 for donning and/or doffing a stocking according to another embodiment of the present invention. In this embodiment, apparatus 350 may be similar in many respects to apparatus 100, described above, and like reference numerals will be used to denote like parts. As described in more detail below, apparatus 350 comprises a single linear actuator 352, which in this embodiment can be a motor-driven screw, rather than one or more pneumatic cylinders as in apparatus 100. FIGS. 21 and 22 are perspective views of apparatus 350 wherein the posts 138, 140 are in a contracted position and anterior and posterior clasp members 232, 234 are in an open position. FIG. 23 is a perspective view of apparatus 350 wherein the posts 138, 140 are in an expanded position and anterior and posterior clasp members 232, 234 are in a closed position.

More particularly, in this embodiment, linear actuator 352 comprises a beam 354 that is coupled with posts 138, 140. Beam 354 preferably defines a threaded hole sized to receive a screw 356 (or threaded rod or the like). Screw 356 in this embodiment may be oriented generally horizontally, for example defining a longitudinal axis that extends generally parallel with the longitudinal axes of rails 114, 116. In this embodiment, a rail 358 can be disposed between posts 110, 112. Rail 358 may define a longitudinal axis that is parallel with the longitudinal axis of rail 122 in some embodiments, and in some embodiments, the longitudinal axes of rails 358, 122 may be on the same plane. A motor 360, which may be a DC electric motor in some embodiments, is coupled with rail 358 and is operatively connected with screw 356 to drive rotation thereof. In some embodiments, screw 356 may extend through an aperture defined in rail 358. In this embodiment, a power source 362 is provided in place of air pump 158 and is in electrical communication with motor 360 via suitable wiring 364. (In other embodiments, power source 362 may be provided in any suitable location on apparatus 350.) In one embodiment, power source 362 may comprise a battery or batteries. Further, in this embodiment, control panel 156 may comprise a suitable interface (e.g., analog or digital, including touchscreens and/or switches, etc.) for user control of motor 360 and, correspondingly, expansion and contraction of posts 138, 140 via screw 356.

In use, having connected a stocking to the clasp members 230, 232, 234 of apparatus 350, the user may select an expansion function on control panel 156. Selecting this function causes motor 360 to rotate screw 356 about its longitudinal axis in a first direction. The threads on screw 356 may engage with the threads in the aperture defined in beam 354 through which screw 356 passes. As a result, beam 354 will be drawn in a direction parallel with the longitudinal axis of screw 356 and/or of rails 114, 116, which may be an anterior-to-posterior anatomical direction. Control panel 156 may cause motor 360 to stop rotation of screw 356 after a predetermined and/or user-selected amount of time, degrees or number of rotations, length of travel of beam 354, change in electrical characteristics (e.g., a current level or resistance level), etc. As a result, posts 138, 140 will move with beam 354 from the position shown in FIG. 21 to the position shown in FIG. 23, in the process causing expansion or stretching of an opening defined in the stocking that is attached to clasp members 230, 232, 234. At this point, a user may either don or doff the stocking, depending on whether the user was wearing the stocking at the beginning of the operation. Once the stocking is donned or doffed, the user may select a contraction function on control panel 156. As will be appreciated, control panel 156 will cause motor 360 to operate and rotate screw 356 in a second direction opposite the first direction. Screw 356 will again engage with the threads in the threaded aperture defined in beam 354, and beam 354 and posts 138, 140 will travel from the position shown in FIG. 23 to FIG. 21. In the process, the opening defined in the stocking that is attached to clasp members 230, 232, 234 will relax or contract either to complete the donning process on a user's appendage or to allow the stocking to be removed from apparatus 350.

FIGS. 24-26 illustrate an apparatus 370 for donning and/or doffing a stocking according to another embodiment of the present invention. In this embodiment, apparatus 370 also may be similar in many respects to apparatus 100, described above, and like reference numerals will be used to denote like parts. As described in more detail below, apparatus 370 comprises two independently-actuatable linear actuators 372, 374 which in this embodiment can comprise automatically or manually driven screws, rather than one or more pneumatic cylinders as in apparatus 100. FIGS. 24 and 25 are perspective views of apparatus 370 wherein the posts 138, 140 are in a contracted position and anterior and posterior clasp members 232, 234 are in an open position. FIG. 26 is a perspective view of apparatus 370 wherein post 138 is in an expanded position and its associated anterior and posterior clasp members are in a closed position, while post 140 remains in a contracted position and its associated anterior and posterior clasp members remain in an open position.

More particularly, in this embodiment, linear actuator 372 comprises a screw 376 (or threaded rod or the like). Screw 376 can pass through apertures defined in posts 106, 138, and 110 and is rotatable with respect thereto. Screw 376 can be secured at its respective ends on either side of posts 106 and 110, for example via suitable nuts 378 or the like, to prevent longitudinal movement thereof. Linear actuator 374 comprises a similar screw 380 that passes through apertures defined in posts 108, 140, and 112 and is rotatable with respect thereto. Screw 380 can be secured at its respective ends on either side of posts 108 and 112, for example via nuts 378, to prevent longitudinal movement thereof. In this embodiment, screws 376, 380 may be oriented generally horizontally, for example each defining a longitudinal axis that extends generally parallel with the longitudinal axes of rails 114, 116.

Additionally, a suitable fastener adapted to engage with screws 376, 380 can be coupled with (e.g., embedded in) each of posts 138, 140. As shown, for example, a threaded bolt 382 may be received in the apertures defined in posts 138, 140, and screws 376, 380 may pass through the bolts 382 such that the threads of screws 376, 380 engage with the threads in bolts 382. Accordingly, and due to the movement constraints placed on screws 376, 380 and posts 138, 140, rotation of screws 376, 380 about their respective longitudinal axes will cause movement of posts 138, 140 therealong and along rails 114, 116, 118, and 120.

In various embodiments, linear actuators 372, 374 may be driven by any suitable drive mechanism familiar to those of skill in the art. In one embodiment, for example, each linear actuator 372, 374 may be driven manually by a knob, crank, or handle. In another embodiment, each linear actuator 372, 374 may be driven by an electric motor 384 adapted to interface with each screw 376, 380. In various embodiments, electric motor 384 may be any suitable electric motor, including a commercially available electric screw-drive. In some embodiments, a commercially-available 12V DC motor (e.g., employing a worm gear(s)) may be used as the electric motor(s) 384, and this motor may be actuated to rotate a respective screw 376, 380 via a double pole double throw (DPDT) 6-prong switch (e.g., of a three-position rocker type). Where this is the case, and just by way of example, the switches may be disposed on posts 106, 108 in a position accessible to the user, and a power source (e.g., a battery pack) in electrical communication with each motor may be disposed on rail 122.

In various embodiments, linear actuators 372, 374 each may be driven by a drive mechanism of the same type or each may be driven by a different type of drive mechanism. Likewise, in some embodiments, linear actuators 372, 374 may be driven by a single drive mechanism, rather than each being driven by a separate drive mechanism. In yet other embodiments, each linear actuator 372, 374 may be driven by more than one drive mechanism. For instance, linear actuator 372 may be driven at one end by a drive mechanism 384 that comprises a manual knob, and may be driven at the opposite end by the 12V DC motor described above, which may in such a case be coupled with post 110.

Additionally, in the illustrated embodiment, and in contrast to the embodiment described above with reference to FIGS. 13-18, flanges 248, 250 of brackets 246 in the anterior clasp members 232 are angled in a generally anterior direction. Rods 254 also are rotatable in a generally upward direction, as in the earlier embodiment, but in this embodiment rods 254 rotate from an anterior position toward the posterior of apparatus 370. Thus, when engaging prongs 240, rods 254 may apply a force in the superior and posterior anatomical directions. Also, in this embodiment, the distal ends of cables 270, 272 do not extend around posts 138, 140 to attach to each rod 254. Rather, in this embodiment, the distal ends of cables 270, 272 attach directly to rods 254. As a result, cables 270, 272 may be position more medially within interior volume 130 in this embodiment.

FIGS. 27-28 illustrate an apparatus 400 for donning and/or doffing a stocking in accordance with another embodiment of the present invention. In this embodiment, apparatus 400 also may be similar in many respects to apparatus 100, described above, and like reference numerals will be used to denote like parts. In this embodiment, apparatus 400 comprises a single linear actuator 402. Linear actuator 402 in this embodiment comprises a shaft 404 (or threaded or non-threaded rod or the like) driven by a drive mechanism 406, which may be an electric motor in this embodiment. In some embodiments, drive mechanism 406 may be analogous to an electric screw-drive, though any suitable drive mechanism 406 may be used in various embodiments. As shown, in this embodiment, shaft 404 is oriented vertically and, in some embodiments, its longitudinal axis may be generally parallel with the longitudinal axis of posts 106 and/or 108. Linear actuator 402 may be coupled with post 106 in this embodiment via a bracket 408. Shaft 404 may be at least partially disposed within a housing 410 (shown as transparent in the figures to facilitate illustration).

Linear actuator 402 is adapted to cause movement of posts 138, 140 in a direction parallel with the longitudinal axes of rails 114, 116 via rotation of shaft 404 about its longitudinal axis. In particular, linear actuator 402 in this embodiment also comprises an expansion cable 412 and a contraction cable 414. As best seen in FIG. 28, each of cables 412, 414 may be coupled with shaft by any suitable means (e.g., via a nut in one embodiment) such that rotation of shaft 404 causes cables 412, 414 to wrap about shaft 404.

In general, expansion cable 412 may extend between shaft 404, a pulley 416 disposed on post 110, a pulley 418 disposed on post 112, and posts 138, 140. Expansion cable 412 may define a first portion 420 that is coupled with post 138 and a second portion 422 coupled with post 140. In some embodiments, more than one expansion cable 412 may be provided. Additionally, in some embodiments, cable 412 may comprise one or more buffer springs 424, for example disposed between a distal end of each portion 420, 422 and a respective post 138, 140. Buffer springs 424 may be provided in some embodiments to allow shaft 404 to keep rotating in the event that one of posts 138, 140 has reached the end of its travel prior to the other of posts 138, 140. In this regard, if buffer springs 424 are not provided, and if posts 138, 140 do not reach the end of their travel simultaneously, it is possible that the shaft 404 will no longer be able to rotate, and one post 138 or 140 will not be able to move to its fully expanded position. In various embodiments, one or more holes, slots, or the like may be defined in housing 410 to allow passage of cable 412 therethrough.

Similarly, contraction cable 414 may extend between shaft 404, a pulley 426 coupled with post 106, a pulley 428 disposed on post 108, and posts 138, 140. Contraction cable 414 may also define a first portion 430 that is coupled with first post 138 and a second portion 432 coupled with post 140. Again, in some embodiments, more than one contraction cable 414 may be provided. Further, in some embodiments, cable 414 may comprise one or more buffer springs 424, for example disposed between a distal end of each portion 430, 432 and a respective post 138, 140. Cable 414 may also extend through the one or more holes, slots, or the like defined in housing 410 in some embodiments.

In use, a user may, for example via a forward/reverse button 434, actuate linear actuator 402. Drive mechanism 406 causes shaft 404 to rotate about its longitudinal axis in a direction corresponding to the user's selection. When the "forward" button is pressed, for example, shaft 404 may be rotated in a direction that causes cable 412 to wind around shaft 404 and that allows cable 414 to be unwound from shaft 404. As cable 412 is wound around shaft 404, it will exert a pulling force on the anterior sides of each post 138, 140, causing them to move in an anterior direction relative to the position shown in FIGS. 27-28, for example to the position shown in FIG. 30. Similarly, when the "reverse" button is pressed, for example, shaft 404 may be rotated in the opposite direction about its longitudinal axis to cause cable 414 to wind around shaft 404 and to allow cable 412 to be unwound from shaft 404. As cable 414 is wound around shaft 404, it will exert a pulling force on the posterior sides of each post 138, 140, causing them to move in a posterior direction to the position shown in FIGS. 27-28.

FIGS. 29-30 illustrate another embodiment of apparatus 400 wherein linear actuator 402 is manually operated in accordance with an embodiment of the present invention. In particular, in this embodiment, linear actuator 402 may comprise a knob 436 in place of drive mechanism 406. Knob 436 is adapted to rotate shaft 404 about its longitudinal axis. FIG. 29 shows posts 138, 140 in a contracted position, and FIG. 30 shows posts 138, 140 in an expanded position.

In this embodiment, linear actuator 402 may also comprise a knob rotation latch 438. Knob rotation latch 438 may comprise a latch member that, when lifted, may engage with a portion (e.g., a suitable recess or the like) of knob 436 to prevent rotation thereof. As a result, when the latch member is in the latched position, knob rotation latch 438 may retain posts 138, 140 in an expanded and/or contracted state.

FIGS. 31-33 illustrate an apparatus 450 for donning and/or doffing a stocking in accordance with another embodiment of the present invention. In this embodiment, apparatus 450 also may be similar in many respects to apparatus 100, described above, and like reference numerals will be used to denote like parts. As described in more detail below, apparatus 450 comprises two independently-actuatable linear actuators 452, 454, which in this embodiment can comprise automatically or manually scissor jacks, rather than one or more pneumatic cylinders as in apparatus 100. FIGS. 31 and 32 are perspective views of apparatus 450 wherein the posts 138, 140 are in a contracted position and anterior and posterior clasp members 232, 234 are in an open position. As best seen in FIG. 32, in this embodiment, anterior clasp members 232 and cables 270, 272 are analogous to those described above in the embodiment shown in FIGS. 24-26. FIG. 33 is a perspective view of apparatus 450 wherein post 138 is in an expanded position and its associated anterior and posterior clasp members are in a closed position, while post 140 remains in a contracted position and its associated anterior and posterior clasp members remain in an open position.

More particularly, in this embodiment, linear actuator 452 comprises a screw 456 (or threaded rod or the like) driven by a drive mechanism 458, which may be an electric motor. In some embodiments, drive mechanism 458 may be analogous to an electric screw-drive, though any suitable drive mechanism 458 may be used in various embodiments. Also, in other embodiments, linear actuator 452 may be driven manually by a knob, crank, or handle. As shown, in this embodiment, screw 456 is oriented vertically and, in some embodiments, its longitudinal axis may be generally parallel with the longitudinal axis of posts 106 and/or 108. Linear actuator 452 may be coupled with post 106 in this embodiment via a first bracket 460 and a second bracket 462. Bracket 460 can be stationary with respect to post 106, and bracket 462 is adapted to slide along post 106. In that regard, bracket 462 can also define a threaded aperture through which screw 456 extends such that, as screw is rotated about its longitudinal axis, bracket 462 travels upward and downward along post 106.

Actuator 454 preferably is constructed in a manner similar to actuator 452. Thus, for example, actuator 454 may comprise a screw 464 (or threaded rod or the like). Screw 464 may also be driven by an electric motor (not shown) or other suitable manual or automatic means. Linear actuator 454 may be coupled with post 108 in a manner similar to that by which linear actuator 452 is coupled with post 106. Linear actuator 454 also can comprise brackets analogous to those described above. For the sake of conciseness, only actuator 452 is described in additional detail below, but those of skill in the art will appreciate that such details also are applicable to actuator 454.

Linear actuator 452 preferably comprises first and second rods 466, 468. Rods 466, 468 may be any suitable rod in various embodiments, but as shown rods 466, 468 may be steel rods having a square cross-section. Rod 466 is pivotably coupled (e.g., via a suitable fastener) with bracket 462 at its proximal end, and its distal end is pivotably coupled with a bracket 470. Bracket 470 is coupled with a lower end of post 138 and may be fixed with respect thereto. Rod 468 in this embodiment is pivotably coupled (e.g., via a suitable fastener) with bracket 460 at the proximal end of rod 468, and the distal end of rod 468 is pivotably coupled with a bracket 472. Bracket 472 is coupled with post 138 and is adapted to slide with respect thereto. Rod 466 and rod 468 may also be pivotably connected together via a suitable fastener 474 in some embodiments.

In use, when post 138 is in the position shown in FIGS. 31-32, actuation of drive mechanism 458 causes screw 456 to rotate about its longitudinal axis. The threads on screw 456 engage with the threads defined in bracket 462, bracket 462 (and the proximal end of rod 466) to travel downward along screw 456. As will be appreciated, this movement forces the distal ends of rods 466 and 468 to move in an anterior direction, with the distal end of rod 468 sliding downward with bracket 472. As a result, post 138 is move to the position shown in FIG. 33. If the drive mechanism 458 is actuated to rotate screw 456 in the opposite direction about its longitudinal axis, the reverse will occur, and post 138 will return to the position shown in FIGS. 31-32. Linear actuator 454 operates in the same manner, but independently of actuator 452. Accordingly, a user may use the linear actuators 452, 454 of apparatus 450 to don and/or doff a stocking as described above.

FIGS. 34-35 illustrate an apparatus 500 for donning and/or doffing a stocking in accordance with another embodiment of the present invention. As described in more detail below, apparatus 500 may comprise a plurality of frame members that are expandable and contractible in two or more axial directions, such as both anterior-to-posterior and medial-to-lateral directions.

More particularly, apparatus 500 in this embodiment comprises a frame 502 comprising four posts 504, 506, 508, and 510. Posts 504 and 506 can have telescoping handles 512 attached at upper ends thereof for engagement by a user, and posts 504, 506, 508, and 510 may each have wheels or casters 514 coupled with their lower ends to facilitate movement of apparatus 500. Each of posts 504, 506, 508, and 510 may define a longitudinal axis, and in some embodiments, these longitudinal axes are parallel. In some embodiments, the longitudinal axes of posts 504 and 506 are coplanar, and likewise the longitudinal axes of posts 508 and 510, posts 504 and 508, and posts 506 and 510, respectively. First clasp members 516 can be coupled with each of the upper ends of posts 504, 506, 508, and 510. In the illustrated embodiment, first clasp members 516 are carabiners, clips, or the like, but any clasp member can be used in other embodiments. Additionally, second clasp members 518 can be coupled with each of the lower ends of posts 504, 506, 508, and 510. Second clasp members 518 are discussed in more detail below with reference to FIG. 35.

In apparatus 500, posts 504, 506, 508, and 510 can be coupled together via a plurality of sliding linkages. For example, extending between respective pairs of posts 504 and 506, 506 and 510, 504, and 508, and 508 and 510 can be a first rail 520 in telescoping engagement 522. In various embodiments, rails 520, 522 can have a non-circular cross-sectional shape (e.g., square, as shown, triangular, etc.). As a result, when posts 504, 506, 508, and 510 are expanded and contracted in various axial directions, rails 520, 522 will prevent twisting from occurring. In some embodiments, rails 520, 522 may extend between respective blocks 524 coupled with each post 504, 506, 508, and 510. Blocks 524 may be adjustable in height along each post in some embodiments, for example via a suitable fastener 526.

Additionally, apparatus 500 in this embodiment comprises linear actuators 528 disposed between respective pairs of posts 504 and 506, 506 and 510, 504 and 508, and 508 and 510. Linear actuators 528, which as shown may be single- or double-acting pneumatic cylinders, may be coupled at each end with a respective block 524. A drive mechanism 530, which may be a pump in this embodiment, is coupled with post 510 and in fluid communication with each actuator 528 via suitable tubing 532. A valve 534 fluidly coupled with tubing 532 may be used to control the supply of fluid to each actuator 528.

Each actuator 528 may define a longitudinal axis that is parallel with its direction of expansion and contraction. Each such longitudinal axis may, in various embodiments, be either coplanar or parallel with the planes on which lie the longitudinal axes of the posts between which each actuator 528 is disposed. The longitudinal axes of the actuators 528 between respective pairs of posts 504 and 506 and 508 and 510 may correspond to the medial-to-lateral anatomical direction relative to a user. The longitudinal axes of the actuators 528 between respective pairs of posts 506 and 510 and 504 and 508 may correspond to the anterior-to-posterior anatomical direction relative to the user.

In use, a user may first secure a stocking to apparatus 500 via clasp members 516 and 518. If the user is donning the stocking, the stocking may be secured to apparatus 500 by itself. If the user is doffing a stocking that the user is already wearing, then the user may grasp handles 512 and position his or her appendage within the area defined by posts 504, 506, 508, and 510 and rails 520, 522 prior to securing the stocking to the clasp members 516, 518. In any event, a user may then actuate drive mechanism 530 and/or valve 534 to cause fluid (e.g., air) to be supplied to linear actuators 528, which causes actuators 528 to expand along their longitudinal axes. As a result, posts 506 and 510 may move laterally relative to posts 504 and 508 (i.e., away from the position shown in FIG. 34). Likewise, and in some cases simultaneously, posts 508 and 510 may move in an anterior direction relative to posts 504 and 506 (i.e., away from the position shown in FIG. 34). Thus, the medial-to-lateral and anterior-to-posterior distances between the clasp members 516 and 518 will be increased, and the stocking will be stretched open in both of these directions. As a result, the user may easily insert into or remove from the stocking his or her appendage.

After the stocking has been donned and/or doffed, a user may actuate drive mechanism 530 and/or valve 534 to cause linear actuators 528 to return to the contracted position shown in FIG. 34. In some embodiments, such as those where linear actuators 528 are double-acting pneumatic cylinders, valve 534 may be actuated to direct fluid (e.g., air) to tubing fluidly connected to contraction sides of linear actuators 528. In other embodiments, each linear actuator 528 may be single acting and, for example, spring-loaded, such that drive mechanism 530 may simply be turned off and/or valve 534 may simply be closed or turned to an exhaust position in order to allow linear actuators 528 to return to their contracted positions in response to the force supplied via their respective springs. Those of skill in the art will appreciate that may other configurations are within the scope of the present invention.

As best seen in FIG. 35, second clasp members 518 in this embodiment each may be rotatable between first and second positions depending on whether a user of apparatus 500 is donning or doffing a stocking. More particularly, second clasp members 518 in this embodiment comprise a bracket 536 coupled with a respective post 504, 506, 508, and 510. Each bracket 536 may be translatable along each post, e.g., to adjust the height thereof, and may be secured in place with a removable fastener 538. A projection 540 projects from each bracket 536. Each projection 540 may define an aperture therethrough adapted to receive a stem 542 of a spring-loaded latch 544.

The distal ends of each stem 542 may support a prong 546 that is rotatable into the upward or vertical position, as shown, when a user is doffing a stocking, and a prong 548 that is rotatable from the position shown into the upward or vertical position when a user is donning a stocking. In particular, when clasp member 518 is in the first position shown in FIG. 35, a stocking's attachment mechanism (e.g., a sleeve) may be passed over each prong 546. When the user begins to remove his or her appendage from the stocking, any upward force imparted to the stocking will cause the attachment mechanism of the stocking to engage a depending arm 550 of prong 546. As a result, prong 546 may help retain the stocking in place on apparatus 500 as the user removes his or her appendage from the stocking. On the other hand, when a user desires to don a stocking, each latch 544 may be depressed and each stem 542 may be rotated (e.g., 180 degrees about its longitudinal axis) such that each prong 548 is disposed in the upward position. Prongs 548 do not comprise a depending arm in this embodiment. As a result, after a stocking has been donned, the user may easily remove his or her appendage with the stocking thereon from each clasp member 518 without resistance from prongs 548.

FIG. 36 is a schematic representation of an apparatus 600 for donning and/or doffing a stocking in accordance with another embodiment of the present invention. In FIG. 36, apparatus 600 is shown adjacent to a user 602 who may use apparatus 600 to don and/or doff a compression stocking. In this embodiment, apparatus 600 may be similar in many respects to apparatus 500, described above, except that here apparatus 600 is adapted to expand and contract in a third axial direction. The third axial direction may be the superior-to-inferior anatomical direction relative to a user 602.

More particularly, in this embodiment, apparatus 600 may comprise additional linear actuators 604 adapted to raise and lower apparatus 600 relative to a surface on which apparatus 600 is disposed. As shown, actuators 604, which may be analogous to actuators 528 described above, can be coupled with the lower ends of each of posts 504, 506, 508, and 510. Actuators 604 may each define a longitudinal axis that may be parallel with the longitudinal axis of each post. In other embodiments, actuators can be partially disposed within each post 504, 506, 508, and 510 and comprise, for example, piston rods that expand and retract from each post. Apparatus 600 may also be provided with additional tubing 606 in fluid communication with each actuator 604 and operative to facilitate expansion and/or contraction thereof via a suitable pump (not shown in FIG. 36). Of course, in other embodiments, linear actuators 604 need not be pneumatic cylinders and any suitable linear actuator may be used.

As will be appreciated from FIG. 36, some users 602 (particularly those with physical impairments and/or limited flexibility) may not be able to easily reach clasp members 516, 518 to load a stocking thereon when apparatus 600 is in its lowered position. Accordingly, and prior to donning a stocking, the user 602 may first actuate linear actuators 604 (for example, as described above) to cause linear actuators 604 to move from a retracted position to the expanded position shown in FIG. 36. In particular, the piston rods of actuators 604 may extend and press against the surface on which apparatus 600 is disposed, causing apparatus 600 to rise to a level that the user may more easily access clasp members 516 and 518. The user may then load a stocking onto the clasp members of apparatus 600 and cause apparatus 600 to be lowered back to the ground for the donning process. The user may operate actuators 604 via any suitable interface accessible to the operator. In various embodiments, the interface may include valves and/or power buttons that are, in turn, in communication with motor(s), pump(s), and/or vacuum(s) and with a suitable source of power.

Additionally, to ease an operator's ability to view and manipulate the various clasp members, a mirror may be disposed at an appropriate location on an apparatus for donning and/or doffing a stocking in various embodiments. For example, a mirror could be positioned on rail 122 and angled generally downward in some embodiments so that a user facing mirror 122 can better see clasp members 232, 234.

Embodiments of certain auxiliary devices that may be used in conjunction with an apparatus for donning and/or doffing a stocking in accordance with embodiments of the present invention are discussed below with reference to FIGS. 37-41. Certain auxiliary devices may be used to guide an un-clad stocking onto clasp members of an apparatus for donning and/or doffing a stocking as described herein. Certain other devices may be used with an already-clad stocking, and certain devices may be used to lower and/or lift an apparatus for donning and/or doffing a stocking.

For example, with reference to FIGS. 37-38, one embodiment of a guiding apparatus 610 is shown. In general, guiding apparatus 610 may be useful with a stocking having sleeves, as described above, that are coupled with one or more prongs associated with an apparatus for donning and/or doffing a stocking. As described below, guiding apparatus 610 may be used by a user who cannot lean or bend over to couple a stocking to the clasp members of the apparatus in preparation for donning a stocking. Guiding apparatus 610 may help guide the sleeves of a stocking onto the prongs and then may be withdrawn, leaving the stocking's sleeves on the prongs.

In this regard, guiding apparatus 610 in this embodiment comprises posts 612, 614, 616, and 618 which are oriented generally vertically and have a length sufficient to allow a user to manipulate guiding apparatus 610 as described herein, even, for example, when the user is seated. Likewise, posts 612, 614, 616, 618 preferably are formed from a suitable strong but lightweight material (e.g., a lightweight metal or plastic material, which may be non-magnetic, such as PVC) that can be readily lifted and manipulated by a user. Each post 612, 614, 616, 618 may define a longitudinal axis, and in some embodiments, these longitudinal axes are parallel. Posts 612, 614, 616, 618 may correspond in number to the number of clasp members associated with the apparatus for donning and/or doffing the stocking, and in other embodiments more or fewer than four such posts can be provided. Additionally, posts 612, 614, 616, 618 may each define an opening (e.g., a bore or recess) 620 at their distal ends, and in some embodiments, posts 612, 614, 616, 618 may be hollow along their length.

Posts 612, 614, 616, 618 may be coupled together at their respective proximal ends via a cross member 622 in one embodiment. Cross member 622, which may or may not be biaxially symmetric, may also serve as a handle for a user, though in other embodiments a separate handle may be provided. Posts 612, 614, 616, 618 are positioned relative to one another such that openings 620 may be received over the prongs (e.g., prongs 240) of an apparatus for donning and/or doffing a stocking when the respective clasp members are in a contracted position. Thus, as shown for example in FIG. 38, the distance between longitudinal axes of posts 612 and 618 (e.g., along a plane that contains both axes) may be less than the distance between longitudinal axes of posts 614 and 616 (e.g., along a plane that contains both of their longitudinal axes). As a result, posts 612 and 618 may be positioned to be received over the prongs 240 of posterior clasp members 234 in one embodiment, and posts 614 and 616 may be positioned to be received over the prongs 240 of anterior clasp members 232 in one embodiment (see FIG. 13). Openings 620 correspondingly have a diameter or size sufficient to receive such prongs therein.

Additionally, a chain 624 (or rope or the like) may be coupled with cross member 622 at its proximal end. A carabiner 626 (or clip, hook, or the like) may be coupled with chain 624 at its distal end. As described below, chain 624 and carabiner 626 may be used to support a stocking in the upright position while guiding apparatus 610 is being used. In some embodiments, and for example to provide additional stability and strength, a rail 628 may be coupled between posts 612 and 618, a rail 630 may be coupled between posts 612 and 614, a rail 632 may be coupled between post 614 and post 616, and a rail 634 may be coupled between post 616 and 618.

Use of guiding apparatus 610 in accordance with an embodiment of the present invention may be as follows. The description below assumes a stocking analogous to stocking 20 is used (including magnetic discs 42) with an embodiment of apparatus 100. First, a user may turn guiding apparatus 610 (e.g., upside down) and load the sleeves of the stocking that are located at a lower level (e.g., at the ankle level) onto respective posts 612, 614, 616, and 618. The user may also attach a sleeve or a portion of the stocking that is at a higher level (e.g., at the knee-level) to the carabiner 626. The user may then return guiding apparatus 610 to its upright position, such that the stocking is hanging from carabiner 626 and the stocking's sleeves are disposed around each of posts 612, 614, 616, and 618.

Next, the user may position the guiding apparatus 610 above the interior volume 130 and lower posts 612, 614, 616, and 618 into interior volume 130. The user may continue to lower guiding apparatus 610 until posts 612, 614, 616, and 618 are received over respective prongs 240 of the anterior and posterior clasp members 232, 234. The magnetic discs 42 may then be attracted to and contact the respective clasp members. The user may then detach the stocking from carabiner 626 and begin to withdraw the guiding apparatus 610. As the user does so, the magnetic discs 42 may hold the stocking in place while posts 612, 614, 616, and 618 are removed from the stocking's sleeves. Accordingly, once the guiding apparatus 610 is removed from interior volume 130, the stocking remains in place with its sleeves disposed over respective prongs 240. The user may then connect any additional clasp members to the stocking, if appropriate, and use the apparatus 100 to don the stocking as described herein.

In some embodiments, magnetic discs 42 are not required. Rather, a user may use a reach extender or the like to hold the stocking in position while simultaneously removing the guiding apparatus 610.

Turning now to FIG. 39, an embodiment of a lifting apparatus 650 is shown. As noted above, some users 602 (particularly those with physical impairments and/or limited flexibility) may not be able to easily reach clasp members to load a stocking thereon. Lifting apparatus 650 may be used to lift the apparatus for donning and/or doffing a stocking (e.g., apparatus 100 or any other such apparatus described or contemplated herein), for example where such apparatus is not provided with linear actuator(s) to vertically raise and lower the apparatus relative to the user. Apparatus 650 may be used prior to donning and/or doffing a stocking, and it may also be used to remove a stocking from apparatus 100 that the user has just doffed.

In general, apparatus 650 in this embodiment comprises a frame 652 supporting a rotatable gantry 654. A chain 656 (or rope, wire, or the like) is coupled with gantry 654 at its proximal end, and an attachment mechanism (e.g., a carabiner 658 or the like) is coupled with chain 656 at its distal end. Carabiner 658 may be attached to an apparatus for donning and/or doffing a stocking, and gantry 654 may be rotated to cause chain 656 to wind and unwind therefrom, thereby raising and lowering the apparatus.

Although a single chain 656 and carabiner 658 are shown in this embodiment, some embodiments may comprise a plurality of chains (or attachment points coupled with a single lift wire) that may be coupled with the apparatus for donning and/or doffing a stocking in multiple locations. For instance, a chain having four attachment points may be provided so that the four attachment points can be coupled with four clasp members on the apparatus for donning and/or doffing a stocking. As will be appreciated, this arrangement may serve to maintain the apparatus for donning and/or doffing a stocking in a level position as it is raised and/or lowered.

More particularly, frame 652 preferably is formed from a suitable strong but lightweight material (e.g., a lightweight metal or plastic material, which may be non-magnetic, such as PVC) that can be readily lifted and manipulated by a user. In this embodiment, frame 652 comprises a pair of telescoping posts 660, 662. Each post 660, 662 may comprise lower 664, middle 666, and upper 668 segments. Middle segment 666 may be adjustably received in an opening defined in lower segment 664, and upper segment 668 may be adjustably received in an opening defined in middle segment 666. Suitable fasteners 670 may be removably coupled with respective holes of a plurality of apertures defined in lower, middle, and upper segments 664, 666, 668 in order to adjust the height of frame 652. Lower segments 664 may each be coupled with a horizontally-extending foot 672, and a strut 674 may be coupled between each foot 672 and each lower segment 664. A cross-member 676 is coupled between the upper ends of upper segments 668.

Disposed beneath cross-member 676, gantry 654 also is rotatably coupled with upper segments 668, for example via brackets 678. A handle 680 coupled with gantry 654 may be used to manually rotate gantry 654 about its longitudinal axis, though in other embodiments, rotation of gantry 654 may be accomplished via any means, including an electric motor. Although not shown in FIG. 39, in various embodiments, a latch, interlocking links, ratchet mechanism, or other movable obstruction may be operatively connected with gantry 654 that, when actuated by a user, will releasably hold gantry 654 in position and prevent rotation thereof while an apparatus for donning and/or doffing a stocking is lifted. Preferably, frame 652 defines an area between posts 660, 662, feet 672, and gantry 654 that is sized to receive an apparatus for donning and/or doffing a stocking as described above.

Turning now to FIG. 40, illustrated is an apparatus 700. As described below, apparatus 700 may help assist a user in loading the sleeves of a stocking (where provided) onto a prong of a clasp member. In particular, apparatus 700 in this embodiment comprises a base portion 702 in which is received a retractable cord 704 (or cable or wire or the like). At a distal end of cord 704 is provided an attachment mechanism 706, such as an alligator clip as shown. Attachment mechanism 706 may, for example, have jaws that are biased toward the closed position. An attachment mechanism 708 (e.g., a carabiner, clip, clasp or the like) also is coupled with base portion 702. Attachment mechanism 708 preferably is adapted to releasably couple apparatus 700 with an apparatus for donning and/or doffing a stocking at a location proximate to a clasp member or its prong.

In use, prior to donning a stocking, an apparatus 700 (or multiple apparatuses 700) may be coupled with an apparatus for donning and/or doffing a stocking proximate to each clasp member to which a user desires to attach a sleeve of a stocking. If necessary using a reach-extender, the user may pull each attachment mechanism 706, thereby extending retractable cord 704, within easy reach of the user. The user may then attach mechanism 706 to each sleeve of the stocking. Then, the user may lower the stocking (again using the reach-extender if needed) toward the device. By virtue of the placement of each apparatus 700 proximate a clasp member, cords 704 will retract each sleeve of the stocking toward a respective clasp member. The user may then continue to lower the stocking until all of its sleeves are disposed over their respective prongs, and the user may then detach each attachment mechanism 700.

Next, FIG. 41 illustrates an apparatus 720. Apparatus 720 may be useful for users doffing a stocking, for example where the user has difficulty getting the sleeves of an already-clad stocking onto the prongs of clasp members of the apparatus for donning and/or doffing a stocking, or where the user has difficulty removing the unclad stocking's sleeves from the prongs. As shown, apparatus 720 comprises a ring 722 connected with a hook 724 via a length of chain 726. In various embodiments, chain 726 may instead comprise a cable, rope, cord, wire, or the like.

In use, when doffing a stocking, a user may place a hook 724 through an ankle-level sleeve of a stocking. The user may then place ring 722 onto the prong of a clasp member. If needed, the user may use a reach-extender to accomplish this placement. Then, the user may operate the apparatus to doff the stocking in the manner described above, allowing prong to pull the ring 722, which then pulls hook 724 and, correspondingly, a sleeve of the stocking, via chain 726.

Accordingly, the length of chain 726 may be relatively short in some embodiments (e.g., a few inches), in that a longer chain may not allow for sufficient stretching of the stocking. Multiple apparatuses 720 may be used, as needed or desired. After doffing the stocking, the user may withdraw the ring 722 from the prong and withdraw the stocking from the apparatus for donning and/or doffing the stocking, again using a reach extender, if needed.

Embodiments of the present invention also provide various methods. Examples of the methods performed in accordance with embodiments of the present invention are provided below and, with respect to certain methods, with reference to FIGS. 42-44.

First, FIG. 42 is a flow chart according to example methods in accordance with an embodiment of the present invention. At operation 800, the process starts. At operation 802, an apparatus is provided, and the apparatus comprises a frame comprising a first sub-frame and a second sub-frame that is slidable relative to the first sub-frame along a first direction. The apparatus also comprises at least one first peg coupled with the first sub-frame and at least one second peg coupled with the second sub-frame. At operation 804, a compression stocking is provided, and the compression stocking comprises a stocking body having a proximal end and a distal end. The stocking body defines an opening at least at the stocking body proximal end. The compression stocking also comprises a plurality of sleeves disposed on an exterior of the stocking body. Each of the plurality of sleeves oriented in a longitudinal direction relative to the stocking body. At operation 806, the at least one first peg and the at least one second peg are coupled with respective sleeves of the plurality of sleeves. At operation 808, the second sub-frame is slid relative to the first sub-frame in the first direction in order to expand the opening defined in the stocking body. At operation 810, a user's foot is inserted into the expanded stocking body opening. At operation 812, the second sub-frame is slid relative to the first frame to contract the opening defined in the stocking body about the user's foot. At operation 814, the process ends.

Next, FIG. 43 is a flow chart according to example methods in accordance with another embodiment of the present invention. At operation 820, the process starts. At operation 822, an apparatus is provided, and the apparatus comprises a base portion, a first rail coupled with the base portion, the first rail having a first longitudinal axis, and a second rail coupled with the base portion, the second rail having a second longitudinal axis. The apparatus also comprises a first post slidably coupled with the first rail, the first post slidable in a direction parallel with the first longitudinal axis between a first position and a second position, and a second post slidably coupled with the second rail, the second post slidable in a direction parallel with the second longitudinal axis between a third position and a fourth position. At operation 824, a stocking is provided, and the stocking comprises a stocking body defining at least one opening. The stocking also has a plurality of sleeves coupled to the exterior of the stocking body. At operation 826, respective sleeves of the plurality of sleeves of the stocking are releasably coupled to each of the base portion, first post, and second post. At operation 828, the first and second posts are slid from their respective first and third positions to their respective second and fourth positions, thereby expanding the stocking opening. At operation 830, the process ends.

FIG. 44 is a flow chart according to example methods in accordance with another embodiment of the present invention. At operation 840, the process starts. At operation 842, an apparatus is provided, and the apparatus comprises a frame comprising a first sub-frame and a second sub-frame that is slidable relative to the first sub-frame along a first direction. The apparatus also comprises at least one first clasp member coupled with the first sub-frame and at least one second clasp member coupled with the second sub-frame. At operation 844, a compression stocking is provided, and the compression stocking comprises a stocking body. The stocking body has an anterior portion and a posterior portion. At operation 846, the at least one first clasp member is coupled with the posterior portion of the compression stocking. At operation 848, the at least one second clasp member is coupled with the anterior portion of the compression stocking. At operation 850, the second sub-frame is slid relative to the first sub-frame in the first direction to expand the anterior portion of the compression stocking relative to the posterior portion of the compression stocking. At operation 852, a user's leg is inserted into the compression stocking, wherein after the user's leg is inserted, a proximal portion of the compression stocking is disposed proximate the user's knee, and a distal portion of the compression stocking is disposed proximate the user's ankle. At operation 854, the process ends.

Based on the foregoing, it will be appreciated that embodiments of the invention provide improved apparatus and methods for aiding a user in donning and/or doffing a stocking. Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:
1. A method, comprising:
   providing an apparatus comprising:
      a frame comprising a first sub-frame and a second sub-frame that is slidable relative to the first sub-frame along a first direction;
      at least one first peg coupled with the first sub-frame; and
      at least one second peg coupled with the second sub-frame;

providing a compression stocking comprising:
a stocking body, the stocking body having a proximal end and a distal end, the stocking body defining an opening at least at the stocking body proximal end; and
a plurality of sleeves disposed on an exterior of the stocking body, each of the plurality of sleeves oriented in a longitudinal direction relative to the stocking body;
coupling the at least one first peg and the at least one second peg with respective sleeves of the plurality of sleeves; and
sliding the second sub-frame relative to the first sub-frame in the first direction to expand the opening defined in the stocking body.

2. The method of claim 1, further comprising inserting a user's foot into the expanded stocking body opening.

3. The method of claim 2, wherein the first direction is an anterior-to-posterior direction relative to the user.

4. The method of claim 2, further comprising sliding the second sub-frame relative to the first sub-frame to contract the opening defined in the stocking body about the user's foot.

5. The method of claim 1, wherein each of the plurality of sleeves are cylindrical in shape.

6. The method of claim 1, wherein each of the plurality of sleeves has a sleeve longitudinal axis and the stocking body has a body longitudinal axis, wherein the sleeve longitudinal axes are parallel with the stocking body longitudinal axis.

7. The method of claim 1, wherein the sliding operation comprises actuating at least one linear actuator, the at least one linear actuator coupled between the first sub-frame and the second sub-frame.

8. The method of claim 1, further comprising providing a guiding apparatus, the guiding apparatus comprising a first post and a second post, each of the first post and the second post defining respective first and second openings therein, the first and second openings adapted to receive the at least one first peg and the at least one second peg, respectively.

9. The method of claim 8, wherein the coupling operation further comprises inserting each of the first post and the second post in a respective sleeve of the plurality of sleeves, disposing the first post over the at least one first peg, disposing the second post over the at least one second peg, removing the respective sleeves of the plurality of sleeves from the first post and the second post, withdrawing the first post from the at least one first peg, and withdrawing the second post from the at least one second peg.

10. A method, comprising:
providing an apparatus comprising:
a base portion;
a first rail coupled with the base portion, the first rail having a first longitudinal axis;
a second rail coupled with the base portion, the second rail having a second longitudinal axis;
a first post slidably coupled with the first rail, the first post slidable in a direction parallel with the first longitudinal axis between a first position and a second position; and
a second post slidably coupled with the second rail, the second post slidable in a direction parallel with the second longitudinal axis between a third position and a fourth position;
providing a stocking, the stocking comprising a stocking body defining at least one opening, the stocking having a plurality of sleeves coupled to the exterior of the stocking body;
releasably coupling a respective sleeve of the plurality of sleeves of the stocking to each of the base portion, first post, and second post; and
sliding the first and second posts from their respective first and third positions to their respective second and fourth positions, thereby expanding the stocking opening.

11. The method of claim 10, wherein the sleeves are deformable between an open position and a flattened position.

12. The method of claim 11, wherein the sleeves further comprise a tab adapted to retain a sleeve in the flattened position against the stocking.

13. The method of claim 11, further comprising one or more removable coils disposed within each sleeve to temporarily retain the sleeves in the open position.

14. The method of claim 10, wherein the sleeves are formed from a non-elastic material.

15. The method of claim 10, wherein the operation of releasably coupling comprises placing a first sleeve over a prong coupled with the base portion, placing a second sleeve over a prong coupled with the first post, and placing a third sleeve over a prong coupled with the second post.

16. The method of claim 10, wherein the stocking is a compression stocking.

17. A method, comprising:
providing an apparatus comprising:
a frame comprising a first sub-frame and a second sub-frame that is slidable relative to the first sub-frame along a first direction; and
at least one first clasp member coupled with the first sub-frame and at least one second clasp member coupled with the second sub-frame;
providing a compression stocking comprising a stocking body, the stocking body having an anterior portion and a posterior portion;
coupling the at least one first clasp member with the posterior portion of the compression stocking;
coupling the at least one second clasp member with the anterior portion of the compression stocking;
sliding the second sub-frame relative to the first sub-frame in the first direction to expand the anterior portion of the compression stocking relative to the posterior portion of the compression stocking; and
inserting a user's leg into the compression stocking, wherein after the user's leg is inserted, a proximal portion of the compression stocking is disposed proximate the user's knee, and a distal portion of the compression stocking is disposed proximate the user's ankle;
wherein the at least one first clasp member and the at least one second clasp member are coupled with the compression stocking at the compression stocking distal portion.

18. The method of claim 17, wherein the at least one first clasp member and the at least one second clasp member each comprise two clasp members.

19. The method of claim 17, wherein the apparatus further comprises at least one third clasp member coupled with the first sub-frame and at least one fourth clasp member coupled with the second sub-frame, wherein the at least one third clasp member and the at least one fourth clasp member are coupled with the compression stocking at the compression stocking proximal portion.

20. The method of claim 17, wherein the compression stocking further comprises at least one magnet removably coupled with the compression stocking proximate the compression stocking distal portion.

21. The method of claim 17, wherein the compression stocking body defines:
- a longitudinal axis;
    - a first angular position about the longitudinal axis corresponding to an anatomical anterior position;
    - a second angular position about the longitudinal axis corresponding to an anatomical posterior position;
    - a third angular position about the longitudinal axis corresponding to an anatomical medial position;
    - a fourth angular position about the longitudinal axis corresponding to an anatomical lateral position;
    - a first sleeve disposed on the stocking body at a fifth angular position about the longitudinal axis between the first and third angular positions;
    - a second sleeve disposed on the stocking body at a sixth angular position about the longitudinal axis between the second and third angular positions;
    - a third sleeve disposed on the stocking body at a seventh angular position about the longitudinal axis between the second and fourth angular positions; and
    - a fourth sleeve disposed on the stocking body at an eighth angular position about the longitudinal axis between the first and fourth angular positions.

22. The method of claim 17, wherein the second sub-frame is slidable relative to the first sub-frame along a second direction, the method further comprising sliding the second sub-frame relative to the first sub-frame in the second direction to expand the compression stocking in an anatomical medial-to-lateral direction.

* * * * *